(12) United States Patent
Beard et al.

(10) Patent No.: US 12,365,830 B2
(45) Date of Patent: Jul. 22, 2025

(54) LIGAND-EXCHANGEABLE JANUS NANOPARTICLES AND METHODS OF MAKING THE SAME

(71) Applicants: Alliance for Sustainable Energy, LLC, Golden, CO (US); The Regents of the University of Colorado, a Body Corporate, Denver, CO (US)

(72) Inventors: Matthew Craig Beard, Arvada, CO (US); Marissa Sally Martinez, Wheat Ridge, CO (US); Zhiyuan Huang, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 747 days.

(21) Appl. No.: 17/615,139

(22) PCT Filed: Jun. 10, 2020

(86) PCT No.: PCT/US2020/037073
§ 371 (c)(1),
(2) Date: Nov. 30, 2021

(87) PCT Pub. No.: WO2020/252075
PCT Pub. Date: Dec. 17, 2020

(65) Prior Publication Data
US 2022/0259490 A1 Aug. 18, 2022

Related U.S. Application Data

(60) Provisional application No. 62/861,850, filed on Jun. 14, 2019.

(51) Int. Cl.
| | | |
|---|---|---|
| C09K 11/02 | (2006.01) | |
| C07C 57/60 | (2006.01) | |
| C09K 11/66 | (2006.01) | |
| B82Y 20/00 | (2011.01) | |
| B82Y 40/00 | (2011.01) | |

(52) U.S. Cl.
CPC ............ *C09K 11/025* (2013.01); *C07C 57/60* (2013.01); *C09K 11/661* (2013.01); *B82Y 20/00* (2013.01); *B82Y 40/00* (2013.01); *C07B 2200/13* (2013.01)

(58) Field of Classification Search
CPC ..... C09K 11/025; C09K 11/661; B82Y 20/00; B82Y 40/00; C07B 2200/13; C07C 57/60; C07C 57/58
See application file for complete search history.

(56) References Cited

U.S. PATENT DOCUMENTS

| | | | |
|---|---|---|---|
| 10,128,390 B2 * | 11/2018 | Santiago-Berrios | ......................... H01L 31/0216 |
| 2008/0234394 A1 * | 9/2008 | Hong | ........................ B01J 13/00 516/22 |
| 2015/0218442 A1 | 8/2015 | Jun et al. | |
| 2015/0233936 A1 | 8/2015 | Tulsky et al. | |
| 2017/0362255 A1 | 12/2017 | Beard et al. | |
| 2019/0367805 A1 | 12/2019 | Kim et al. | |
| 2020/0067006 A1 * | 2/2020 | Ippen | ..................... H10K 50/15 |

FOREIGN PATENT DOCUMENTS

| | | |
|---|---|---|
| WO | 2019084119 A1 | 5/2019 |
| WO | 20200067006 A1 | 2/2020 |

OTHER PUBLICATIONS

Babajani et al., J. Phys. Chem. C, 2014, 118, 27142-27149. Published online Oct. 27, 2014 (Year: 2014).*
Bronstein et al., ACS Nano, 2019, 13, 38393846. Published online Mar. 11, 2019 (Year: 2019).*
Vilain et al., J. Mater. Chem, 2007, 17, 3509-3514. published online Jun. 19, 2007 (Year: 2007).*
Amin, V.A. et al., "Dependence of the Band Gap of CdSe Quantum Dots on the Surface Coverage and Binding Mode of an Exciton-Delocalizing Ligand, Methylthiophenolate," Journal of Physical Chemistry C, vol. 119, 2015, 7 pages.
Bhattacharya, D. et al., "Designing Coupled Quantum Dots with ZnS-CdSe Hybrid Structures for Enhancing Exciton Lifetime," Journal of Physical Chemistry C, vol. 122, 2018, 11 pages.
Coleman, B. et al., "Amphiphilic Quantum Dots with Asymmetric, Mixed Polymer Brush Layers: From Single Core-Shell Nanoparticles to Salt-Induced Vesicle Formation," Polymers, vol. 10, No. 327, 2018, 14 pages.
Du, J. et al., "Anisotropic particles with patchy, multicompartment and Janus architectures: preparation and application," Chem Soc. Rev., vol. 40, 2011, 15 pages.
Ebbens, S.J. et al., "Catalytic Janus Colloids: Controlling Trajectories of Chemical Microswimmers," Accounts of Chemical Research, vol. 51, 2018, 9 pages.
Embden, J.V. et al., "The formation mechanism of Janus nanostructures in one-pot reactions: the case of Ag-Ag8GeS6," Journal of Materials Chemistry A, vol. 4, 2016, 11 pages.
Falireas, P.G. et al., "pH-responsive polyampholytic hybrid Janus nanoparticles," Elsevier Polymer, vol. 130, 2017, 11 pages.
Frederick, M.T. et al., "Relaxation of Exciton Confinement in CdSe Quantum Dots by Modification with a Conjugated Dithiocarbamate Ligand," ACS Nano, vol. 4, No. 6, 2010, 6 pages.
Gandra, N. et al., "Bimetallic Janus nanostructures via programmed shell growth," Nanoscale, vol. 5, 2013, 4 pages.
Giansante,C. et al., "Darker-than-Black" PbS Quantum Dots: Enhancing Optical Absorption of Colloidal Semiconductor Nanocrystals via Short Conjugated Ligands, Journal of the American Chemical Society, vol. 137, 2015, 12 pages.
Green, M.L.H., "A new approach to the formal classification of covalent compounds of the elements," Journal of Organometallic Chemistry, vol. 500, 1995, 22 pages.

(Continued)

*Primary Examiner* — Jane L Stanley
(74) *Attorney, Agent, or Firm* — Michael A. McIntyre

(57) ABSTRACT

The present disclosure relates to a nanocrystal that includes a nanocrystal core, a first ligand coordinated to a first portion of a surface of the nanocrystal core, and a second ligand coordinated to a second portion of the surface, where the second ligand includes a first functionalized aromatic molecule.

20 Claims, 43 Drawing Sheets

(56) References Cited

OTHER PUBLICATIONS

Harris, R.D. et al., "Role of Interligand Coupling in Determining the Interfacial Electronic Structure of Colloidal CdS Quantum Dots," ACS Nano, vol. 10, 2016, 9 pages.
Harris, R.D. et al., "Electronic Processes within Quantum Dot-Molecule Complexes," Chemical Reviews, vol. 116, 2016, 55 pages.
Hendricks, M.P. et al., "A tunable library of substituted thiourea precursors to metal sulfide nanocrystals," Science, vol. 348, Issue 6240, 2015, 6 pages.
Jana, S. et al., "Ligand-induced twisting of nanoplatelets and their self-assembly into chiral ribbons," Science Advances Research Article, vol. 3, 2017, 7 pages.
Jiang, Z. et al., "Subnanometre ligand-shell asymmetry leads to Janus-like nanoparticle membranes," Nature Materials Letters, vol. 14, 2015, 7 pages.
Kroupa, D.M. et al., "In situ spectroscopic characterization of a solution-phase X-type ligand exchange at colloidal lead sulphide quantum dot surfaces," ChemComm Communication, vol. 52, 2016, 4 pages.
Kroupa, D.M. et al., "Tuning colloidal quantum dot band edge positions through solution-phase surface chemistry modification," Nature Communications, DOI: 10.1038/ncomms15257; 8 pages.
Kroupa, D.M. et al., "Optical Absorbance Enhancement in PbS QD/Cinnamate Ligand Complexes," Journal of Physical Chemistry Letters, vol. 9, 2018, 9 pages.
Liu,X. et al., "Determination of monolayer-protected gold nanoparticle ligand-shell morphology using NMR," Nature Communications, vol. 3, 2012, 9 pages.
Moreels, I. et al., "Ligand AdsorptionDesorption on Sterically Stabilizined InP Colloidal Nanocrystals: Observation and Thermodynamic Analysis," ChemPhysChem, vol. 7, 2006, 4 pages.
Moreels, I. et al., "Size-Dependent Optical Properties of Colloidal PbS Quantum Dots," ACS Nano, vol. 3, No. 10, 2009 8 pages.
Nomoev, A.V. et al, "Synthesis, Characterization, and Mechanism of Formation of Janus-Like Nanoparticles of Tantalum Silicide-Silicon (TaSix/Si)," Nanomaterials, vol. 5, 2015, 10 pages.
Ong, Q. et al., "Characterization of Ligand Shell for Mixed-Ligand Coated Gold Nanoparticles," Accounts of Chemical Research, vol. 50, 2017, 9 pages.
Owen, J., "The coordination chemistry of nanocrystal surfaces," Science, vol. 347, Issue 6222, 2015, 3 pages.
Percebom, A.M. et al., "Janus gold nanoparticles obtained via spontaneous binary polymer shell segregation," ChemComm Communication, vol. 52, 2016, 4 pages.
Ruhland, T.M. et al., "Nanoscale hybrid silica/polymer Janus particles with a double-responsive hemicorona," Polymer, vol. 79, 2015, 10 pages.
Schnitzenbaumer, K.J. et al., "Chalcogenide-Ligand Passivated CdTe Quantum Dots Can Be Treated as Core/Shell Semiconductor Nanostructures," Journal of Physical Chemistry C, vol. 118, 2014, 9 pages.
Sologan, M. et al., "Patchy and Janus Nanoparticles by Self-Organization of Mixtures of Fluorinated and Hydrogenated Alkanethiolates on the Surface of a Gold Core," ACS Nano, vol. 10, 2016, 10 pages.
Widmer-Cooper, A. et al., "Ligand-Mediated Interactions between Nanoscale Surfaces Depend Sensitively and Nonlinearly on Temperature, Facet Dimensions, and Ligand Coverage," ACS Nano, Vo. 10, 2016, 11 pages.
Yuwen, L. et al., "One-Pot Encapsulation of Luminescent Quantum Dots Synthesized in Aqueous Solution by Amphiphillic Polymers," Wiley Small, vol. 7, No. 10, 2011, 8 pages.
Zhang, J. et al., "Preparation of Cd/Pb Chalcogenide Heterostructured Janus Particles via Controllable Cation Exchange," ACS Nano Vol. 9, No. 7, 2015, 13 pages.
Zhang, Z. et al., "Tethered Nano Building Blocks: Toward a Conceptual Framework for Nanoparticle Self-Assembly," Nano Letters, vol. 3, No. 10, 2003, 6 pages.
Search Report and Written Opinion from Corresponding PCT Patent Application No. PCT/US20/37073, dated Sep. 11, 2020, 10 pages.

* cited by examiner

LIGAND-EXCHANGEABLE JANUS NANOPARTICLES AND METHODS OF MAKING THE SAME

CROSS-REFERENCE TO RELATED APPLICATIONS

This application claims priority from U.S. Provisional Patent Application No. 62/861,850 filed Jun. 14, 2019, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Colloidal semiconductor nanocrystals, or quantum dots (nanocrystals), have been an active area of research in numerous scientific disciplines due to their highly tunable optical and electronic properties. Since their initial discovery, researchers have used quantum confinement to easily tune nanocrystal band gaps throughout the visible and near infrared spectrum by varying the nanocrystal core material and diameter. Subsequently, researchers have found that surface chemistry also plays a vital role in emergent nanocrystal optical and electronic properties due to large nanocrystal surface to volume ratios at nanoscale sizes. Researchers have also pursued post synthetic surface chemistry modification, or ligand exchange, as another avenue of tailoring nanocrystals to make nanocrystal-ligand material systems with significantly diverse optical and electronic properties significantly unlike those of the starting nanocrystal-ligand system. However, there continues to be a need for reliable and flexible methods for synthesizing nanocrystal-ligand systems having a range of tunable physical properties and/or performance metrics.

SUMMARY

An aspect of the present disclosure is a nanocrystal that includes a nanocrystal core, a first ligand coordinated to a first portion of a surface of the nanocrystal core, and a second ligand coordinated to a second portion of the surface, where the second ligand includes a first functionalized aromatic molecule. In some embodiments of the present disclosure, the first functionalized aromatic molecule may include at least one of cinnamic acid (CAH) and/or a first functionalized CAH molecule.

In some embodiments of the present disclosure, the first functionalized CAH molecule may include at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tertbutyl-cinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, and/or 3,4-(2,5-pyrrolidinedione) cinnamic acid.

In some embodiments of the present disclosure, wherein the first ligand may include at least one of an alkyl carboxylate, an alkyl amine, an alkyl phosphine, an alkyl phosphonate, and/or an alkyl thiolate. In some embodiments of the present disclosure, the first ligand may include a second functionalized aromatic molecule that is different than the first functionalized aromatic molecule. In some embodiments of the present disclosure, the second functionalized aromatic molecule may include at least one of CAH and/or a second functionalized CAH molecule.

In some embodiments of the present disclosure, the second functionalized CAH molecule may include at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tertbutyl-cinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, and/or 3,4-(2,5-pyrrolidinedione) cinnamic acid.

In some embodiments of the present disclosure, the nanocrystal core may have an average particle size between 1 nm and 100 nm. In some embodiments of the present disclosure, the nanocrystal core may include at least one of a Group II element, a Group III element, a Group IV element, a Group V element, Group VI element, and/or a noble metal. In some embodiments of the present disclosure, the nanocrystal core may include at least one of PbS, PbSe, PbTe, CdS, CdSe, CdTe, ZnS, ZnSc, ZnTe, HgS, HgSc, HgTe, GaN, GaP, GaAs, InP, InAs, Si. Ge, Au, Ag, Pt, Cu, Ni, $AgSbS_2$, $AgSbSc_2$, $CuInS_2$, $CuInSc_2$, CuInSSe, $CuzSnS_3$, $CuzSnSc_3$, CZTS, CZTSe, and/or CZTSSe. In some embodiments of the present disclosure, the second portion may be between 10% and 90% of the surface.

An aspect of the present disclosure is a method that includes adding an exchange ligand to a first solution that includes a first solvent and a starting nanocrystal that includes a starting ligand coordinated to a surface of a nanocrystal core, where the adding produces an exchanged nanocrystal in a second solution, the starting ligand and the exchange ligand have a ligand-ligand coupling energy less than $-0.44\ k_B T$, where $k_B$ is the Boltzmann constant and T is the temperature in Kelvin, the exchange ligand includes a functionalized aromatic molecule, the nanocrystal core includes at least one of a Group II element, a Group III element, a Group IV element, a Group V element, Group VI element, or a noble metal, the exchange ligand replaces at least a portion of the starting ligand coordinated to a portion of the surface, and the exchange ligand coordinates to the portion of the surface to produce the exchanged nanocrystal.

In some embodiments of the present disclosure, the first solution may be maintained at a temperature between 20° C. and 30° C. In some embodiments of the present disclosure, the exchange ligand may be added at a ratio of moles of exchange ligand to moles of nanocrystal core between 1:10 and 1000:1. In some embodiments of the present disclosure, the method may further include, prior to the adding, preparing the first solution comprising the nanocrystal core, the starting ligand, and the first solvent to produce the starting nanocrystal, where, the first solvent has a high solubility for the nanocrystal core.

BRIEF DESCRIPTION OF THE DRAWINGS

Some embodiments are illustrated in referenced figures of the drawings. It is intended that the embodiments and figures disclosed herein are to be considered illustrative rather than limiting.

FIG. 7A illustrates raw data for the 4(CN)$_2$ derivative. As the R-CA-/nanocrystal equivalents increased, as indicated by the arrow, the absorption of the nanocrystal solutions increased. Integrating from 1 eV to 2.5 eV avoided contributions from the ligand absorption (asterisked trace). FIG. 7B illustrates a plot of the absorption enhancement as a function of Ligand equivalents. After the addition of ~400 ligand equivalents the absorption enhancement became saturated, as indicated by the vertical dashed line. (QDs=nanocrystals)

FIG. 10A illustrates the change in free energy for the ligand/nanocrystal binding versus the cinnamate dipole moment (triangles) and dashed-line is a calculation of the electrostatic dipole-dipole interaction energy (described in text), while FIG. 10B illustrates the ligand/ligand non-binding interaction energy versus the dipole moment. The individual points are labeled in both FIGS. 10A and 10B to correspond to the labeling shown in FIG. 6.

FIG. 14A illustrates the $^{19}$F chemical shift as a function of CF$_3$-CA$^-$ exchange. The $1/X_A$ dependence is indicative of patchy/cooperative ligand exchange. FIG. 14B illustrates the $^{19}$F chemical shift as a function of 2,6-2F-CA$^-$ exchange. The linear dependence is indicative of the isotropic ligand shell during exchange. FIG. 14C illustrates the 2D NOESY spectrum of 3,5-F-CA (69%)/OA$^-$ mixed coverage and FIG. 14D illustrates the 2,6-F-CA$^-$ (53%)/OA$^-$ mixed ligand coverage. Resonances arise from the oleate methyl and ethyl groups ($\delta$=1-2.5 ppm), oleate vinyl ($\delta$=5.4 ppm), cinnamate aryl group ($\delta$=5.8-8 ppm), and sharp peaks are from the standards (ferrocene, $\delta$=4.15 ppm; hexafluoro isopropanol, $\delta$=4.5 ppm) and solvent (chloroform-d, $\delta$=7.2 ppm).

FIG. 16A illustrates $^1$H NMR spectra of 20, 26, 44, 52, 79, and 100% PbS/CF$_3$-CA in the oleate vinyl ($\delta$=5.3-5.4 ppm) region, which shows some unbound oleate by the sharp up-field resonance. The broad peak was integrated to get the number of bound oleates. FIG. 16B illustrates the $^{19}$F {$^1$H} spectra for the PbS/CF$_3$-CA$^-$($\delta$=−63.4--64.4 ppm) at the same percentages as shown in FIG. 16A fitted with multiple Gaussian peaks. The 100% $CF_3$-CA- sample (bottom trace) shows a significant amount of unbound cinnamate with a resonance at 64.4 ppm, as denoted by the vertical line, and samples 20-44% show small amounts of what is likely to be the unbound ligand, whereas 52 and 79% traces do not. FIG. 16C illustrates spectra of 100% $CF_3$-CA$^-$ from a purified sample (solid line-no residual $CF_3$-CAH), and a sample with the sharp peak (dashed line) from the presence of residual unbound ligand. Since the two peaks have the same chemical shift, one can conclude that the presence of unbound cinnamate did not significantly influence the chemical shift of the bound peak. To further show this, the shifts of the broad peaks illustrated in FIG. 16B are plotted versus the $CF_3$-CA$^-$ coverage FIG. 16D and yield a similar dependence as that shown in FIG. 14A.

FIG. 22A—PbS/OA nanocrystals assembled under 20 V; FIG. 22B—Janus PbS nanocrystals assembled under 20 V; and FIG. 22C 120 V.

Figure 1A:
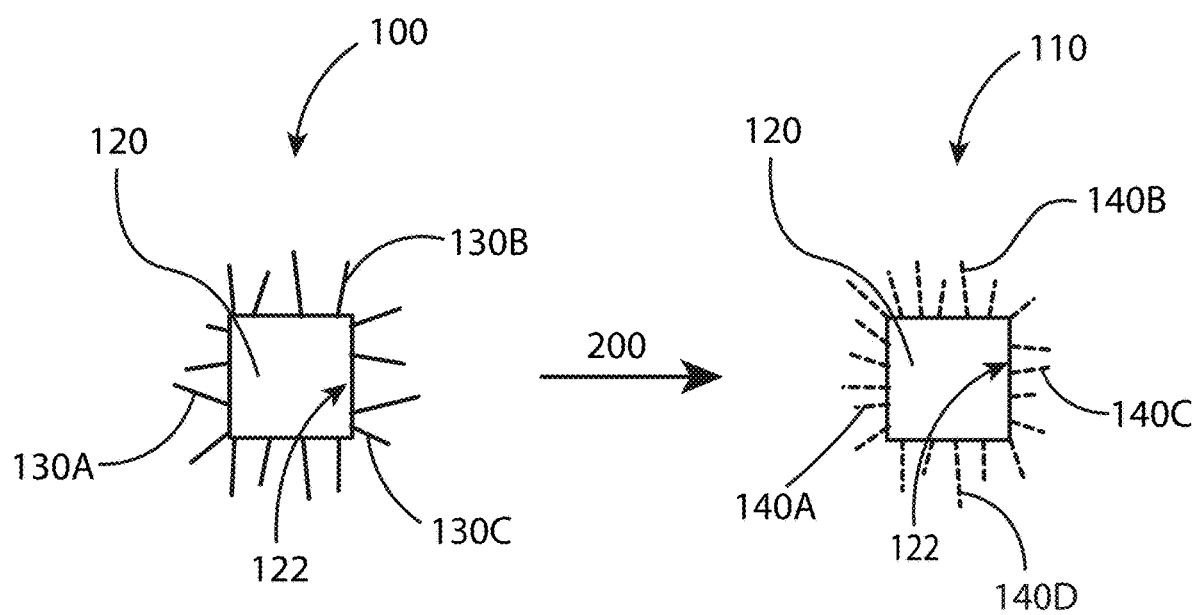
FIG. 1A illustrates a starting nanocrystal that includes a nanocrystal core and a starting ligand, and a final nanocrystal that includes the nanocrystal core and an exchange ligand, according to some embodiments of the present disclosure.

| REFERENCE NUMBERS | |
|---|---|
| 100 | starting nanocrystal |
| 110 | final nanocrystal |
| 115 | partially exchanged nanocrystal |
| 120 | nanocrystal core |
| 122 | surface |
| 130 | starting ligand |
| 140 | exchange ligand |
| 150 | first portion |
| 155 | second portion |
| 200 | method |
| 210 | preparing |
| 212 | first solvent |
| 214 | first solution |
| 220 | adding exchange ligand |
| 222 | second solution |
| 230 | precipitating |
| 232 | precipitating agent |
| 234 | mixture |
| 240 | separating |
| 242 | liquid phase |
| 244 | solid phase |
| 250 | stabilizing |
| 252 | third solvent |
| 254 | ink |

DETAILED DESCRIPTION

The present disclosure may address one or more of the problems and deficiencies of the prior art. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target.

In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

The present disclosure relates to ligand stabilized nanocrystal cores, in particular lead sulfide and/or lead selenide nanocrystal cores stabilized by functionalized aromatic molecules that are coordinated with one or more exposed surfaces of the nanocrystal cores. The present disclosure also relates to methods for producing such ligand stabilized nanocrystal cores. FIG. 1A illustrates a starting nanocrystal 100 that includes a nanocrystal core 120 having at least one surface 122 such that a starting ligand 130 (e.g. 130A-C) can coordinate with the surface 122.

As used herein, the term "coordinate" refers to a binding relationship between the nanocrystal core 120 and a ligand, in this case, at least one of a starting ligand 130 and/or an exchange ligand 140. So, in general, a ligand coordinated with a surface of a nanocrystal core refers to at least one of a covalent bond, an ionic bond, a van der Waals interaction, dipole-dipole interactions, and/or a hydrogen-bond between the surface of the nanocrystal core and a binding group that attaches the ligand to the surface of the nanocrystal.

A nanocrystal core may be constructed of any suitable material with examples including Group II-VI elements, Group III-V elements, Group IV-VI elements, Group IV elements, a noble metal, a transition metal oxide, and/or a ternary, quaternary, and/or penternary compound, with examples including, but not limited to, PbS, PbSe, PbTe, CdS, CdSe, CdTe, ZnS, ZnSe, ZnTe, HgS, HgSe, HgTe, GaN, GaP, GaAs, InP, InAs, Si, Ge, Au, Ag, Pt, Cu, and Ni, $AgSbS_2$, $AgSbSc_2$, $CuInS_2$, $CuInSc_2$, CuInSSe, $CuzSnS_3$, $CuzSnSe_3$, CZTS, CZTSe, CZTSSe, or mixtures thereof. In some embodiments of the present disclosure, a nanocrystal core may be of substantially one material phase. In some embodiments of the present disclosure, a nanocrystal core may be of two or more material phases (e.g. a heterostructure nanocrystalline core), such as at least one of a uniformly mixed alloy type nanocrystal core, a core-shell type nanocrystal core, dot-in-rod type nanocrystal core, dot-on-rod type nanocrystal core, and/or Janus particle type nanocrystal core. A nanocrystal core may have a characteristic length between 1 nm and 100 nm. A nanocrystal core may have a least one of a crystalline, semi-crystalline, and/or amorphous structure. A nanocrystal may have any suitable shape, for example at least one of a spherical shape, a cylindrical shape, an irregular shape, and/or any other suitable shape. A starting ligand may include at least one of an alkyl carboxylate, an alkyl amine, an alkyl phosphine, an alkyl phosphonate, and/or an alkyl thiolate.

Figure 2:
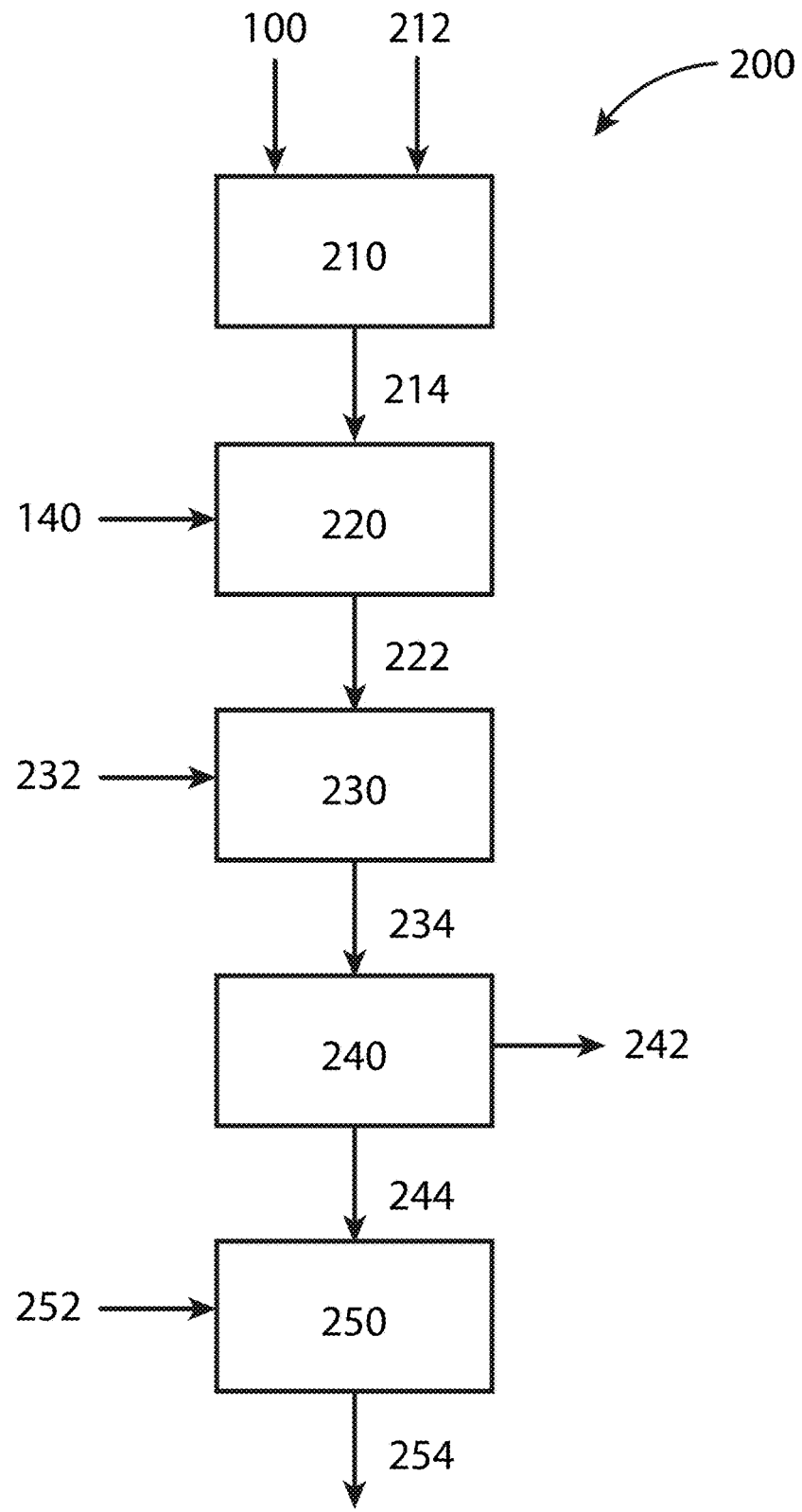
FIG. 2 illustrates a method for converting a starting nanocrystal that includes a nanocrystal core and a starting ligand to a final nanocrystal that includes the nanocrystal core and an exchange ligand, according to some embodiments of the present disclosure.

FIG. 1A illustrates that a starting nanocrystal 100 constructed of a nanocrystal core 120 coordinated with a starting ligand 130 (e.g. three starting ligands, 130A, 130B, and 130C, are called out) may be transformed into a final nanocrystal 110 constructed of the nanocrystal core 120 coordinated with an exchange ligand 140 (e.g. four exchange ligands, 140A, 140B, 140C, and 140D, are called out) when treated according to an appropriate method, as described herein (see FIG. 2). A method 200 may result in an exchange of at least a portion of the starting ligand 130 coordinated with a surface 122 of the nanocrystal core 120 by the exchange ligand 140. As a result, the final nanocrystal 110 may include at least some exchange ligands 140 coordinated to the surface 122 of the nanocrystal core 120. In some embodiments of the present disclosure, substantially all of the starting ligand 130 may be removed from the surface 122 of the nanocrystal core 120, such that substantially all of the available surface 122 may coordinate with the exchange ligand 140.

Figure 1B:
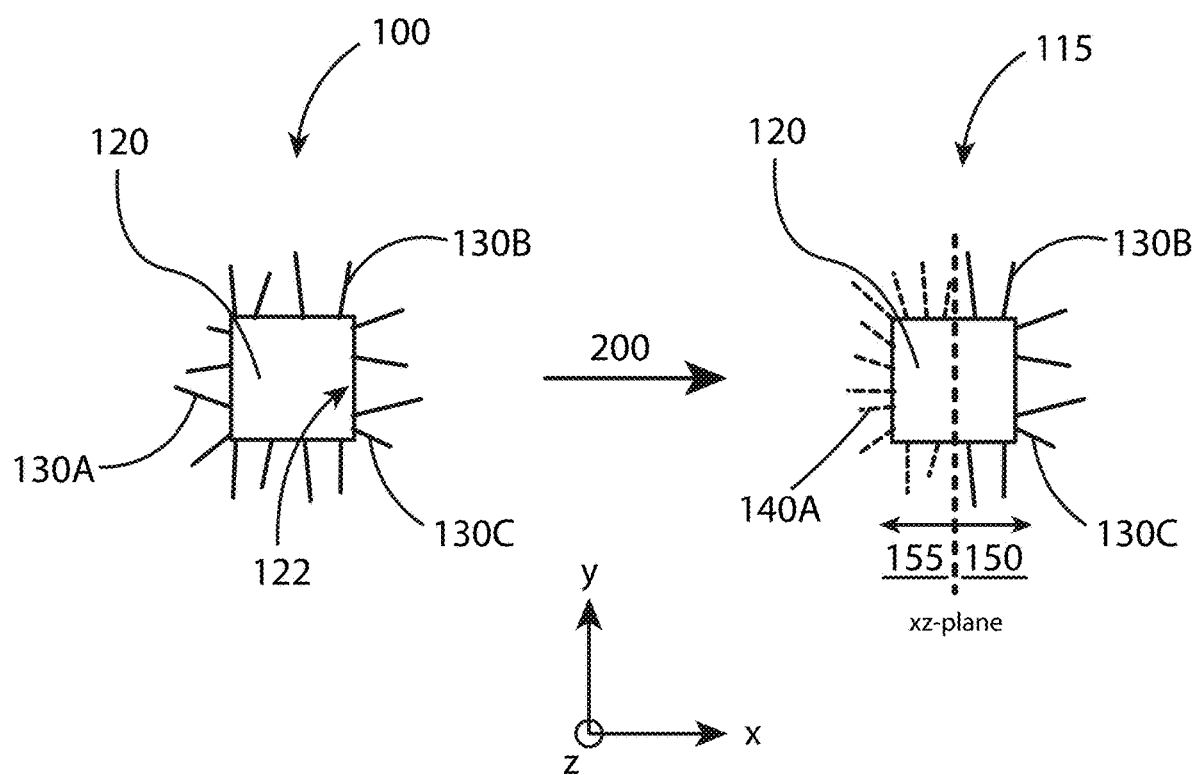
FIG. 1B illustrates a starting nanocrystal that includes a nanocrystal core and a starting ligand, and a final nanocrystal that includes the nanocrystal core and an exchange ligand, according to some embodiments of the present disclosure.

Referring to FIG. 1B, in some embodiments of the present disclosure, a fraction of the starting ligand 130 (e.g. three ligands, 130A, 130B, and 130C, are called out) may be removed from the surface 122 of the nanocrystal core 120, such that only a portion of the surface 122 may coordinate with the exchange ligand 140 (e.g. only one exchange ligand called out, 140A), resulting, for example, in a partially exchanged nanocrystal (i.e. nanoparticle) 115 where a first portion 150 of the surface 122 of the partially exchanged nanocrystal 115 remains substantially covered with the starting ligand 130 and a second portion 155 of the surface 122 of the partially exchanged nanocrystal 115 is substantially covered with the exchange ligand 140. In the examples of FIGS. 1A and 1B, the nanocrystals (100, 110, and 115) are shown as two-dimensional cross-sections. To illustrate this, the partially exchanged nanocrystal 115 of FIG. 1B shows an xz-plane, which divides the partially exchanged nanocrystal 115 into two the portions, a first portion 150 where substantially none of the starting ligands 130 are exchanged and a second portion 155 where substantially all of the starting ligands 130 are exchanged with the exchange ligand 140.

The partially exchanged nanocrystal 115 of FIG. 1B shows an example where approximately 50% of the surface 122 of the partially exchanged nanocrystal 115 is covered by the starting ligand 130, with the remaining 50% of the surface 122 covered by the exchange ligand 140, resulting in a Janus nanocrystal. However, it should be understood that partially exchanged nanocrystals having different fractions of surface coverage are possible. For example, in some embodiments of the present disclosure, the fraction of the surface 122 covered by the exchange ligand 140 may be between 10% and 90%, with the remaining fraction of the surface covered by the starting ligand 130. In some embodiments of the present disclosure, the fraction of the surface 122 covered by the exchange ligand 140 may be between 30% and 70%, with the remaining fraction of the surface covered by the starting ligand 130. In some embodiments of the present disclosure, the fraction of the surface 122 covered by the exchange ligand 140 may be between 40% and 60%, with the remaining fraction of the surface covered by the starting ligand 130. In addition, the exemplary partially exchanged nanocrystal 115 of FIG. 1B shows a single first portion 150 that has not undergone the exchange, and therefore, is still covered by the starting ligand 130, and a single second portion 155 that has undergone the exchange, and therefore, is covered by the exchange ligand 140. However, in some embodiments of the present disclosure, a partially exchanged nanocrystal 115 may have one or more first portions 150 covered substantially with the starting ligand 130 and/or one or more second portions 155 covered substantially with the exchange ligand 140. For example, a partially exchanged nanocrystal 115 may have a surface 122 that is covered with multiple patches of the exchange ligand 140 interspersed among the starting ligand 130.

Figure 3:
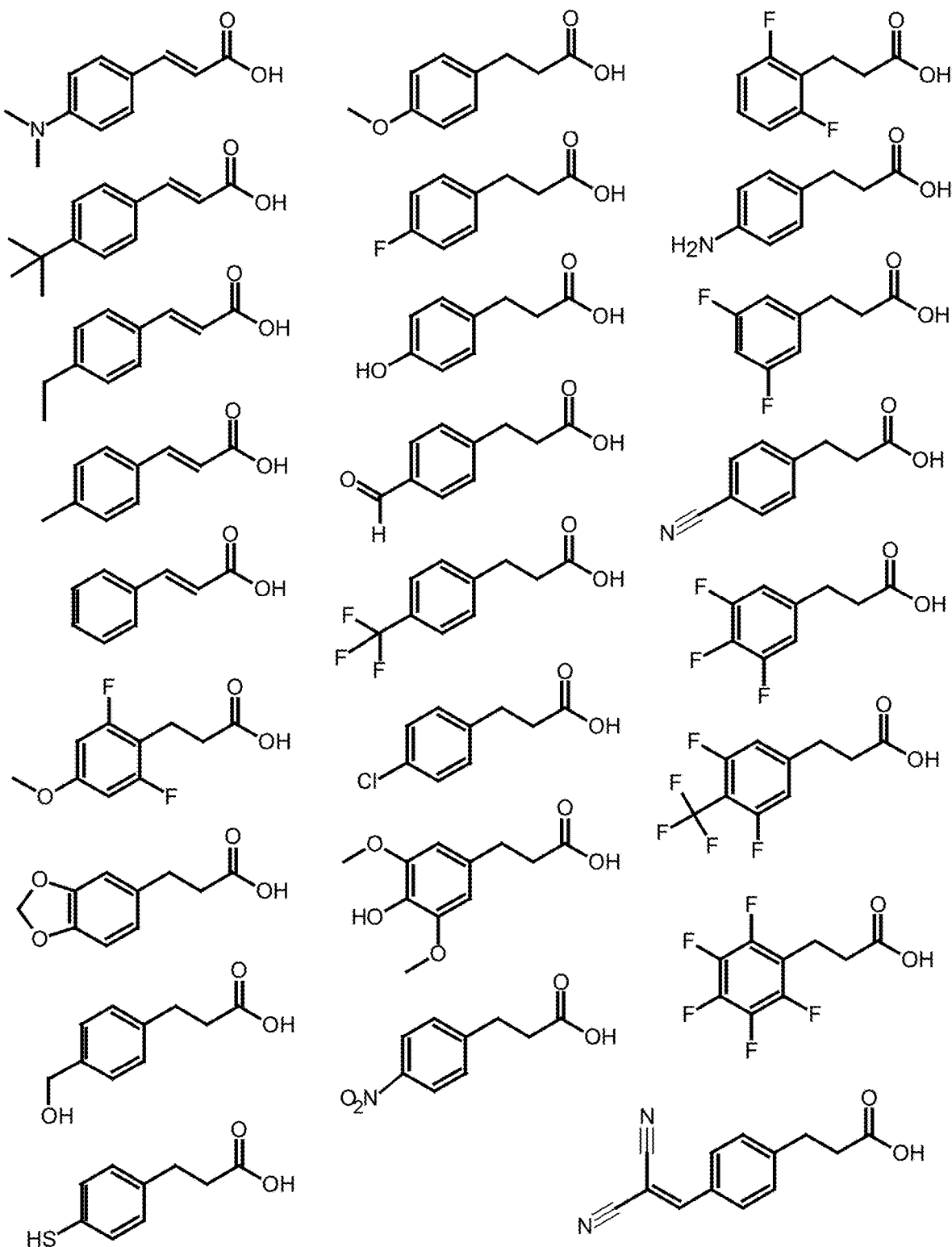
FIGS. 3-5 illustrate some examples of exchange ligands, according to some embodiments of the present disclosure.
Figure 4:
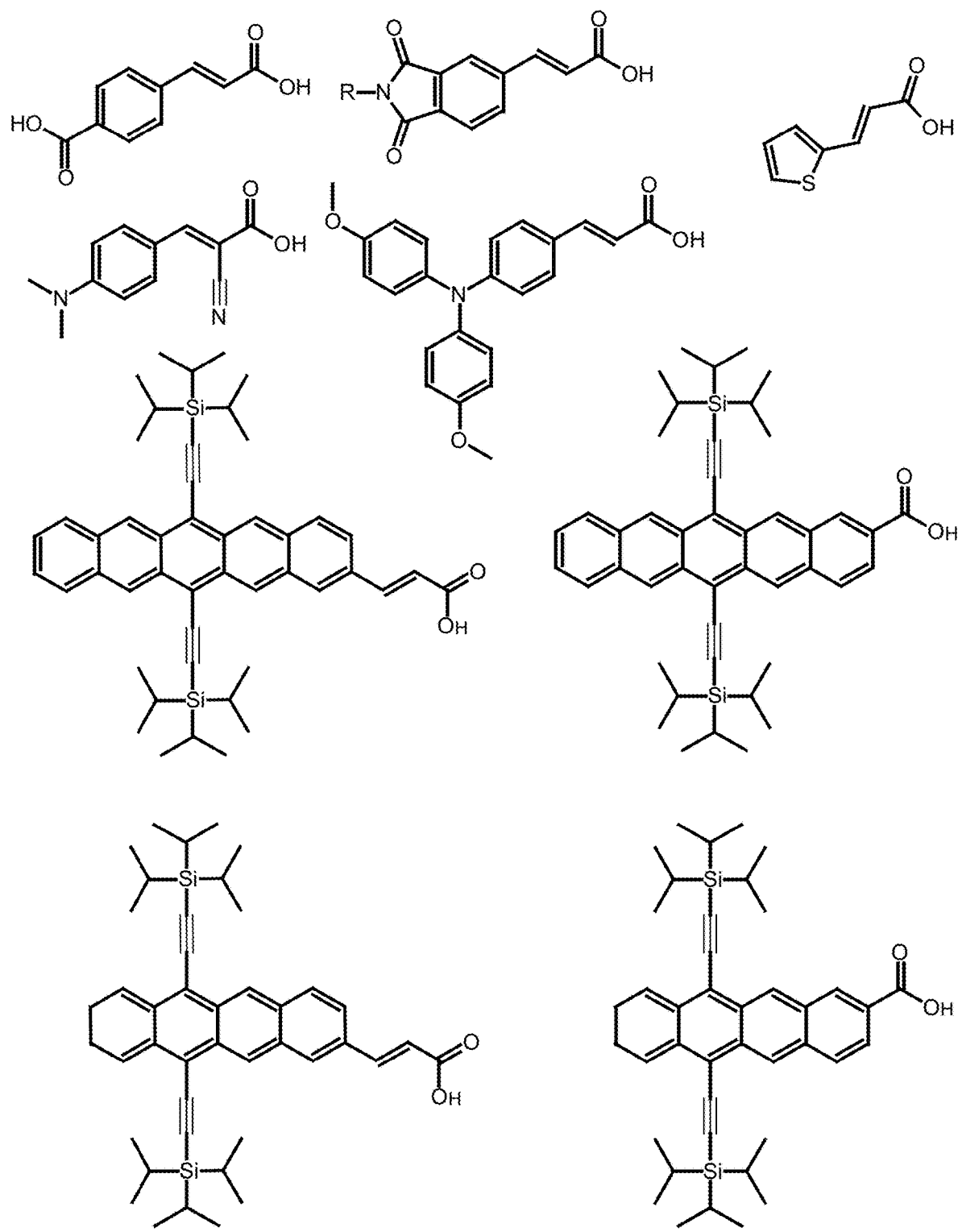
Figure 5:
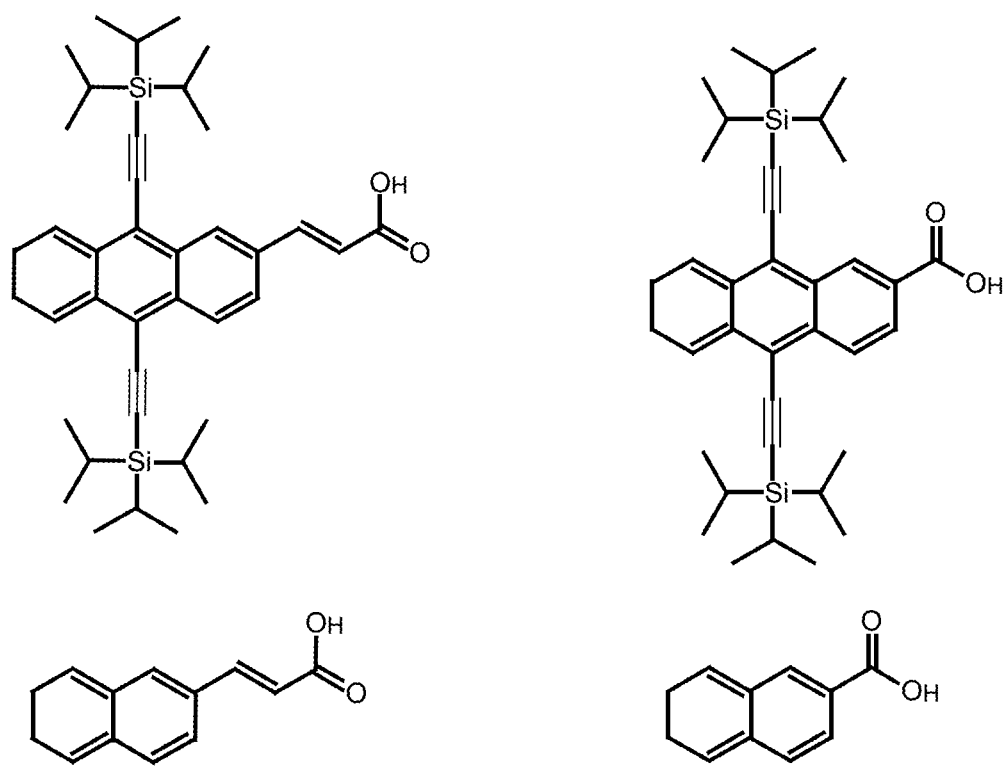

Suitable exchange ligands 140 include at least one ligand represented by,

B-L-A-R$_A$ where B is a binding group that coordinates the ligand to the surface of the nanocrystal core, where B includes, for example, —CN, —COOH, —CSSH, —SH, —NR$_2$, —POOOH (where R is a hydrogen atom or a saturated and/or unsaturated aliphatic hydrocarbon group), and/or any other suitable functional group. L is a linking group between the binding group (B) and backbone (A), where the linking group may be linked to B and A by direct bonding and may be for example, an aliphatic organic group and/or an aromatic organic group. The backbone group (A) may include, for example, a single carbon atom, a benzene ring, a polyacene, and/or any other suitable aromatic molecule. R$_A$ is a functional group, and may include for example any combination of substitutional groups described by Hansch (Chem. Rev. 91, 165, (1991)), which is incorporated by reference herein in its entirety, and placed at any position(s) on the ligand aromatic backbone or linking group. Examples of some suitable exchange ligands are illustrated in FIGS. 3-5, according to some embodiments of the present disclosure.

Thus, in some embodiments of the present disclosure, an exchange ligand 140 may be a functionalized aromatic molecule, for example cinnamic acid (CAH) or a functionalized CAH. Other examples of functionalized aromatic molecules include at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tertbutylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, 3,4-(2,5-pyrrolidinedione) cinnamic acid, styrylphosphonic acid, 4-formylstyrylphosphonic acid, (4-(2,2-dicyanovinyl) styryl)phosphonic acid, 2,6-difluorostyrylphosphonic acid, 4-trifluoromethylstyrylphosphonic acid, 4-methoxystyrylphosphonic acid, 3-methylstyrylphosphonic acid, benzoic acid, 4-methylbenzoic acid, 4-mercaptobenzoic acid, 4-methoxybenzoic acid, 4-fluorobenzoic acid, 4-hydroxybenzoic acid, 4-nitrobenzoic acid, 4-cyanobenzoic acid, 4-formylbenzoic acid, 4-trifluoromethylbenzoic acid, 4-chlorobenzoic acid, 4-bromobenzoic acid, 4-iodobenzoic acid, 4-fluorobenzoic acid, 2,6-difluorobenzoic acid, trans-3-(3-thienyl) acrylic acid, 6,13-bis(triisopropylsilylethynyl)-pentacene-2-carboxylic acid, 6,13-bis(triisopropylsilylethynyl)-pentacene-2-acrylic acid, 6,11-bis(triisopropylsilylethynyl)-tetracene-2-carboxylic acid, 6,11-bis(triisopropylsilylethynyl)-tetracene-2-acrylic acid, 5,10-bis(triisopropylsilylethynyl)-anthracene-2-carboxylic acid, 5,10-bis(triisopropylsilylethynyl)-anthracene-2-acrylic acid, naphthalene-2-carboxylic acid, and/or naphthalene-2-acrylic acid.

FIG. 2 illustrates method 200 for producing a stable colloid and/or ink 254 that includes stabilized nanocrystals as described above and shown in FIGS. 1A and 1B and containing exchange ligands as described herein. In the example of FIG. 2, the method 200 begins with the preparing 210 of a first solution 214 by combining a starting nanocrystal 100 (as described above that includes the nanocrystal core 120 coordinated with the starting ligand 130) with a first solvent 212. The first solvent 212 may be any suitable solvent having a suitably high solubility for the starting nanocrystal 100. So, the choice of first solvent 212 may depend on at least one of the starting nanocrystal 100 and/or the final nanocrystal 110 chosen for a specific recipe for the ink 254. Thus, the first solvent 212 may be a polar solvent and/or a non-polar solvent with examples including toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, and/or water. The first solution 214 may be prepared in any suitable vessel and/or equipment (e.g. a stirred tank, static mixer, chromatography column) in either a continuous mode, semi-continuous mode, and or batch mode.

Once the first solution 214 containing the starting nanocrystal 100 of the starting ligand 130 coordinated to a surface 122 of the nanocrystal core 120 is complete, the method 200 may proceed with the adding 220 of an exchange ligand 140 to the first solution 214, resulting in the formation of a second solution 222. In some embodiments of the present disclosure, the adding 220 of the exchange ligand 140 may occur in the same unit operation (e.g. stirred tank) that was used to make the first solution 214. In some embodiments of the present disclosure, the adding 220 of the exchange ligand 140 may occur in a separate piece of equipment. The adding 220 may be completed in any suitable vessel and/or equipment (e.g. a stirred tank, static mixer, chromatography column) in either a continuous mode, semi-continuous mode, and/or batch mode. The exchange ligand 140 may be added to the first solution 214 such that the ratio of the exchange ligand 140 to the nanocrystal core 120 in the second solution 222 is between 1:1 and 1000:1. In some embodiments of the present disclosure, the exchange ligand 130 may be mixed with a second solvent 232 to form a solution (not shown) containing the exchange ligand 130, such that this solution is added to the first solution 214 shown in FIG. 2. A second solvent 232 may be any suitable solvent having a suitably high solubility for the exchange ligand 140. Thus, the second solvent 232 may be a polar solvent and/or a non-polar solvent with examples including toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, and/or water. In some embodiments of the present disclosure, the solution containing the exchange ligand 130 may be added to the first solution 214 utilizing a static mixer and/or a stirred tank reactor and/or a size-exclusion chromatography column. The adding 220 of the exchange ligand 140 to the first solution 214 results in the partial or complete exchange of the starting ligand 140 coordinated to a surface 122 of the nanocrystal core 120 with the exchange ligand 140, such that at least some of the surface 122 of the nanocrystal core 120 is coordinated with the exchange ligand 140, as described above.

In some embodiments of the present disclosure, the final nanocrystal 110 of the exchange ligand 140 coordinated to the nanocrystal core 120 may be substantially soluble in the second solution 222, although depending on the process conditions and components chosen for a specific application, the final nanocrystal 110 may be only partially soluble. Thus, in some embodiments of the present disclosure, the final nanocrystal 110 may have a first soluble component and a second, insoluble, solid-phase component. However, for the example shown in FIG. 2, the final nanocrystal 110 (not shown), contained in the second solution 222, is substantially dissolved (e.g. where substantially is greater than 80%, or >90%, or >99%) in the second solution 222. As a result, the method 200 may proceed with the precipitating 230 of the final nanocrystal 110 from the second solution 222, where the precipitating 230 is induced by the addition of a precipitating agent 232 to the second solution 222, resulting in the formation of a mixture 234 containing both a liquid phase and a precipitate of the final nanocrystal 110.

As used herein, a precipitating agent 232 may be any compound capable of reducing the solubility of the final nanocrystal 110 in the second solution 222 to the point where a significant fraction of the final nanocrystal 110 comes out of solution in the solid form. Thus, in some embodiments of the present disclosure, the precipitating agent 232 may include a third solvent (not shown). This third solvent may be any suitable polar and/or non-polar solvent with examples including at least one of pentane, cyclohexane, hexane, heptane, octane, toluene, acetone, acetonitrile, methanol, and/or ethanol. Alternatively, the temperature of the second solution 222 may be lowered such that the solubility of the final nanocrystal 110 in the second solution 222 is reduced to the point where a significant fraction of the final nanocrystal 110 comes out of solution in the solid form. The precipitating 230 may be achieved in the same unit operation used to perform the preparing 210 and the adding 220. Such a scenario may be desirable for batch operations. However, in some embodiments of the present disclosure, the precipitating 230 may be achieved in a separate unit operation; e.g. in a continuous stirred tank for larger-scale continuous operations).

Referring again to FIG. 2, a method 200 may proceed by treating the mixture 234 by separating 240 the final nanocrystal 110 from the mixture 234, resulting in the formation of a solid phase 244 containing the final nanocrystal 110 and a liquid phase 242 that is substantially free of the final nanocrystal 110. In some embodiments of the present disclosure, the separating 240 may be achieved by any suitable solid-liquid separation unit operation with examples including filtration, centrifugation, and/or electrostatic separation methods.

In the exemplary method 200 shown in FIG. 2, a method 200 may conclude by stabilizing 250 the solid phase 244 containing the final nanocrystal 110 to form the final targeted ink 254. In some embodiments of the present disclosure, the ink 254 may be formed by the addition of a third solvent 252 to the solid phase 244. In this case, it is desirable to choose a third solvent 252 for which the final nanocrystal 110 has a high colloidal stability so as to maintain a large percentage of the final nanocrystal 110 in the solution phase when mixed with the third solvent. Thus, depending on the other process conditions and the physical properties of the final nanocrystal 110, any suitable third solvent mixture 252 may be used with examples including toluene, benzene, chlorobenzene, dichlorobenzene, nitrobenzene, dichloromethane, tetrachloroethylene, chloroform, carbon tetrachloride, acetone, acetonitrile, methyl acetate, ethyl acetate, tetrahydrofuran, diethyl ether, methanol, ethanol, propanol, butanol, N-methyl formamide, N,N-dimethylformamide, dimethyl sulfoxide, and/or water.

It should be noted that although the exemplary method 200 described above and illustrated in FIG. 2 describes the use of three solvents, three solvents are not necessarily required, either to produce the final nanocrystal 110 and/or the ink 254. In most situations at least one solvent will be needed, e.g. for the adding 220 of the exchange ligand 140 to the starting nanocrystal 100 to achieve the exchange of at least a portion of the starting ligand 130 with the exchange ligand 140, as described above. So, it is conceivable that alternative methods may involve a single solvent containing the starting nanocrystal 100 to which the exchange ligand 140 may be added or a single solvent containing the exchange ligand 140 to which the starting nanocrystal 100 may be added. Subsequent method steps, e.g. precipitating 230 and/or stabilizing 250, may be accomplished by other means; e.g. by changing the concentration of the same solvent used in the adding 220 and/or by changing the temperature of at least one of the first solution 212, the second solution 222, and/or the mixture 234. These and other variations of the method 200 shown in FIG. 2 are within the scope of the present disclosure.

Thus, in summary, the present disclosure relates to solution phase ligand exchange methods for modifying nanocrystals (i.e. quantum dots), including nanocrystals having PbS nanocrystalline cores, where the exchange ligands include functionalized aromatic organic molecules. The present disclosure describes large-scale solution-phase ligand exchanges that completely replace starting ligands such as oleate ligands with functionalized aromatic organic acid molecule exchange ligands. The present disclosure relates to methods that enable the design of nanocrystals, nanocrystal-containing materials, and/or nanocrystal-containing systems having specific enhanced performance metrics, for example, broadband optical absorbance and absolute band edge energy level shifts. For the specific case of cinnamic acid exchange ligands, and as described herein, eight different functionalized cinnamic acid ligands (molecules) were extensively characterized and tested. For these eight exchange ligands, HOMO/LUMO energy gaps between about 3 eV and about 5 eV and dipole moments between about −6 Debye to 8 Debye were measured, while the ligand/nanocrystal core surface coordination (carboxylate moiety) remained the same. Thus, the present disclosure describes specific nanocrystal-containing materials and/or system design methods that enable enhancement of the nanocrystals', nanocrystal-containing materials', and/or nanocrystal-containing systems' broadband optical absorbances (up to a factor of two) and shift the absolute nanocrystal systems' band edge energy levels (by over 2.0 cV). The work function of the PbS-(cinnamic acid molecule ligand) systems is shown herein to be tunable between about 3.0 cV and about 5.4 cV, while maintaining the Fermi-level position within the nanocrystal bandgap, and was shown to correlate to the dipole moment of the ligand, as well as the amount of ligand bound to the surface of the nanocrystalline core. These nanocrystal design methods are supported by theoretical calculations, which provide guidance for designed material applications for use in next generation photovoltaic devices, light-emitting diodes (LEDs), and/or photodetectors.

Referring again to FIG. 1B, which illustrates a Janus-type nanoparticle 115, this kind of nanoparticle may be achieved by carefully selecting the starting ligands 130 and the exchange ligands 140 to have suitable physical properties, specifically the energy of exchange and the nearest-neighbor coupling energy between the ligands, and by completing the exchange method 200 described above in such a way that the starting ligand 130 cannot be completely exchanged by the exchange ligand 140. Such methods are described in more detail below. In short, a combined experimental and theoretical study was completed of ligand-ligand cooperativity during X-type carboxylate-to-carboxylate ligand exchange reactions on PbS nanocrystal surfaces. It was determined that the ligand dipole moment (varied through changing the substituents on the benzene ring of cinnamic acid derivatives) impacts the ligand-exchange isotherms; in particular, ligands with large electron withdrawing character result in a sharper transition from an oleate-dominated ligand shell to a cinnamate-dominated ligand shell. A two-dimensional lattice model was developed to simulate the ligand-exchange isotherms that accounts for the difference in ligand binding energies as well as ligand-ligand cooperativity. The model shows that ligands with larger ligand-ligand coupling energy exhibit sharper isotherms indicating an order-disorder phase transition. In addition, an anisotropic Janus ligand shell was synthesized by taking advantage of the ligand-ligand cooperative ligand exchanges. The Janus ligand shell was also monitored using $^{19}$F NMR showing that when the ligand-ligand coupling energy falls within the order region of the phase-diagram, Janus ligand shells can be constructed.

Figure 6:
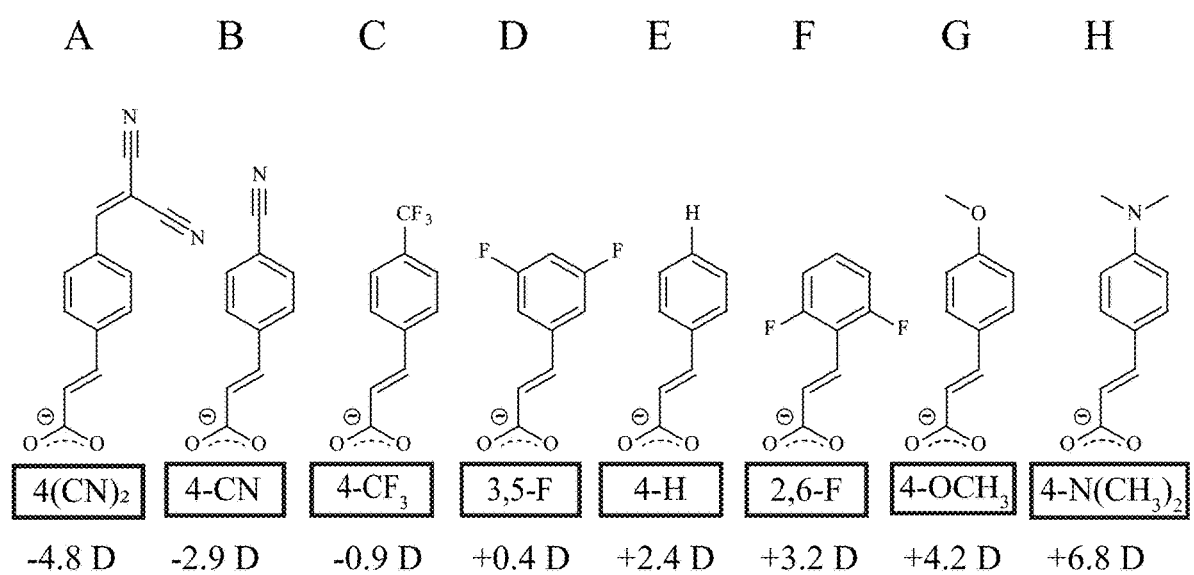
FIG. 6 illustrates functionalized cinnamic acids according to some embodiments of the present disclosure, along with their dipoles normal to the nanocrystal surface computed by DFT. The molecules are either electron donating (negative dipole) or electron withdrawing (positive dipole).

To begin, in-situ ligand exchange isotherms were studied using simple linear absorption spectroscopy. The realization that absorption enhancement acts as a simple feedback on the extent of exchange, allowing for the measurement of ligand exchange isotherms for ligands without easily distinguishable NMR peaks, enabled the study of the exchange of the oleate surface ligands with eight different functionalized cinnamic acids (R-CAHs, see FIG. 6) that are classified by their functional groups on the aromatic ring.

A custom 2-dimensional lattice model was developed that reproduces the salient features of the adsorption isotherms. The energy of exchange, $\Delta G_{exc}$, as well as a nearest-neighbor coupling energy between ligands, $\Delta J$, are outputs of the model. It was determined that the absolute magnitude of dipole moment of the cinnamic acid has a strong influence on the exchange energy, up to a few $k_BT$ for the largest dipoles used in this study. An interesting correlation was also observed between ligand dipole moment and the nearest neighbor coupling, $\Delta J$: ligands with large electron withdrawing character (negative dipole-moment) show much higher cooperativity, $\Delta J=-0.65\ k_BT$, than those with large electron donating character (positive dipole-moment), $\Delta J=-0.15\ k_BT$. These observations were used to design phase-segregated (e.g. patchy or Janus) ligand shells, which break the symmetry of an otherwise symmetrical nanocrystal.

3.2 nm diameter PbS nanocrystals were synthesized having a 1st excitation transition energy of 1.3 eV. They consisted of a stoichiometric PbS core with Pb-oleate ligands. The number of OA$^-$ ligands initially bound to each nanocrystal was measured to be 100±5 by quantitative $^1$H NMR, corresponding to 3.1 ligands/nm$^2$. This solution-phase ligand exchange procedure replaced the native oleate ligands with cinnamic acids to form cinnamate passivated PbS nanocrystals through a 1:1 X-type ligand exchange. Incoming free cinnamic acid transferred a proton to a surface bound oleate to form free oleic acid and surface bound cinnamate. Adding excess cinnamic acid drove the exchange towards completion.

Figure 7A:
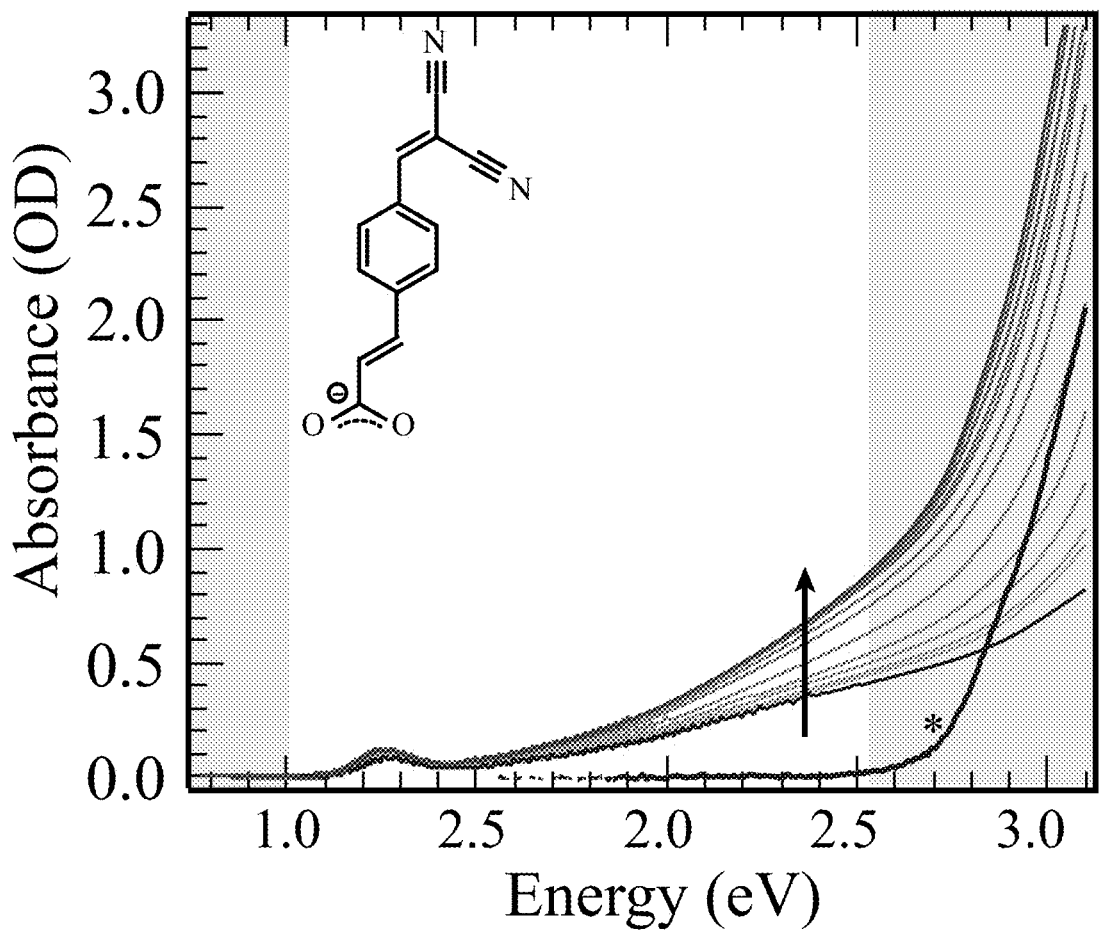
FIGS. 7A and 7B illustrate spectrophotometric titrations, according to some embodiments of the present disclosure.
Figure 7B:
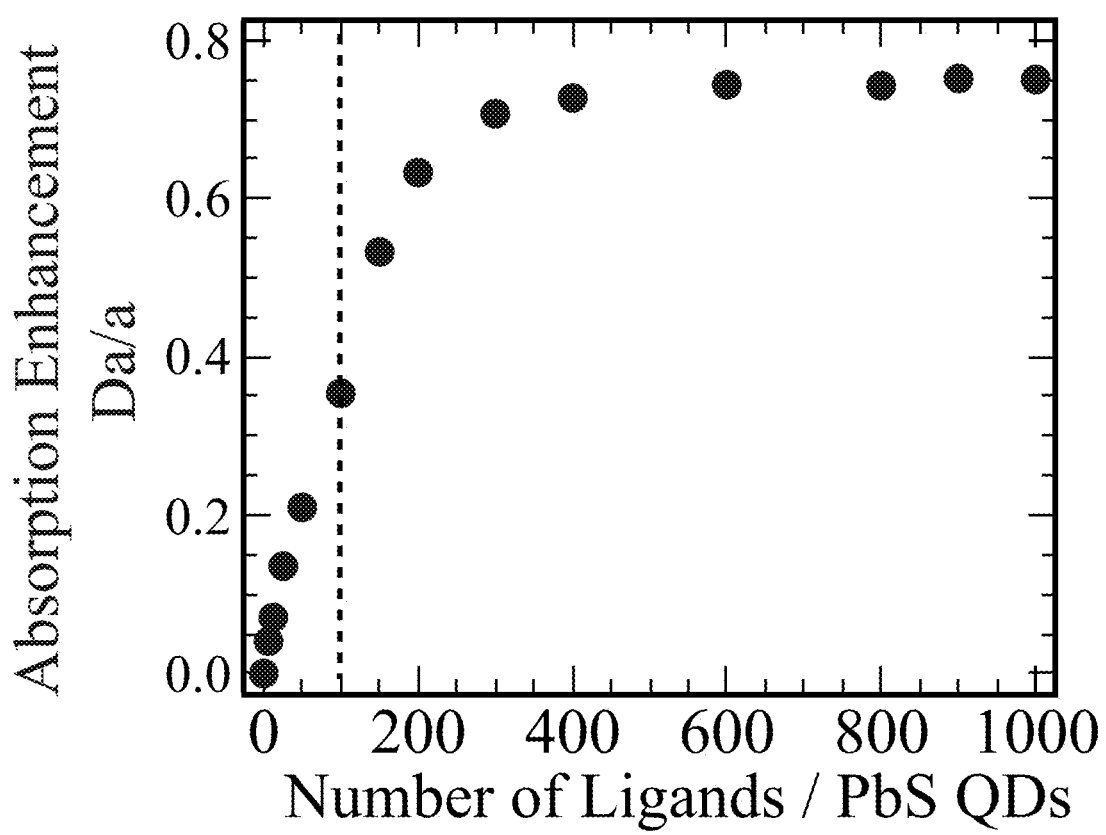
Figure 8A:
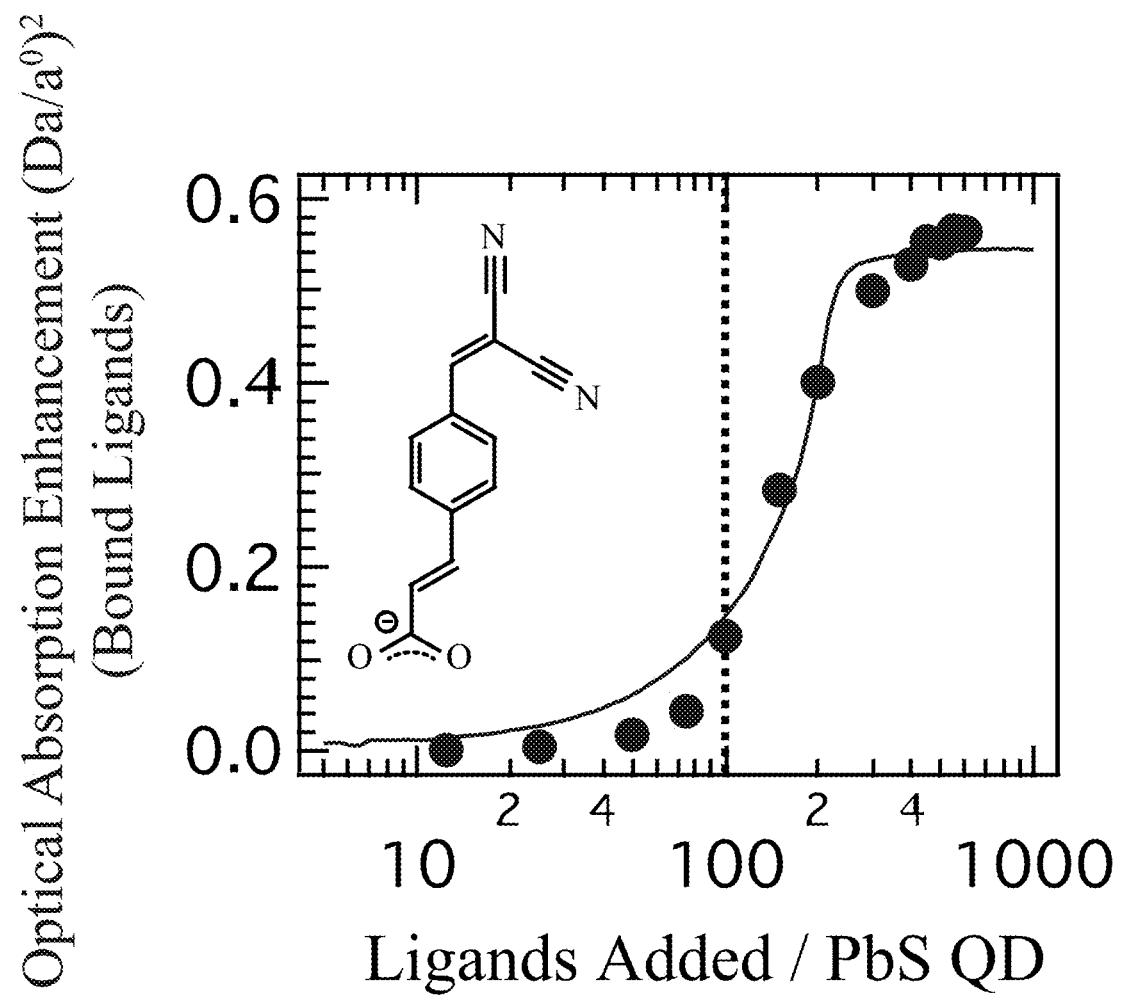
FIGS. 8A-8H illustrate adsorption isotherms (bound CA-ligands vs. free-ligands) of the ligand exchange reactions constructed from the quantitative spectrophotometric titrations, according to some embodiments of the present disclosure. The number of bound ligands is proportional to the $(\Delta\alpha/\alpha)^2$. Data are represented by filled circles and the solid lines are the best-fit lines obtained from a non-linear least-squares fitting of a spin-lattice simulation. The best-fit parameters are displayed in FIGS. 14A and 14B. The dashed line corresponds to the number of binding sites available. The x-axis is the number of ligand equivalents added during the experiment.
Figure 8B:
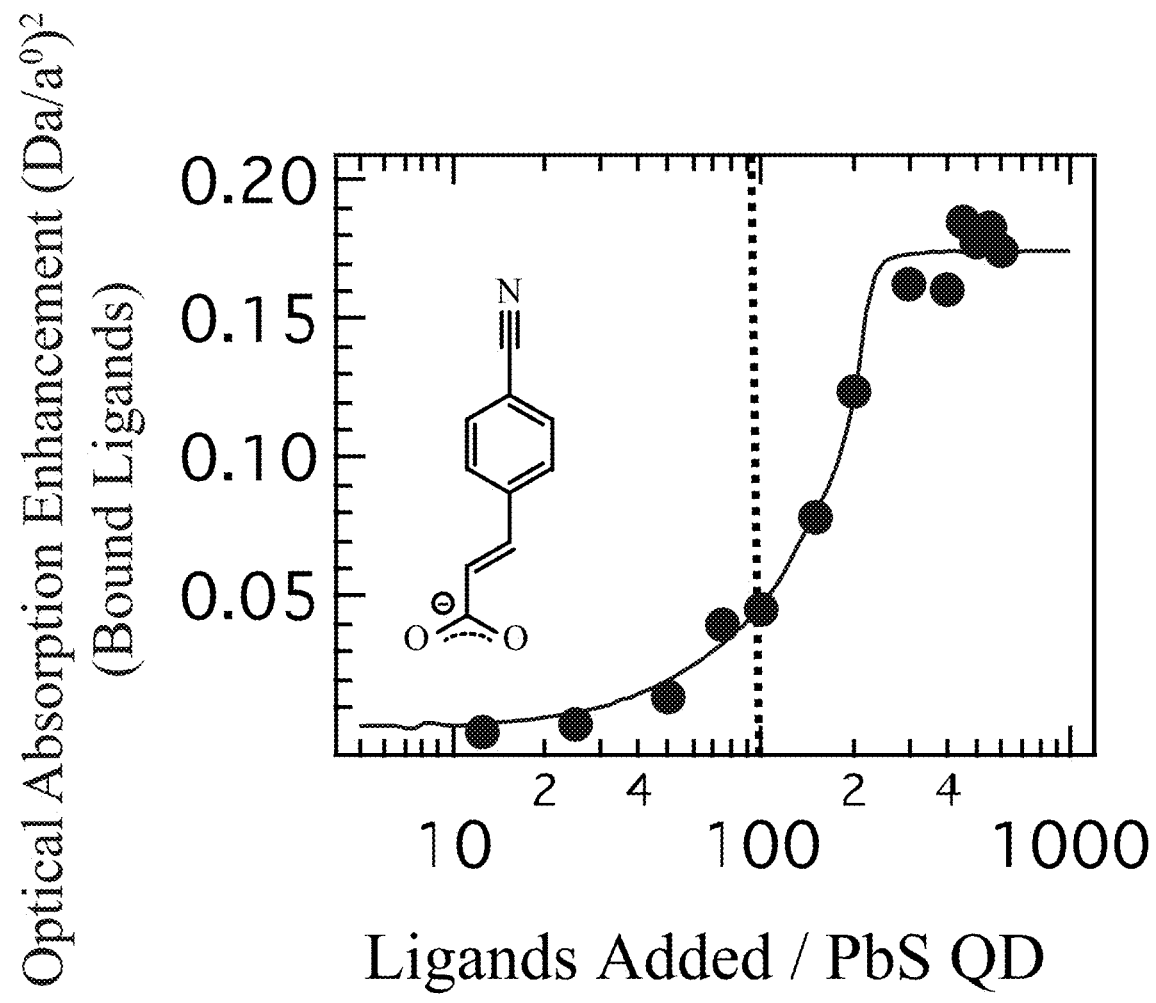
Figure 8C:
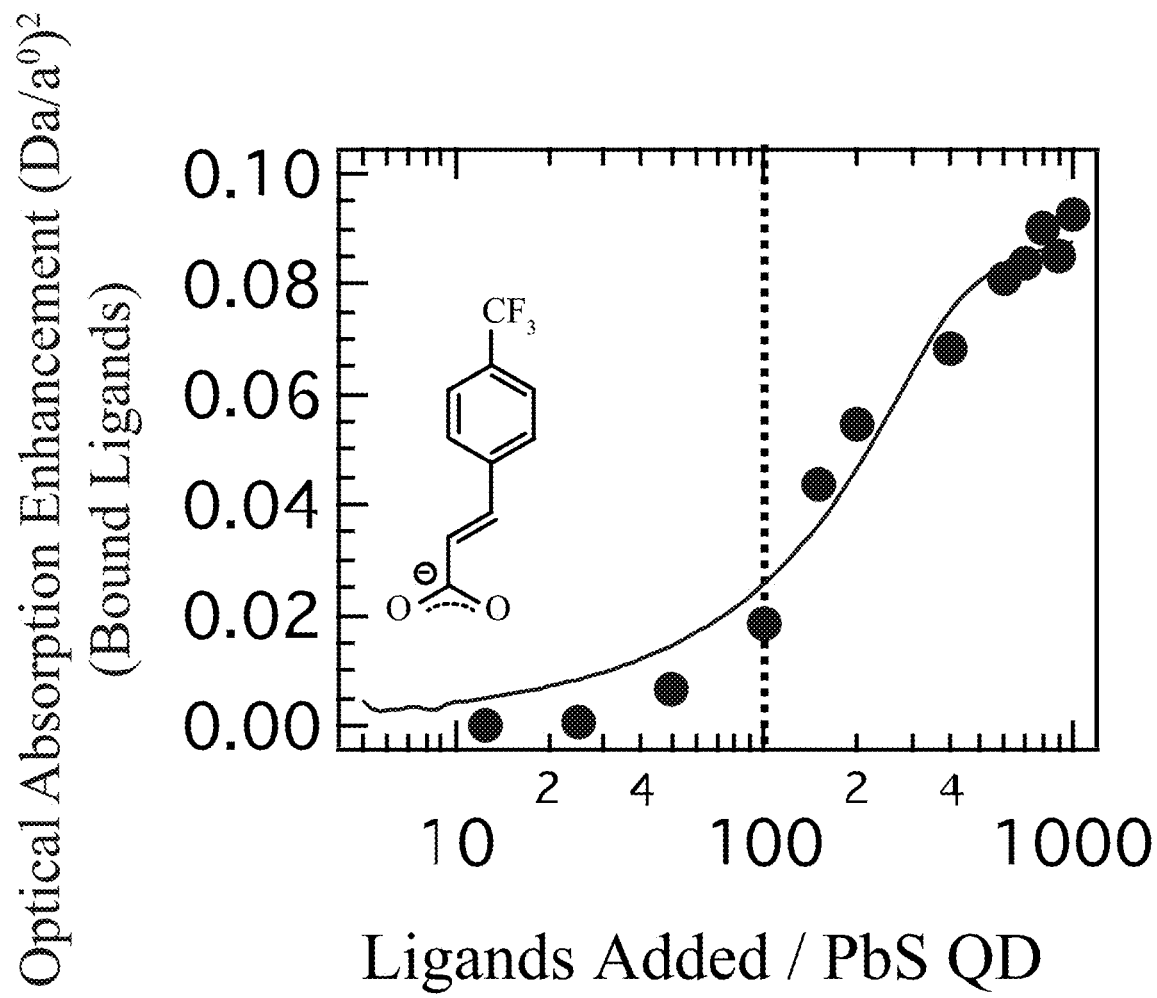
Figure 8D:
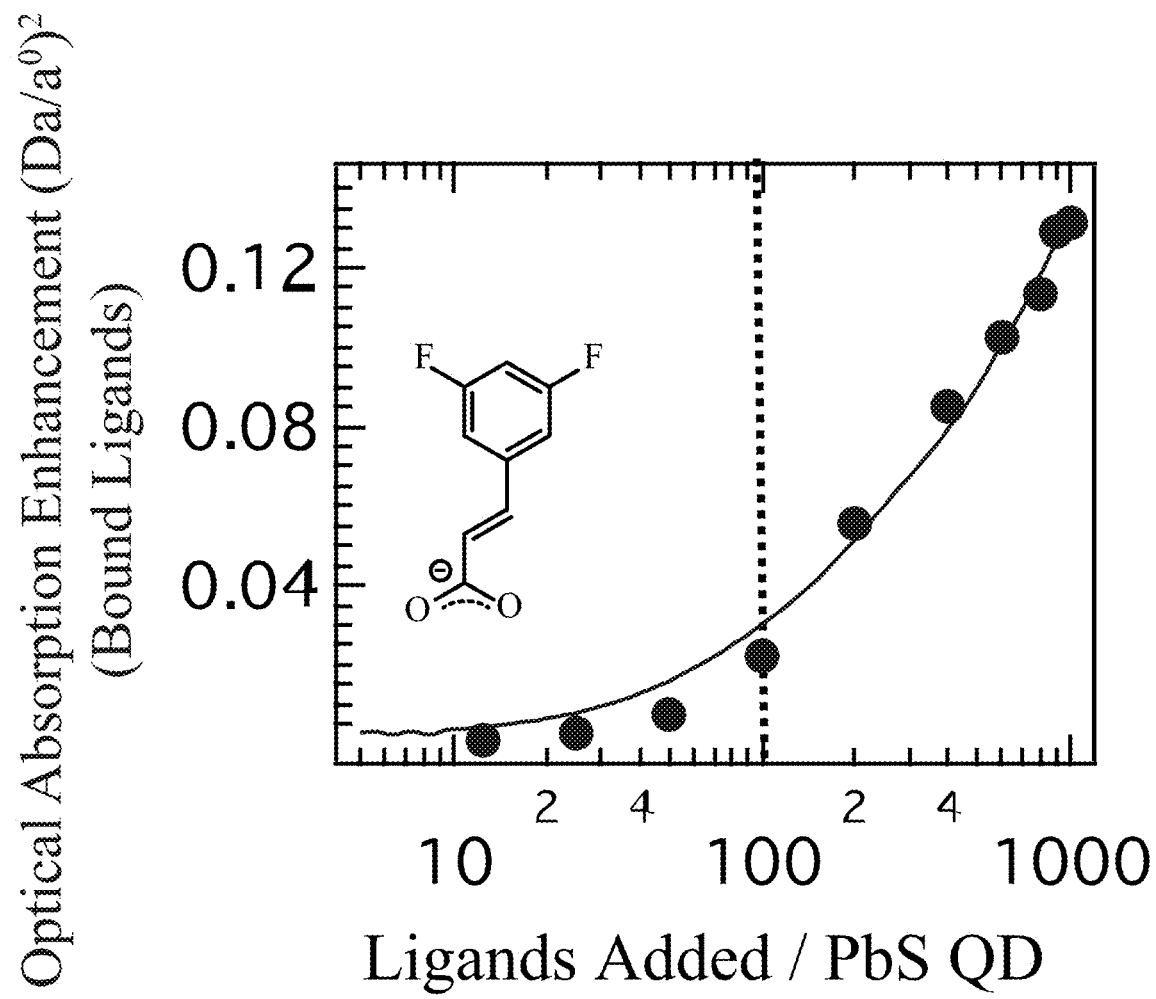
Figure 8E:
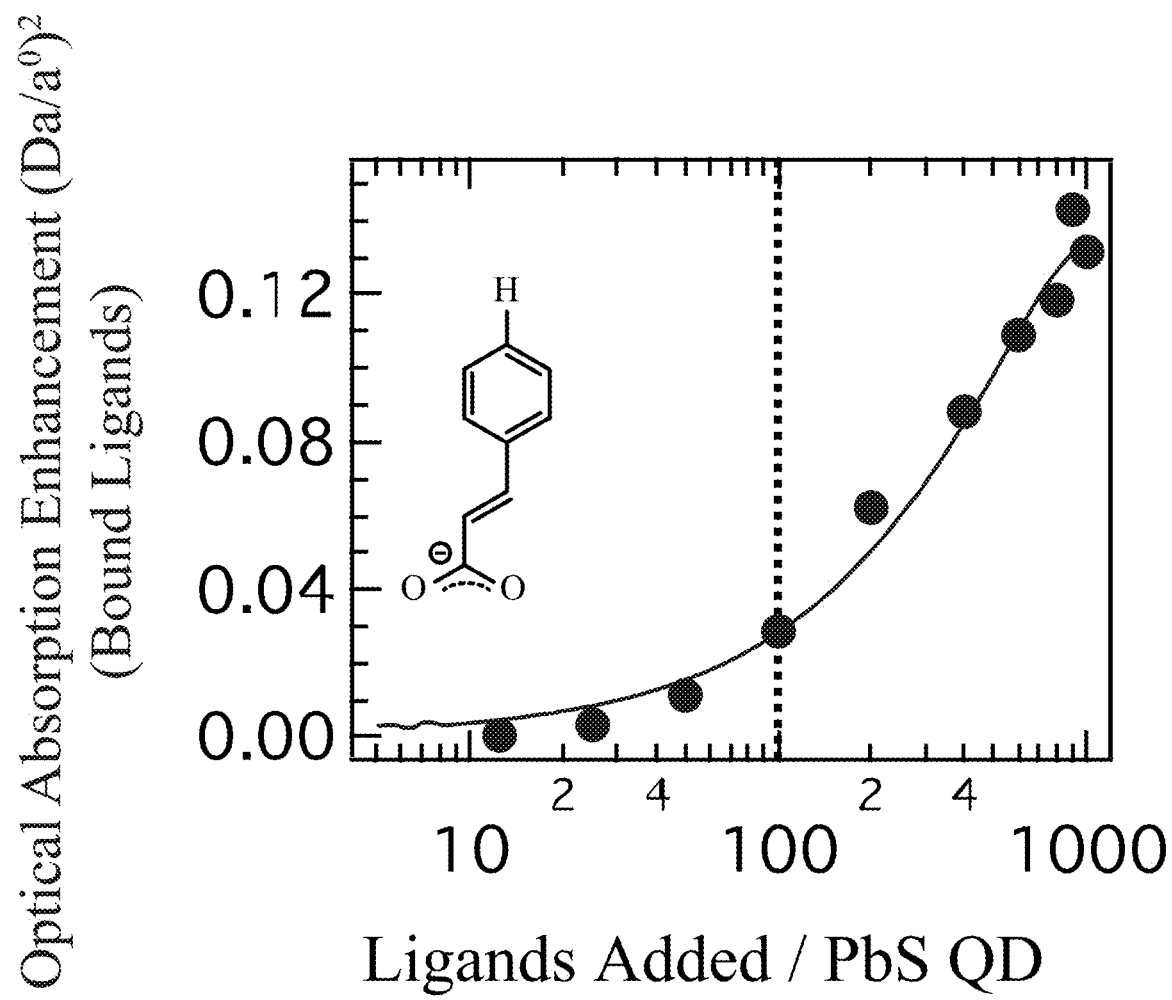
Figure 8F:
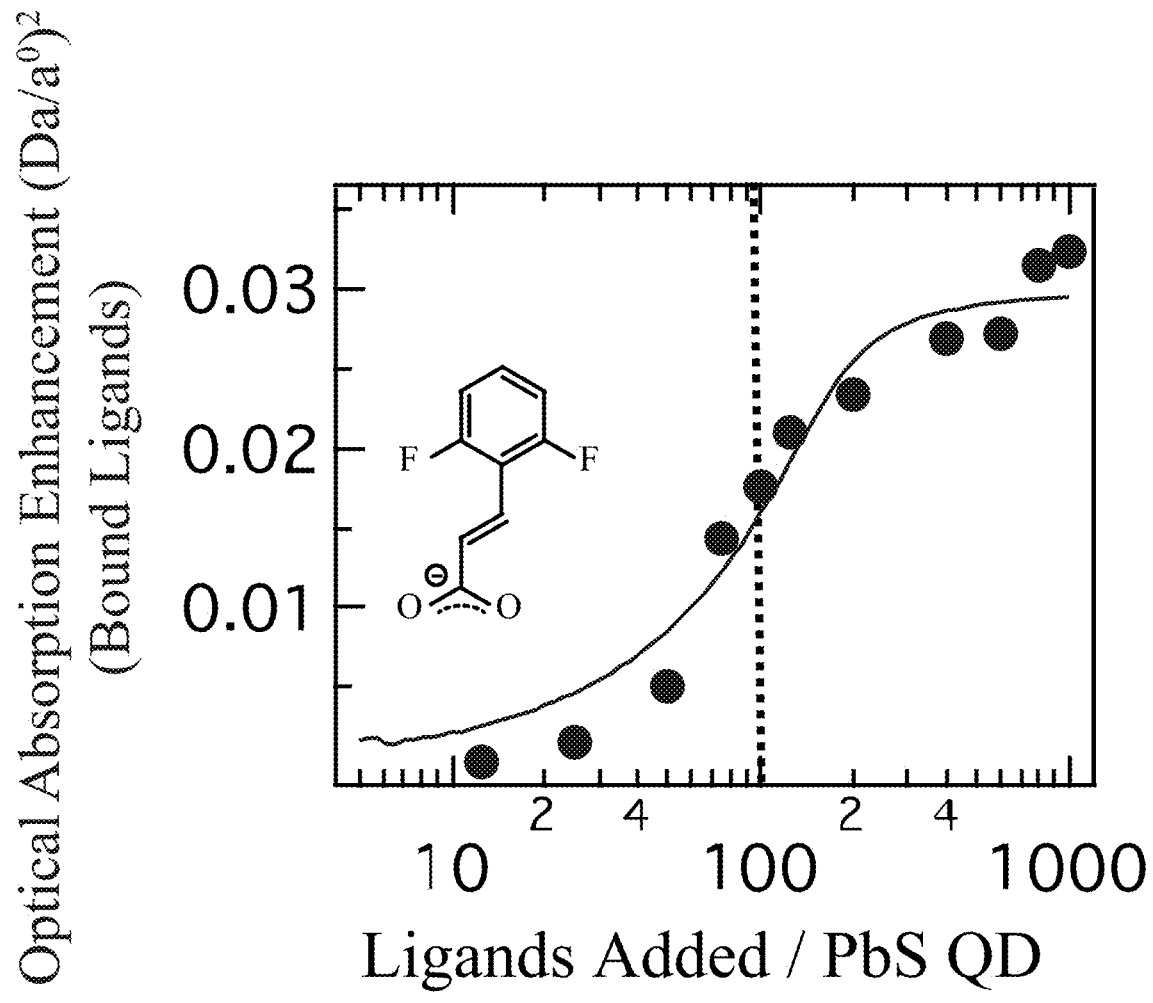
Figure 8G:
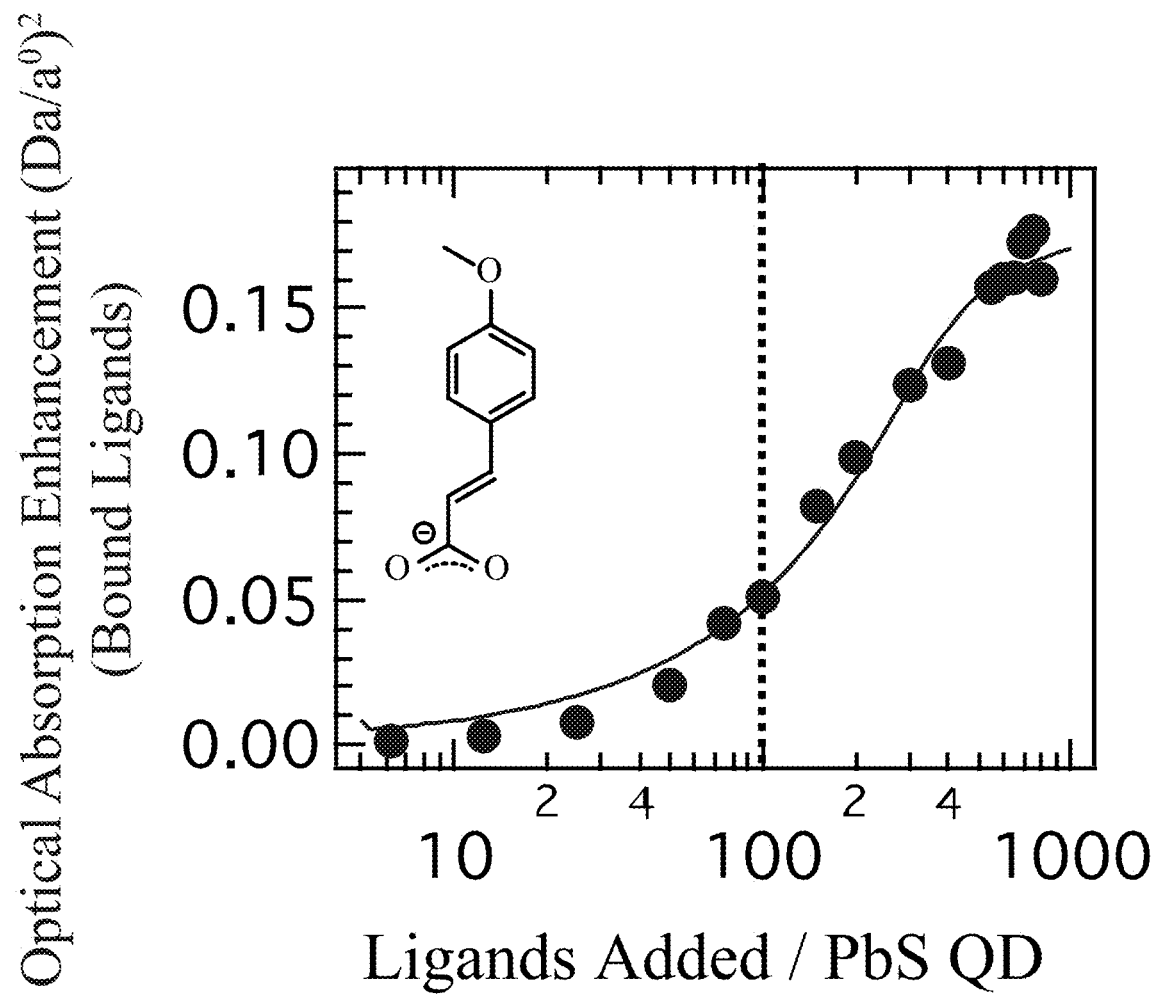
Figure 8H:
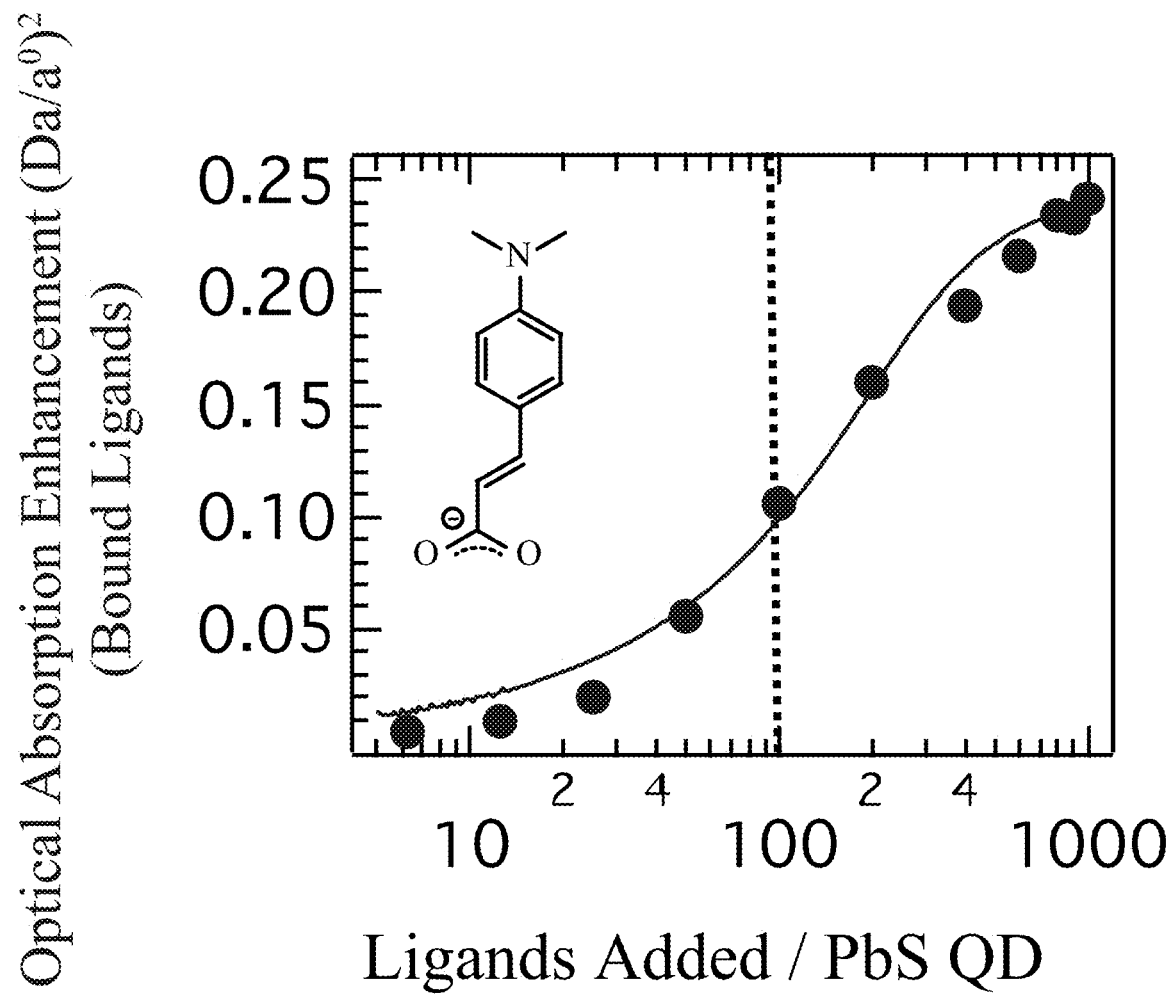

For each of the functionalized cinnamic acids (see FIG. 6), quantitative spectrophotometric titrations were performed (see FIGS. 7A and 7B). The absorption enhancement was correlated to the square root of number of bound ligands (see below). Thus, to construct the adsorption isotherms (bound-ligands, R-CA$^-$, vs added free-ligands) $(\Delta\alpha/\alpha_0)^2$ was plotted versus the number of free-ligand equivalents, where $\Delta\alpha$ is $(\alpha-\alpha_0)$, $\alpha_0$ is the integration of the as-synthesized OA$^-$/nanocrystal absorbance spectrum, and a is the integration of the in-situ nanocrystal spectrum (see FIGS. 8A-8H for each of the ligands shown in FIG. 6).

A 2D lattice model was developed and used to perform a Monte-Carlo simulation of the ligand exchange reactions at nanocrystal surfaces in solution. The simulations employed a square n×n binary lattice, where n*n=$N_{sites}$ with periodic boundary conditions to simulate the spherical nanocrystal (NC) surfaces. These simulations differ from traditional 2D lattice simulations in one key way: a finite number of added ligands ($N_{add}$) was considered, originally bound ligands ($\theta*N_{sites}$), and binding sites ($N_{sites}$), where $\theta$ is the fraction of all binding sites occupied by the original ligands. For each binding site occupied by the original ligand (ligand A), a probability ($P_{AB}$) of exchanging ligand A for ligand B was defined. While for each binding site that becomes occupied with the new ligand (ligand B), the probability ($P_{BA}$) for the reverse reaction was defined (e.g., the freed oleic acid can replace the newly bound cinnamates). The probabilities are a product of a Boltzman factor, $B_f$, and a factor that accounts for the fraction of ligands in solution with the identity of a new or incoming ligand ($f_B$ when the incoming ligand has identity B, and $f_A$ when the incoming ligand has identity A). Thus, $$f_A(\theta, N_{add}) = \frac{\theta * N_{sites}}{N_{add} + N_{sites}}, \tag{1}$$

$$f_B(\theta, N_{add}) = \frac{N_{add} - \theta * N_{sites}}{N_{add} + N_{sites}}, \tag{2}$$

The free energy of ligand exchange, $\Delta G_{exc}$ is the difference in binding free energy between ligand B and A; $NN_B$ is defined as the number of nearest ligand B neighbors and $\Delta G_{MF}$ is a mean-field free energy difference between ligands of type B and type A when bound to the surface. The nearest neighbor ligand-ligand coupling energy is $\Delta J$, and the total number of nearest neighbors is 4 (i.e., using a square lattice) thus $NN_A+NN_B=4$. Then the exchange energy $\Delta G_{AB}$ associated with replacing a ligand of type A with a ligand of type B is $$\Delta G_{AB} = \Delta G_{exc} + \theta \Delta G_{MF} + 4\Delta J(2-NN_B) \tag{3}$$

Similarly, the energy $\Delta G_{BA}$ of replacing a ligand of type B with a ligand of type A is simply the negative of expression (3). The Boltzman factor is thus:

$$B_f^{AB} = \begin{cases} \exp(-\Delta G_{AB}/k_BT) & \text{if } \Delta G_{AB} > 0 \\ 1 & \text{if } \Delta G_{AB} \leq 0 \end{cases}, \tag{4}$$

and the probability of exchange is $P_{AB}=B_f^{AB}*f_A(\theta,N_{add})$, and $P_{BA}$ is defined similarly. $P_{AB}$ and $P_{BA}$ Were used as defined above to carry out Monte Carlo simulations. At the beginning of each simulation, all binding sites are initially occupied by ligand A. The simulation progressed by randomly selecting a grid point (each grid point is associated to a ligand site) and computing the probability $P_{AB}$ of changing the grid point occupancy from ligand A to ligand B or when the site is occupied by B, the probability of exchanging B for A, $P_{BA}$. If $P_{AB}$ Or $P_{BA}$ is larger than a random number between 0 and 1 the exchange occurs, otherwise it does not occur. This random sampling was repeated a large number of times (between 106 and 109) to collect sufficient statistics on the extent of exchanges between ligands. The simulation was run for a wide range of different Nada values to create isotherms of coverage versus ligand addition. To model the measured adsorption isotherms non-linear least squares fitting was used (see the solid-traces FIGS. 8A-8H) to find the computed isotherm with best-fit parameters $\Delta G_{exc}$, $\Delta G_{MF}$ and $\Delta J$. The model reproduces the trends in the data fairly well, however, at the low and high exchanges the model deviated from the data. When setting the mean-field term $\Delta G_{MF}$ to zero, the resulting best-fit values changed in a negligible way.

Figure 9:
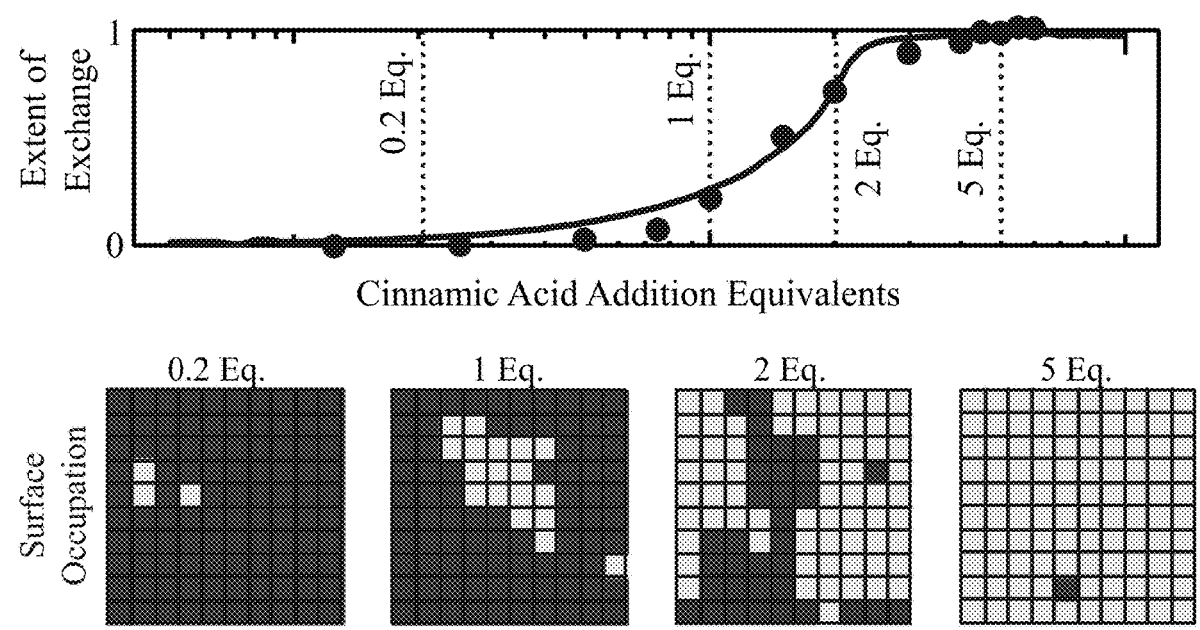
FIG. 9 illustrates the isotherm for 4(CN)$_2$-CAH exchanging with oleic acid, according to some embodiments of the present disclosure. The solid circles are the measured optical absorption values, scaled with the square root dependence, and the solid line is the simulated isotherm. The four square-lattice images show representative surface coverage patterns at equilibrium for four different ligand addition equivalents. The clustering of ligands with their own type clearly indicates strong nearest neighbor interactions.

The lower panels of FIG. 9 illustrate snapshots of a representative Monte Carlo simulation of the ligand exchange titrations when the ligand-ligand coupling energy is less than $-0.44\ k_BT$ (vida infra). At low additional equivalents (referring to the left box) the ligand shell is primarily oleate (ligand A, dark boxes). When the ligand concentration reaches one equivalent, the ligand exchange reaction starts and the cinnamates (ligand B, lighter shaded boxes) tend to group together (they form patches) because of the ligand-ligand cooperativity. Around two additional equivalents the ligand shell is roughly 50/50 and the ligands are completely segregated.

Figure 10A:
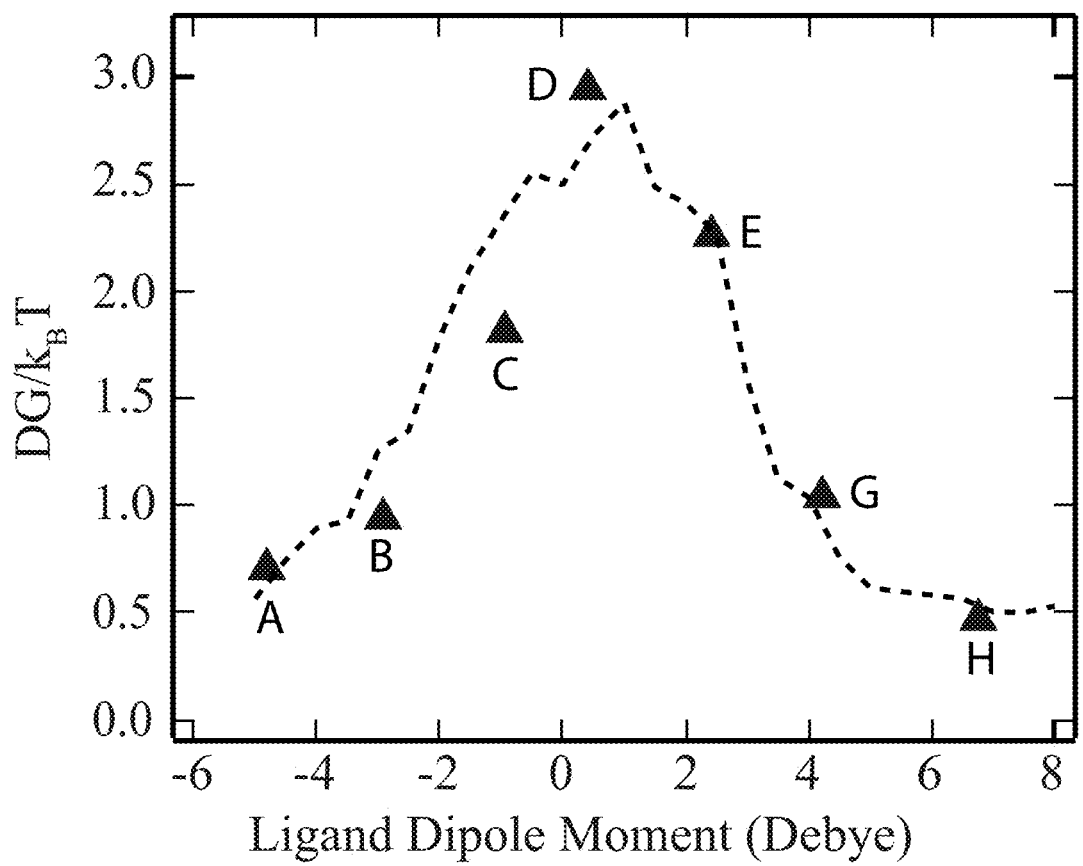
FIGS. 10A and 10B illustrate parameters of the 2D lattice simulation for ligand exchange, according to some embodiments of the present disclosure.
Figure 10B:
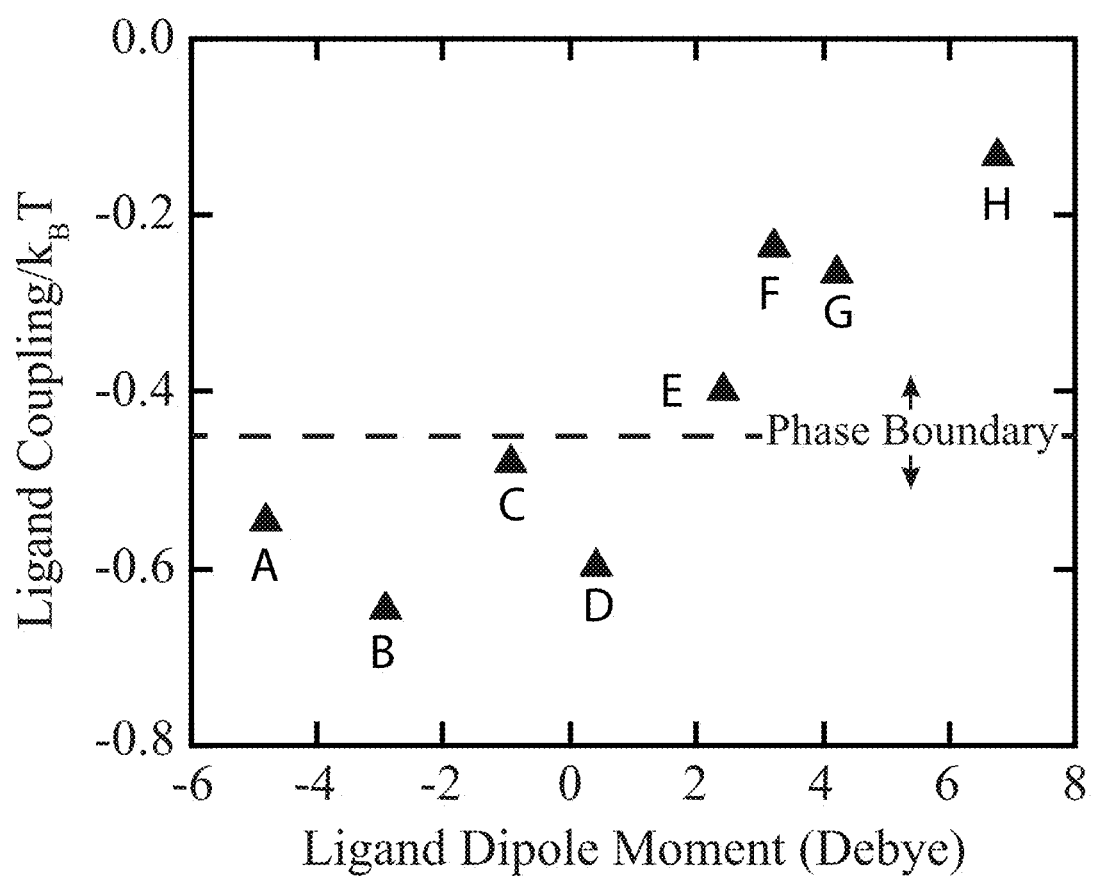
Figure 11:
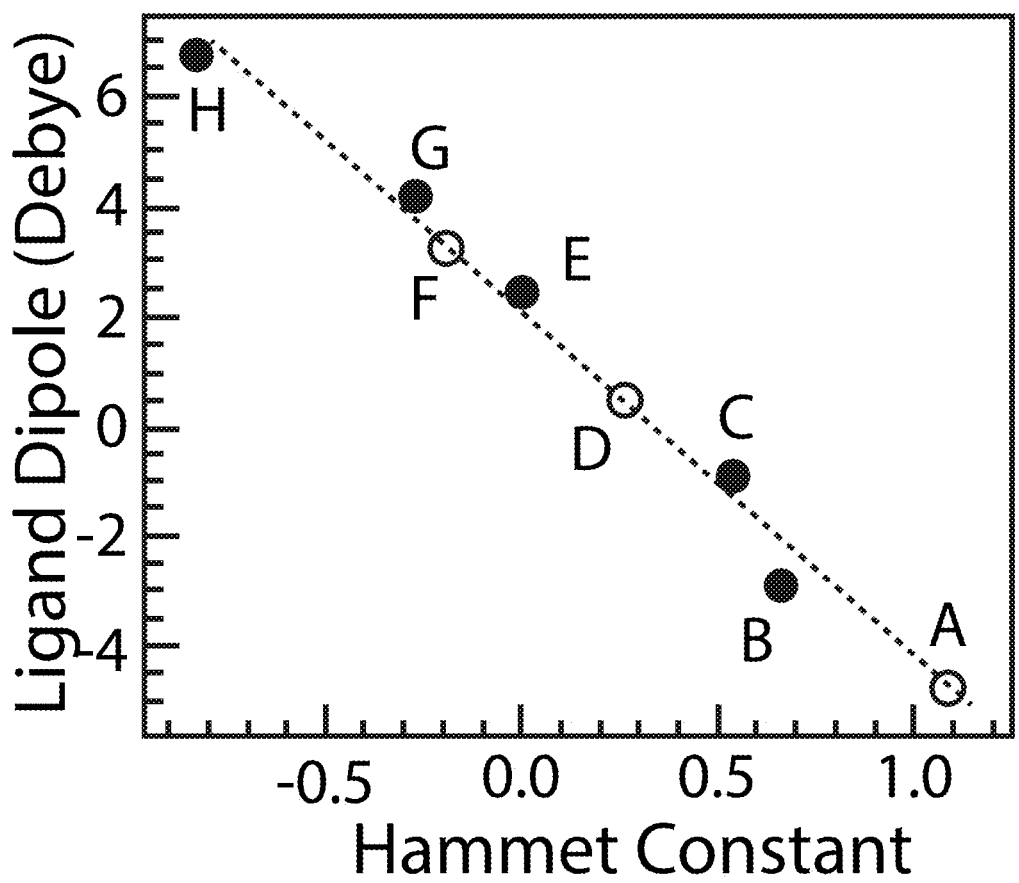
FIG. 11 illustrates the relationship between calculated R-CAH ligand dipole and the corresponding tabulated Hammett Constant, according to some embodiments of the present disclosure. The solid circles represent ligands with functional groups that have tabulated Hammett Constants, and the dashed line is a fit to this data. The open circles represent ligands with extrapolated Hammett Constants based on calculated dipole moments. The letters indicate the cinnamic acid as labeled in FIG. 6.

The resulting model outputs (fitted parameters), $\Delta G_{exc}$ and $\Delta J$, were plotted against the ligand-dipole computed using DFT calculations (see FIGS. 10A and 10B). The computed dipole moments are linearly related to the tabulated Hammet parameters (see FIG. 11). It is important to note that $\Delta G_{exc}$ and $\Delta J$ do not represent the binding free energy and nearest neighbor interactions separately. Instead, $\Delta J$ contains only the change in nearest neighbor interaction that does not contribute to the total free energy of exchange. Any component of the nearest neighbor coupling that does contribute to total binding free energy is included in $\Delta G_{exc}$. This can be understood as follows: the total energy for exchanging all of ligand A with all ligand B on a nanocrystal surface is a sum of all individual ligand exchanges, i.e., $\Delta G_{tot} = \Sigma \Delta G_{AB}$. Since the lattice model used here is isomorphic with the Ising Model, and the site-to-site coupling energy in the Ising model is symmetric, the coupling term is equal for A-A and B-B interactions. In the sum $\Sigma \Delta G_{AB}$ the coupling terms cancel since the coupling energy is the same for A-A and B-B interactions. However, for intermediate exchanges this is not the case since it takes a coupling energy $\Delta J$ to break or form A-A interactions.

Thus, this term represents the differences in nearest neighbor coupling free energy between the oleate ligands and the cinnamate ligands that drive the cooperative ligand exchange. Larger negative values cause the ligand exchange isotherm to exhibit a sharper transition from all-oleate coverage at low ligand addition to all-cinnamate coverage at high ligand addition. This can be clearly seen for the $4CN_2$ and 4CN species (see FIGS. 8A and 8B) compared to the $4OCH_3$ and $N(CH_3)_2$ (see FIGS. 8G and 8H), and in the clustering evident in the surface coverage graphs for the $4(CN)_2$ exchange depicted in the bottom row of FIG. 9. With this in mind, one can interpret the behavior of $\Delta G_{exc}$ as a function of the ligand-dipole (see FIG. 10A). For values of the dipole moment close to zero, the $\Delta G_{exc}$ is maximum at $\sim +2\text{-}3\ k_BT$.

However, as the cinnamic acid dipole increases, the polarization of the nanocrystal surface and ligand shell acts to stabilize the molecular dipole, working against the acidity-driven binding enthalpy difference. As the absolute magnitude of the dipole moment increases, $\Delta G_{exc}$ is reduced to $\sim 0.7\text{-}0.8\ k_BT$.

To account for this reduction, three contributions may be considered: a dipole-dipole interaction energy for dipoles oriented perpendicular to the NC surface, $W_e^{vert}$, a dipole-diple interaction energy for dipoles oriented parallel to the NC surface, $W_e^{planar}$, and a term $\Delta G_0$ that represents the difference in binding free energy based on the different binding groups (cinnamate vs. oleate); thus, $\Delta G_{exc} = W_e^{vert} + W_e^{planar} + \Delta G_0$. The variations in pKa within the cinnamic acid derivatives ($pK_a \sim 4$) is much less than the difference in pKa between cinnamic acid and oleic acid ($pK_a \sim 10$), i.e., oleic acid is a much weaker acid than are the cinnamic acids. Thus, oleic acid binds lead cations much more strongly than cinnamic acid does, overwhelming any energetic difference based on proton transfer and causing oleate to bind $\sim 2.5\ k_BT$ more favorably than the cinnamic acid with near-zero dipole (35F-CAH).

Furthermore, if the variations in acidity across the ligand library were to dominate the binding energy, one would expect $\Delta G_{exc}$ to vary linearly with dipole moment (or Hammet parameter) rather than showing the observed dependence. For these reasons one can expect $\Delta G_0$ not to vary across the family of cinnamic ligands.

Figure 10C:
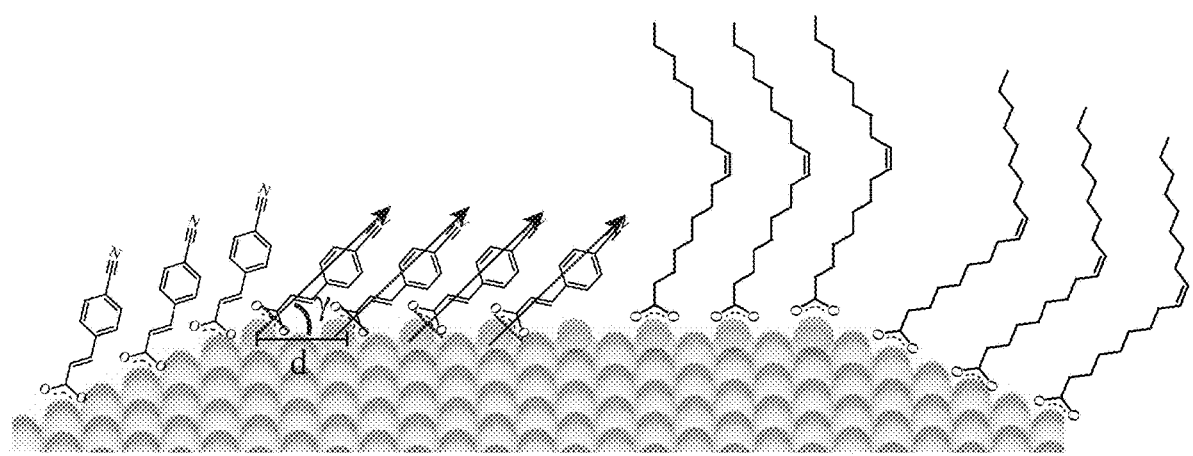
FIG. 10C illustrates a cartoon depiction of the dipoles and tilt angle (measured from the nanocrystal surface) considered in the interaction energy between ligand dipoles at the surface of nanocrystals, according to some embodiments of the present disclosure.
Figure 12:
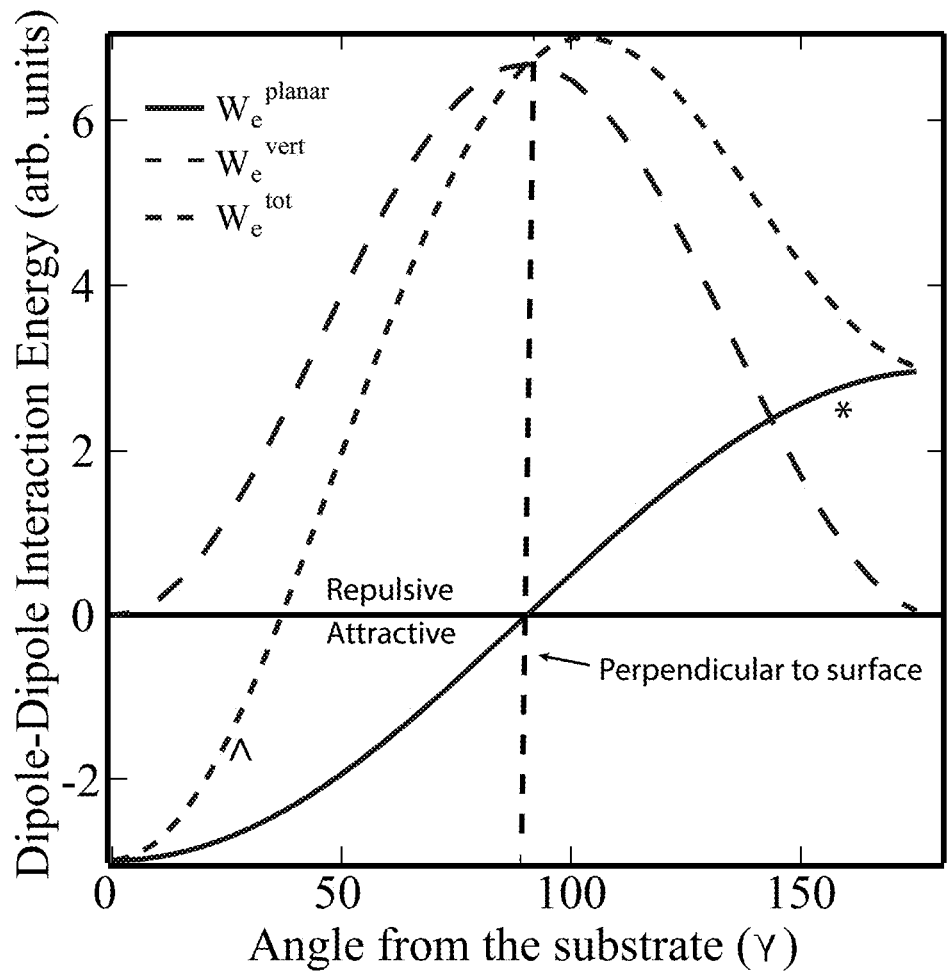
FIG. 12 illustrates a plot of dipole-dipole interaction energy as a function of angle from the substrate, according to some embodiments of the present disclosure. *=head-to-head; —=head-to-tail.
Figure 13:
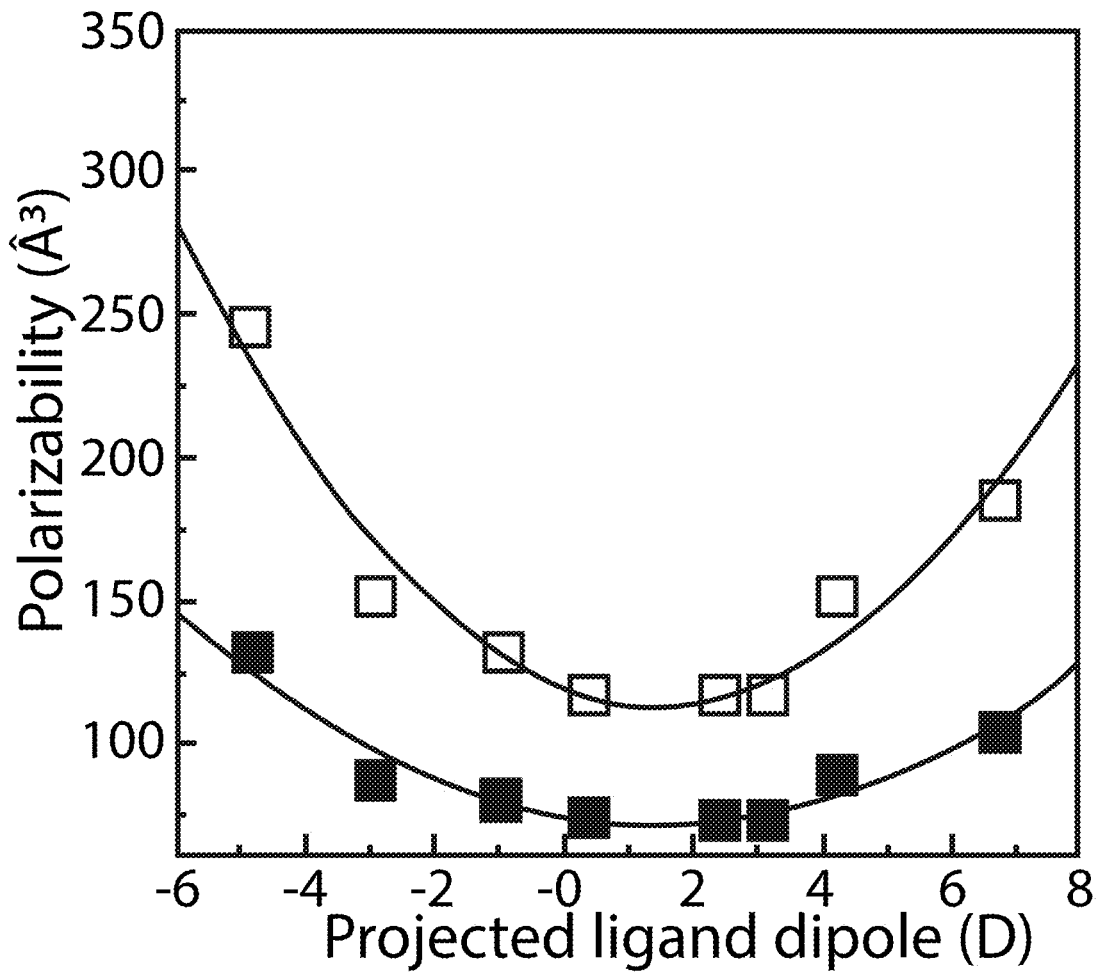
FIG. 13 illustrates the quadratic behavior of the polarizability as a function of the dipole moment for the series of cinnamic acids used in this study, according to some embodiments of the present disclosure. The filled squares are the isotropic polarizability (⅓ of the trace of the polarizability tensor) and the hollow squares are the polarizability tensor projected onto the ligand's long axis.

Both electrostatic terms, $W_e^{vert}$ and $W_e^{planar}$, are proportional to the magnitude of the dipole moment squared ($\mu^2$). However, $W_e^{vert}$ is purley repulsive and scales as $\sin(\gamma)/d^3$ where d is the distance between ligands, and $\gamma$ is the angle formed by the ligand with the substrate (when $\gamma=0$ the ligands are laying flat on the surface). $W_e^{planar}$ can either be repulsive or attractive depending on whether the ligands tilt together forming a head-to-tail alignment or tilt into each other forming a head-to-head alignment. It is assumed herein that the ligands tilt together (see FIG. 10C) and thus the interaction parallel to surface is attractive (see FIG. 12). When $\gamma$ is less than 45°, $|W_e^{planar}| > |W_e^{vert}|$, and the total interaction energy is attractive. One can estimate the angle the dipolar ligands formed with the surface normal because the dipolar ligands cause the band edges of the nanocrystalline films to shift by up to 2 eV. The shift of the band edges ($\Delta \phi$) is related to the magnitude of the ligand-dipole, $\mu$, and the ligand tilt angle $\gamma$: $\Delta \phi = \mu \cos(90-\gamma)/(\varepsilon d^2)$. The dielectric constant of the ligand monolayer, $\varepsilon$, is calculated accounting for cooperative effects (see below). It was determined that the ligands are likely tilted by a range between about 70 and about 40 degrees from the direction normal to the surface (see below for estimation) so $\gamma$ varies between about 20 degrees and about 50 degrees. Using these angles as starting values, both the attractive and repulsive terms were determined, (see below) and a general agreement between the calculation was determined (see dashed line of FIG. 10A) and our data (triangle of FIG. 10A) with slightly adjusted tilt angles (see FIG. 13).

Figure 14A:
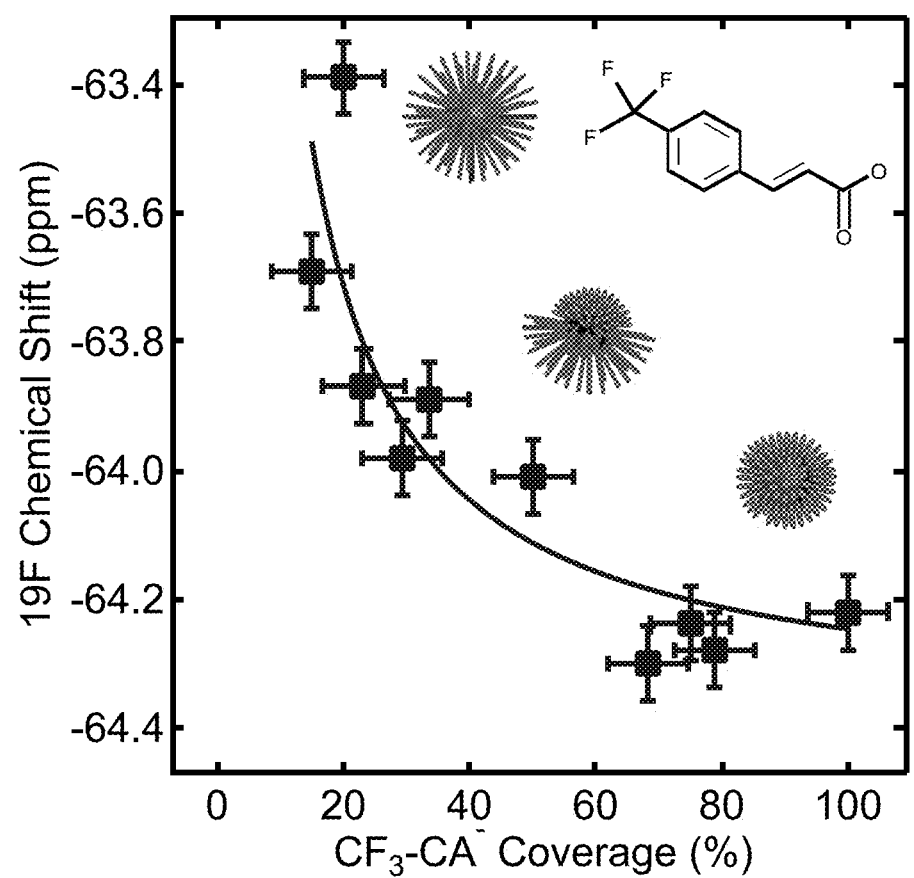
FIGS. 14A-14D illustrate experimental data, according to some embodiments of the present disclosure.
Figure 14B:
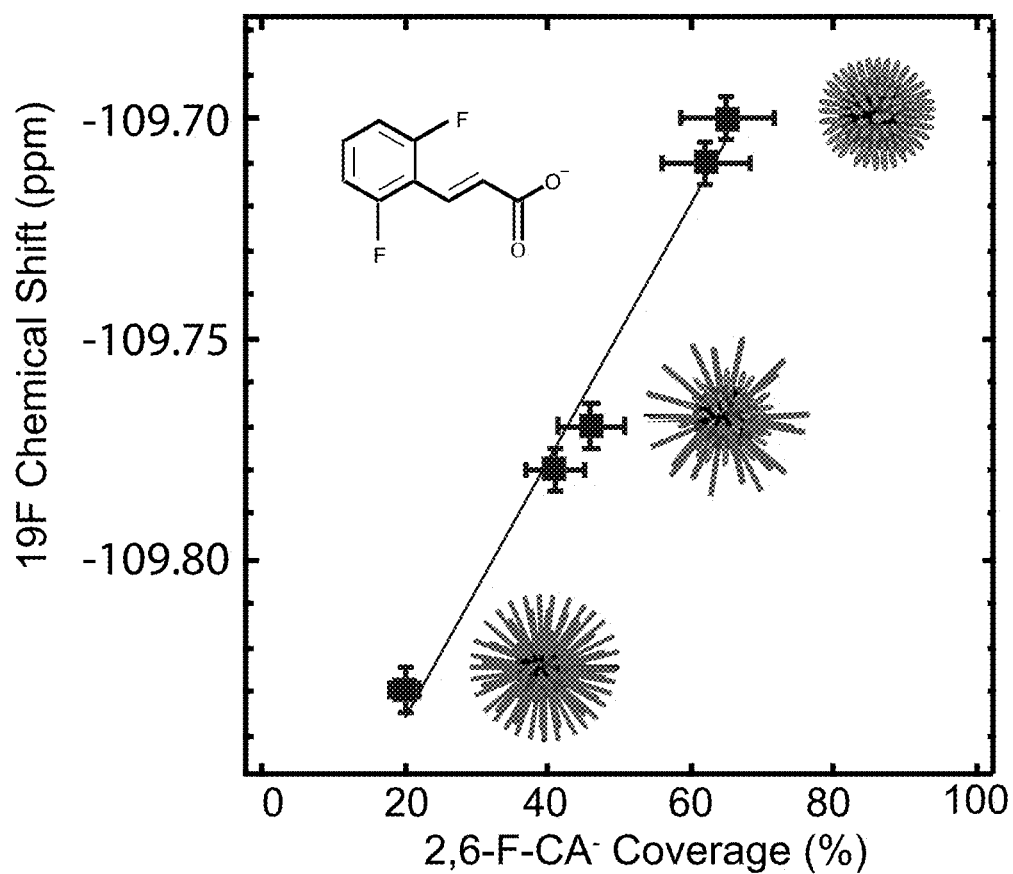

A correlation was also found between the nearest neighbor coupling ($\Delta J$) and the ligand dipole moment (see FIG. 14B). There is a consistent trend in $\Delta J$ versus the ligand dipole, with the most electron withdrawing species having the largest negative $\Delta J$. As the ligand dipole changes from negative to positive, the $\Delta J$ reduces in magnitude, approaching zero.

Figure 15:
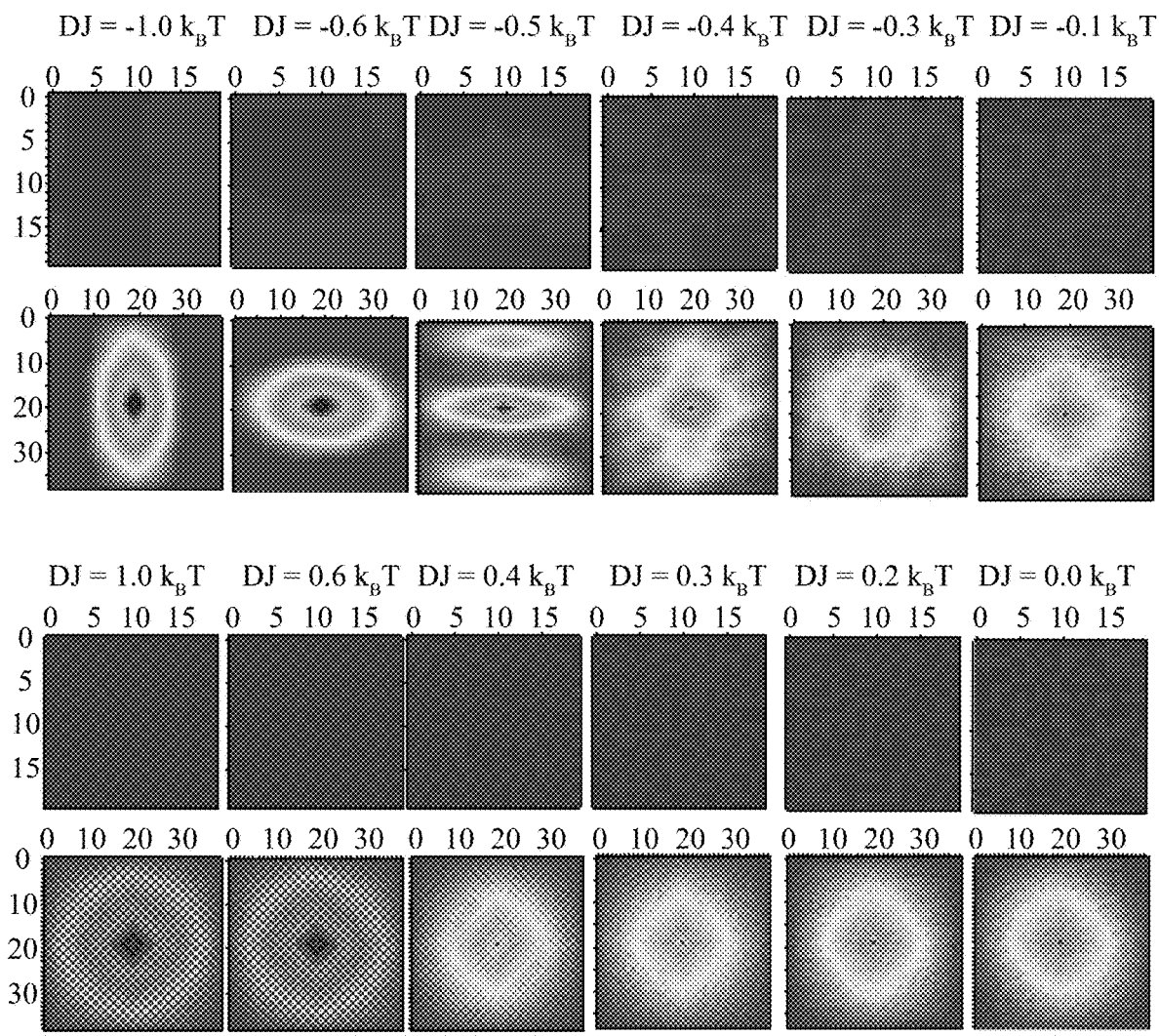
FIG. 15 illustrates configurations at 50% ligand exchange (top) and corresponding correlation functions (bottom) for coupling energies varying from −1 to 1 k$_B$T, according to some embodiments of the present disclosure. When the coupling energy is less than −0.44 k$_B$T a phase transition occurs (top row) corresponding to phase segregation of the ligands. When the coupling energy is greater than 0.44 k$_B$T the anti-correlated phase transition occurs (bottom row).
Figure 16A:
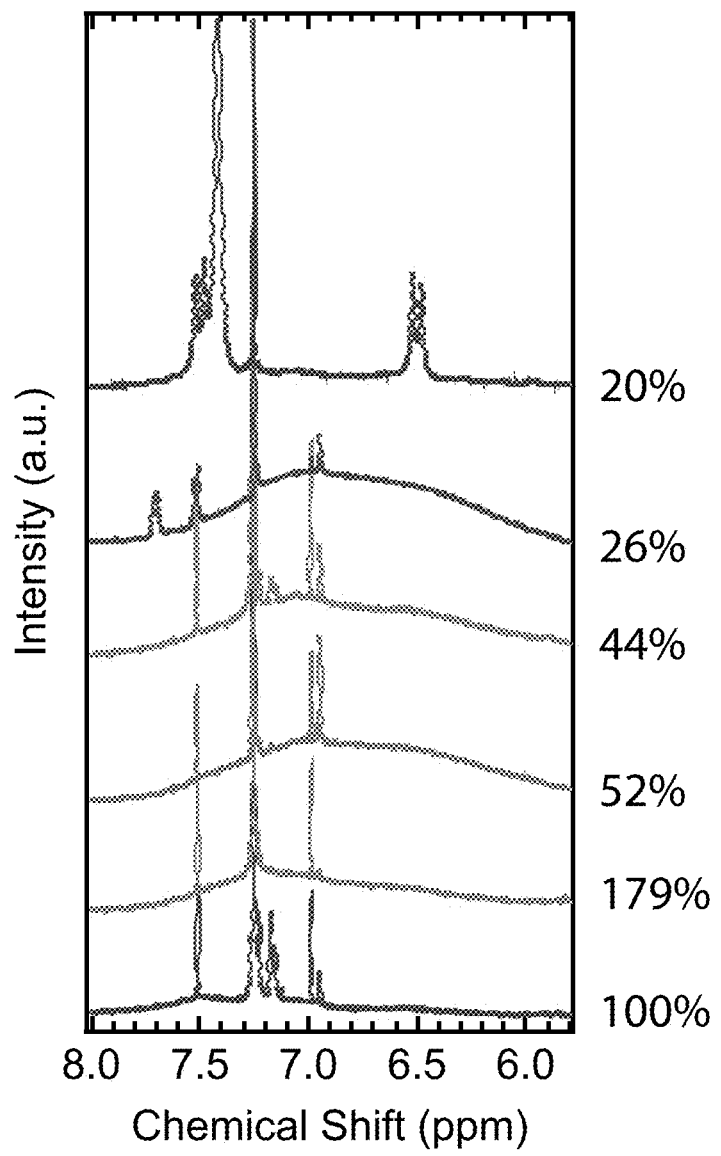
FIGS. 16A-16D illustrate experimental data, according to some embodiments of the present disclosure.
Figure 16B:
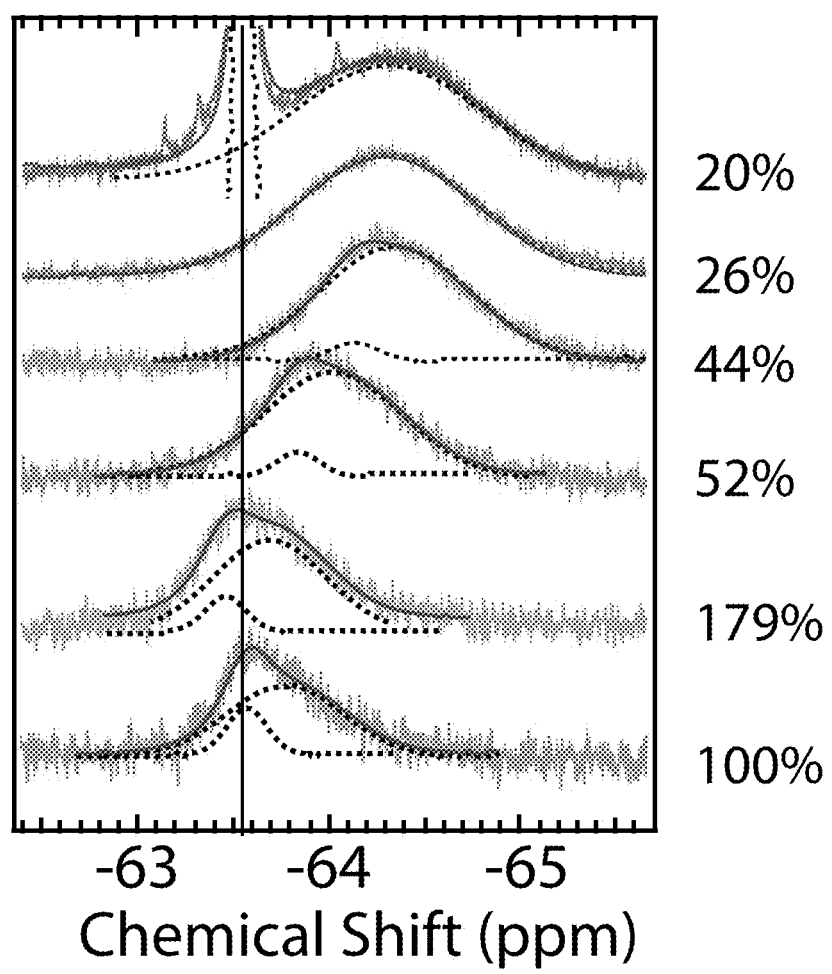
Figure 16C:
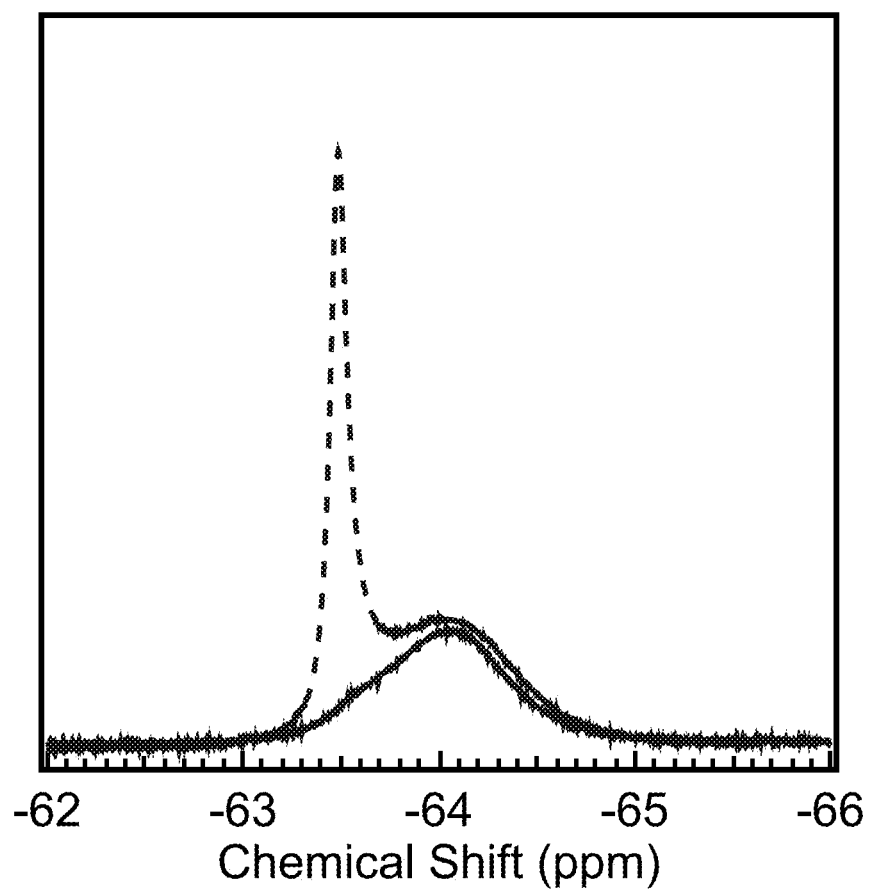
Figure 16D:
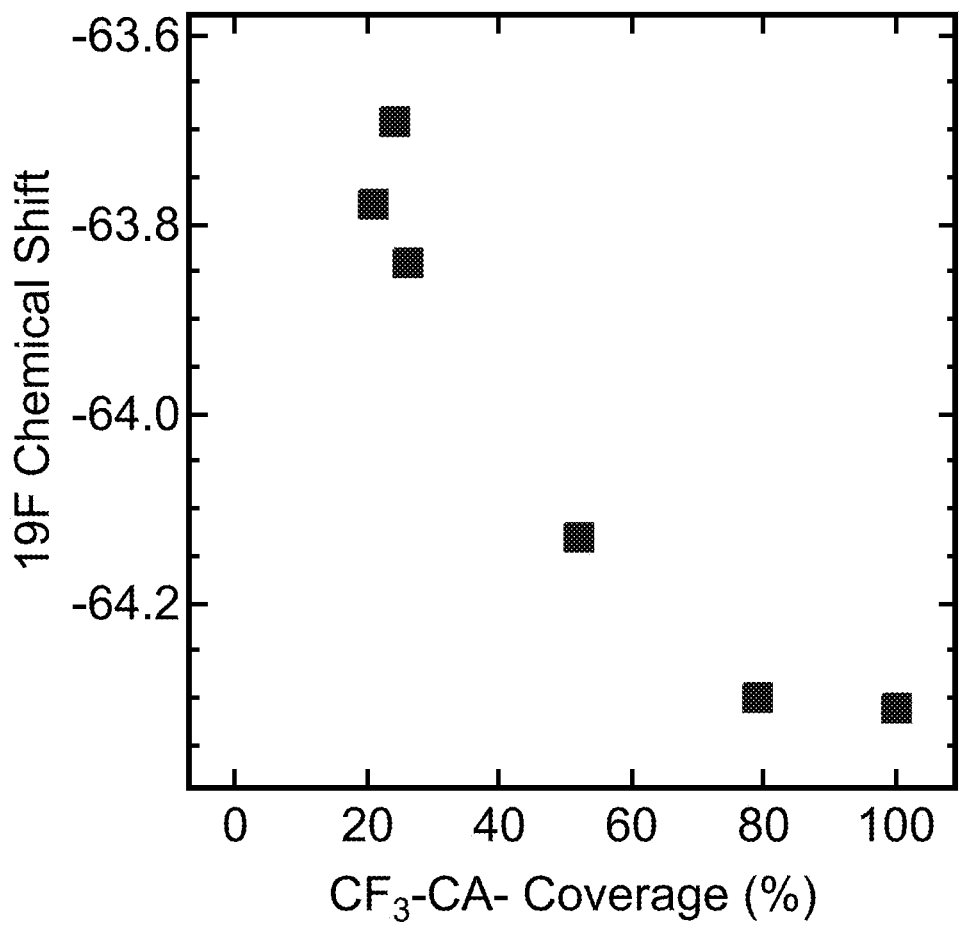
Figure 17:
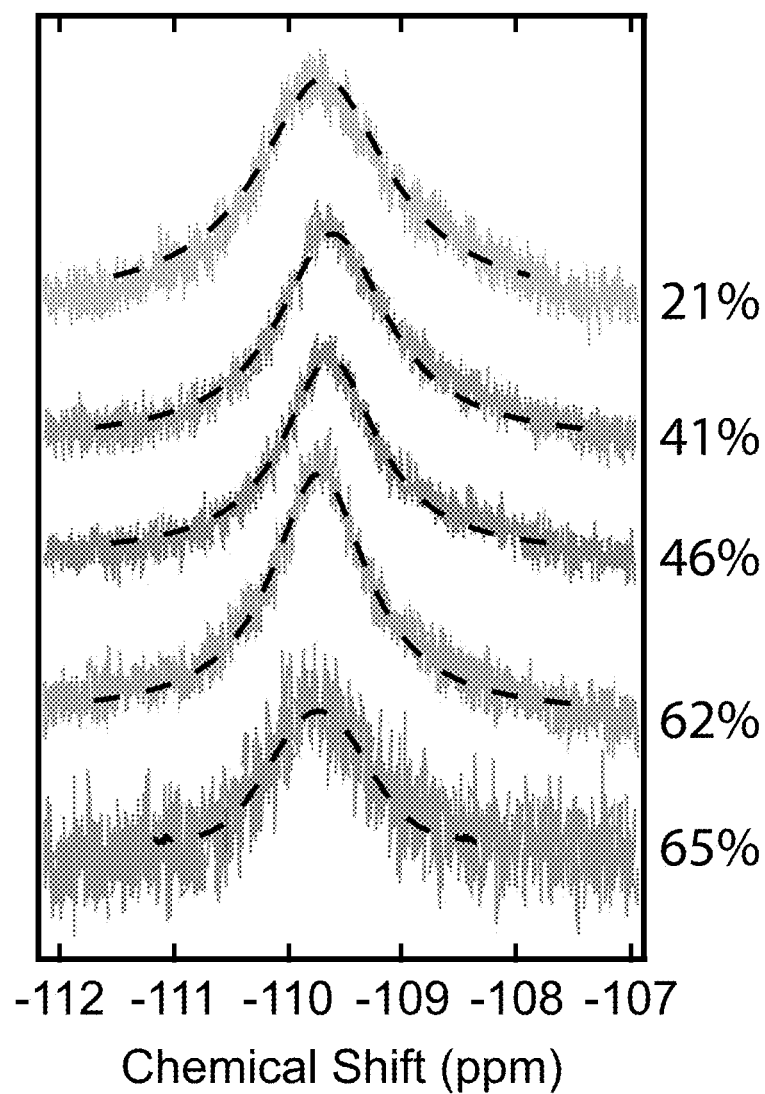
FIG. 17 illustrates the $^{19}F$ $\{^1H\}$ spectra of the at 21, 41, 46, 62, and 65% PbS/2,6-F-CA ($\delta$=−109.85−−109.7 ppm), according to some embodiments of the present disclosure. The peaks were fit and integrated to determine the number of bound 2,6-F-CA. The peaks fit well to a single Lorentzian peak, indicating the samples were fully purified. No evidence of free ligand is detected.

The negative coupling term, $\Delta J$, is indicative of how likely patches form during the ligand exchanges. In the Ising model an order-disorder phase transition occurs when the coupling energy is less than $-0.44\ k_BT$. For the modified model described herein, the phase transition occurs at the same coupling energy (see FIG. 15). The implications are that for ligands whose coupling energy $<-0.44\ k_BT$ it is very unlikely to find one cinnamate ligand surrounded by only oleate ligands. Rather, cinnamates will tend to group together (see FIG. 9 and FIG. 15), that is, form segregated ligand patches. This knowledge can be used to build a Janus ligand shell, which is demonstrated using $CF_3$-CAH, which has a coupling energy of −0.46 $k_BT$ and $^{19}F$ NMR and 3,5-F-CAH with a coupling energy of −0.6 $k_BT$ using 2-dimensional NMR (vida infra).

Patchy and Janus ligand structures may be studied using NMR spectroscopy, based on the composition dependence of the chemical shift, that is the chemical shift of the substituent groups depend sensitively upon their chemical environment, isolated cinnamates (or solvated CA-) will exhibit a different shift than will cinnamates that are packed together with nearest neighbor cinnamates. The 1-D NMR chemical shift of the ligands is expected to exhibit a linear, sigmoidal or inverse dependence on the coverage, depending on whether the ligand morphology is random, striped, or Janus structured, respectively. Here, the $^{19}F$ chemical shift dependence on the coverage of $CF_3$-$CA^-$ was measured (see FIG. 14A) and compared to 2,6-F-$CA^-$ (see FIG. 14B) on 3.4 nm PbS nanocrystals (see FIGS. 16A-16D and FIG. 17 for raw data). A random distribution of new ligands in oleate ligands would exhibit a linear dependence of its chemical-shift as the environment is a linear extrapolation of purely isolated to all cinnamate neighbors. However, the NMR shift, δ, for the $CF_3$-$CA^-$ is not linear in the extent of exchange, $x_A$, and can be modeled by Eq. 5 which accounts for the partitioning of the ligands:

$$\delta = \delta_B + \frac{(\delta_I - \delta_B)t}{2rx_A} \tag{5}$$

where, $\delta_B$ is the shift when the ligand is surrounded by like species, $\delta_I$ is the shift when the ligand resides at the interface with unlike species, t is the thickness of the interfacial region (taken here to be 0.61 nm, the average distance between ligands), and r is the nanocrystal radius. The best-fit (solid trace) parameters are $\delta_I$=−63.66 and $\delta_B$=−64.38. The non-linear dependence occurs because at the early exchanges the chemical environment is changing as the ligand patch is small in a sea of non-similar ligands while at later times larger patches form and the chemical environment is not changing much. In contrast, FIG. 14B shows that the NMR shift exhibits a linear dependence with the exchange 2,6-F-$CA^-$ whose coupling energy is too low to form segregated patches and the shift is linearly proportional to the extent of exchange.

Figure 14C:
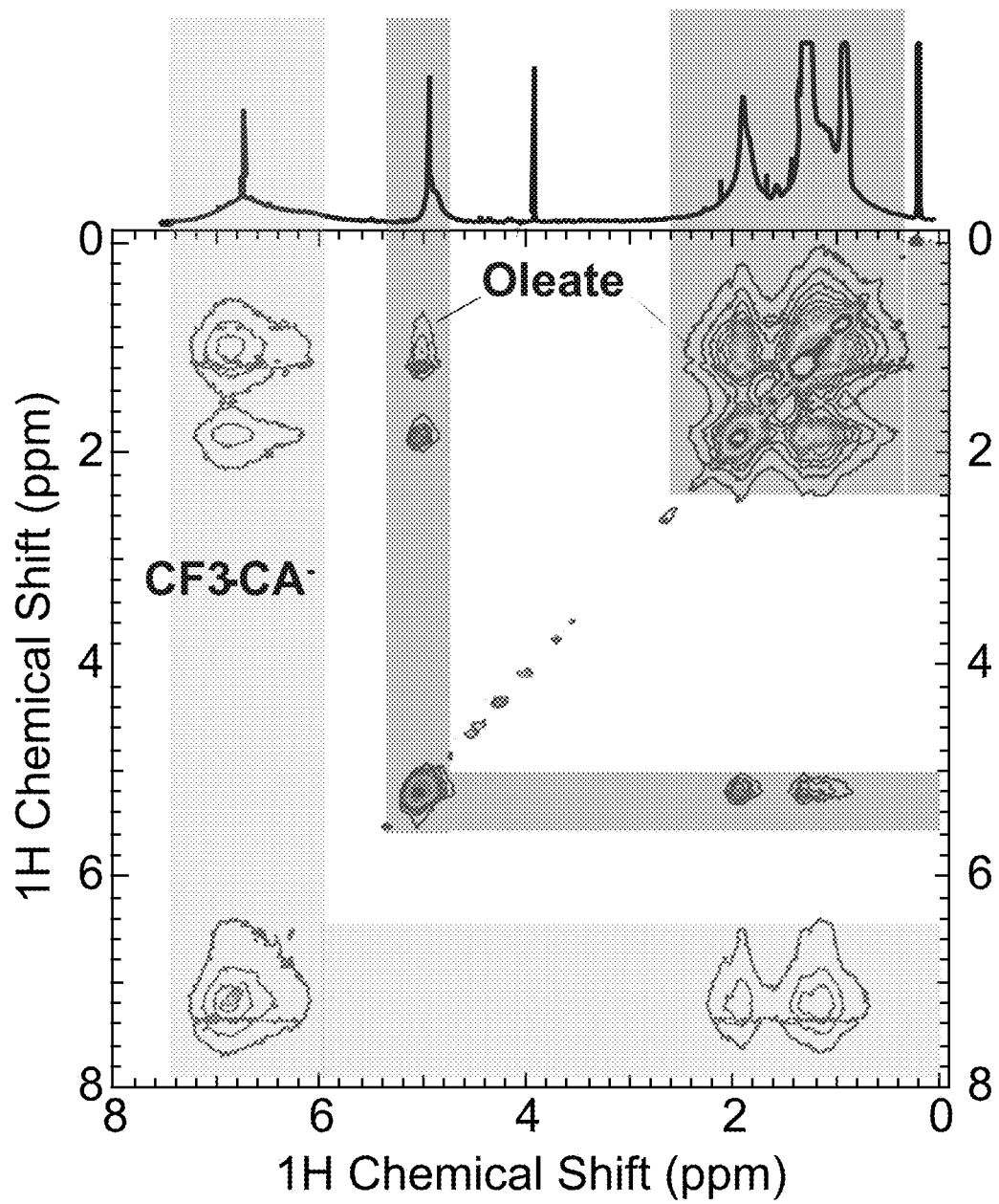
Figure 14D:
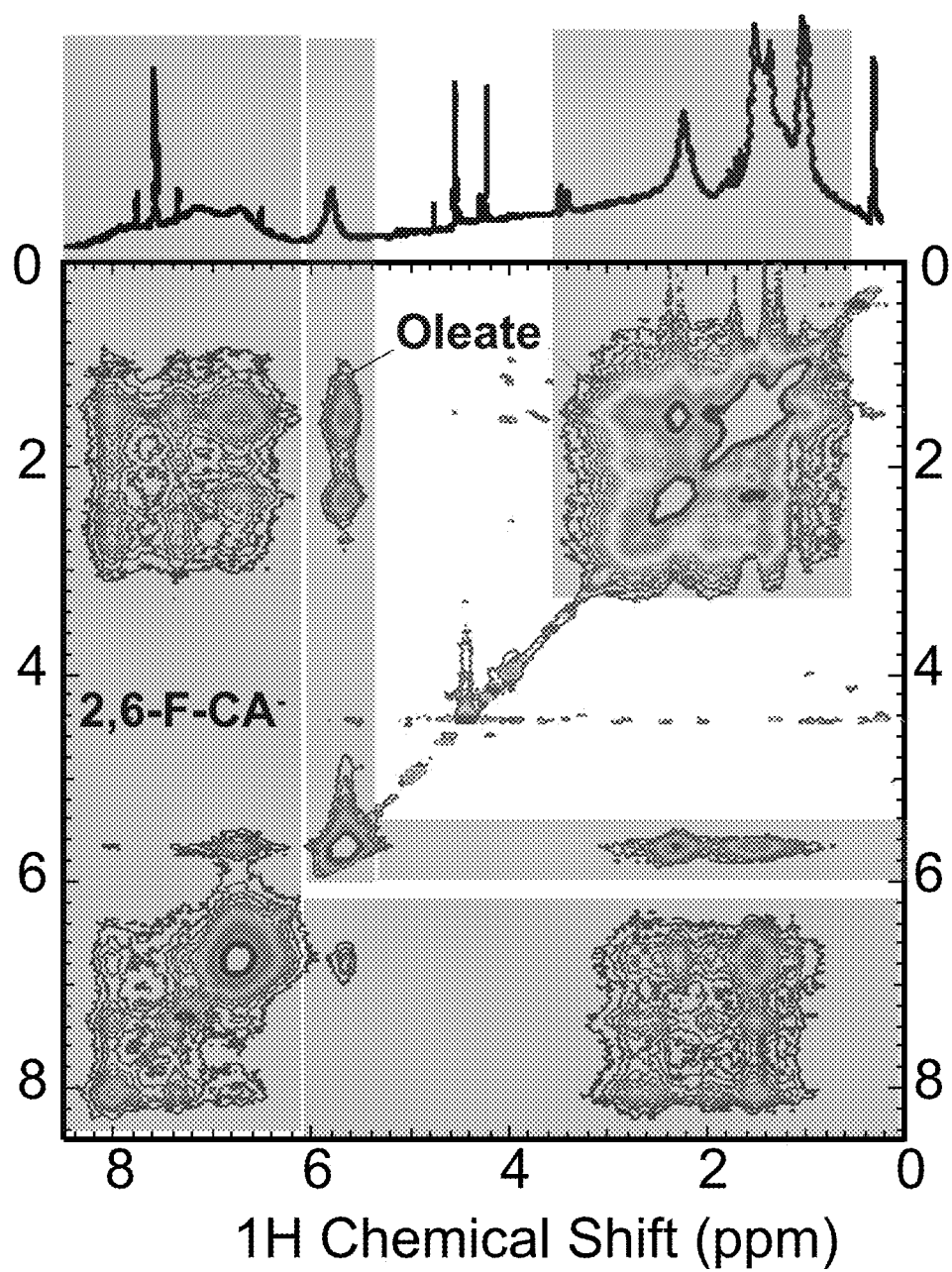
Figure 18:
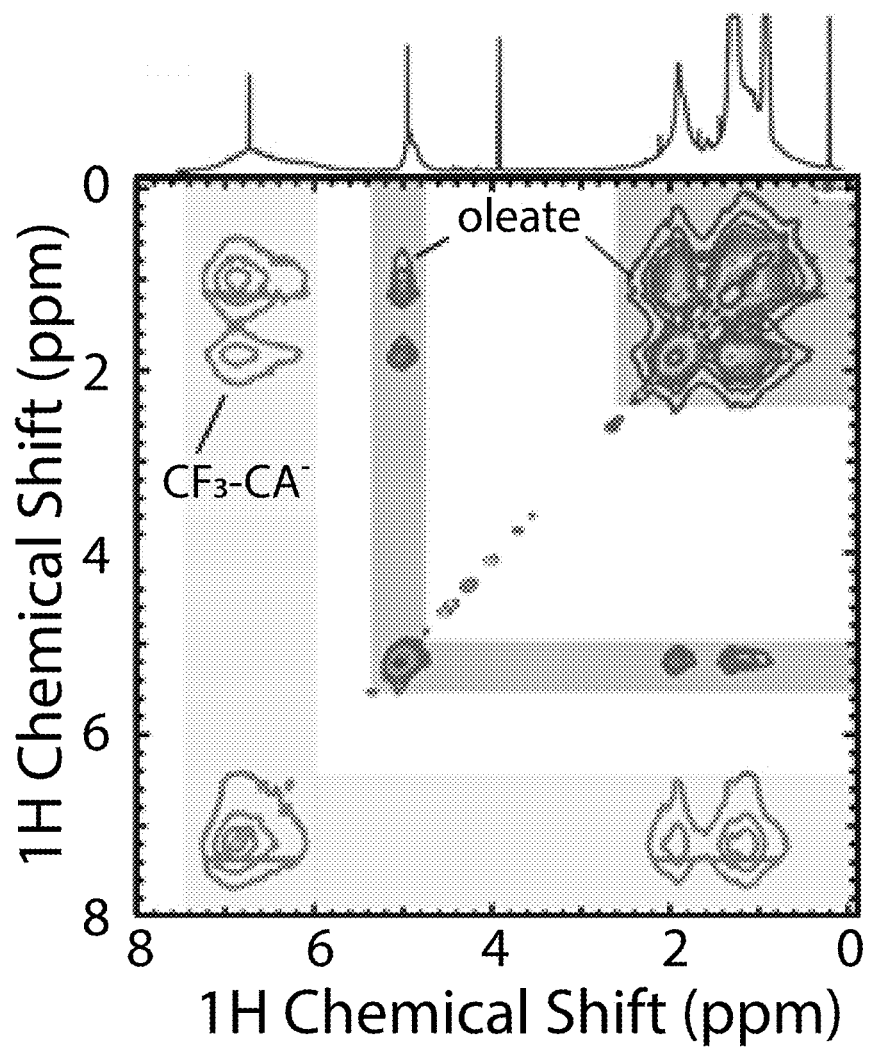
FIG. 18 illustrates NOESY spectrum of the PbS/(69%) $CF_3$-CA$^-$ with resonances from the oleate methyl and ethyl groups ($\delta$=1-2.5 ppm), oleate vinyl ($\delta$=5.4 ppm), cinnamate aryl group ($\delta$=5.8-8 ppm), and standard peaks (ferrocence $\delta$=4.15 ppm) and solvent (chloroform-d $\delta$=7.2 ppm), according to some embodiments of the present disclosure. The coupling energy of the $CF_3$-CA$^-$ is −0.46 $k_BT$.

In addition, 2D NMR experiments were performed on nanocrystals with mixed ligand coverage. Adjacent ligands on a nanoparticle surface will likely demonstrate a nuclear Overhauser effect (NOE), which arises from through-space interactions, rather than through-bond interactions. For a nanoparticle surface with mixed ligand composition, ligand shells with random arrangement may exhibit strong cross peaks arising from interactions with the opposite ligand, whereas the Janus ligand morphology shows little to no cross peaks. Mixed ligand composition samples were prepared using the same procedure described above, and acquired 2D NOESY (see FIGS. 14B and 14C) of 3,5-F-$CA^-$ (69%)/$OA^-$ (see FIG. 14C) and 2,6-F-$CA^-$(53%)/$OA^-$ (see FIG. 14D) mixed compositions, respectively (a NOSEY spectrum of $CF_3$-$CA^-$(43%)/$OA^-$ in shown in FIG. 18 with a 2 s delay and 0.3 s mixing time. The 3,5-F-$CA^-$(69%)/$OA^-$ spectrum shows a weak NOE coupling (see 14C, off-diagonal components for the 3,5-F-$CA^-$, shaded region, and oleate peaks, gray-shaded region) between the cinnamate and oleate ligands, while the 2,6-F-CA/$OA^-$ spectrum shows strong coupling (see FIG. 14D). A measure of the difference in magnitude, aside from the difference in contour colors, is shown by the well-defined structure in the NOE cross peaks for the 2,6-F-CA/$OA^-$ sample, which is not found in the 3,5-F-$CA^-$/$OA^-$ spectrum. While there are weak cross peaks found in the 3,5-F-$CA^-$/$OA^-$NOESY, they are not present at the magnitude shown in the 2,6-F-$CA^-$NOESY, and this is a direct indication that there are much fewer through space interactions on the latter particles. The differences in ligand length is most likely the explanation for the weak cross peaks in the 3,5-F-$CA^-$/$OA^-$ NOESY. Since the NOE phenomenon is observed for distances up to 5 Å, it is highly likely that the floppy oleate ligands at the Janus $CF_3$-$CA^-$/$OA^-$ interface are close enough to the cinnamate to give a small off-diagonal NOESY cross peak.

As shown herein, novel pyroelectric thin films were prepared with PbS quantum dots (nanocrystals) with Janus ligand shell. The spontaneous polarization of the material comes from the Janus ligand shell of PbS nanocrystals including the nonpolar oleic acid (OA), and electron withdrawing 3,5-difluorocinnamic acid (CAH). The electron withdrawing effect of the CAH leads to polarized PbS nanocrystals, which are then self-assembled into films under electric field. The pyroelectric current was observed when heating the film with 532 nm laser.

Figure 19A:
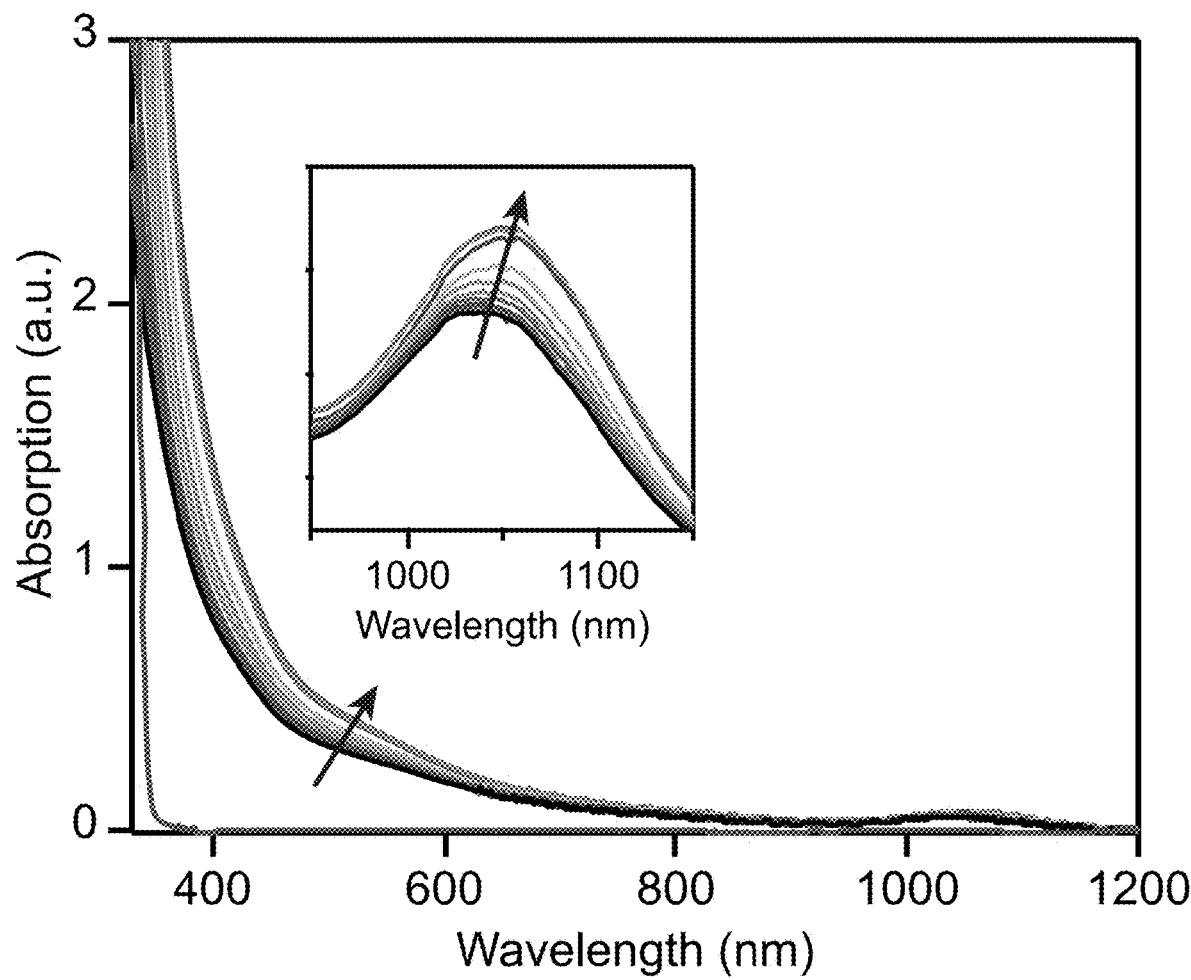
FIG. 19A illustrates absorption spectra of PbS nanocrystals after ligand exchange with 3,5-difluorocinnamic acid with different CAH/PbS mole ratios, according to some embodiments of the present disclosure. The inset is the zoom-in perspective of the first exciton peak of PbS nanocrystals. The ratio varies from pure CAH (i.e. zero PbS; labeled with asterisk) and pure PbS (i.e. zero CAH), and ratios of CAH/PbS from 1 (i.e. 1:1), 2, 4, 8, 16, 31, 63, 125, 250, 500, and 1000. The arrows indicate the direction of increasing ratios.
Figure 19B:
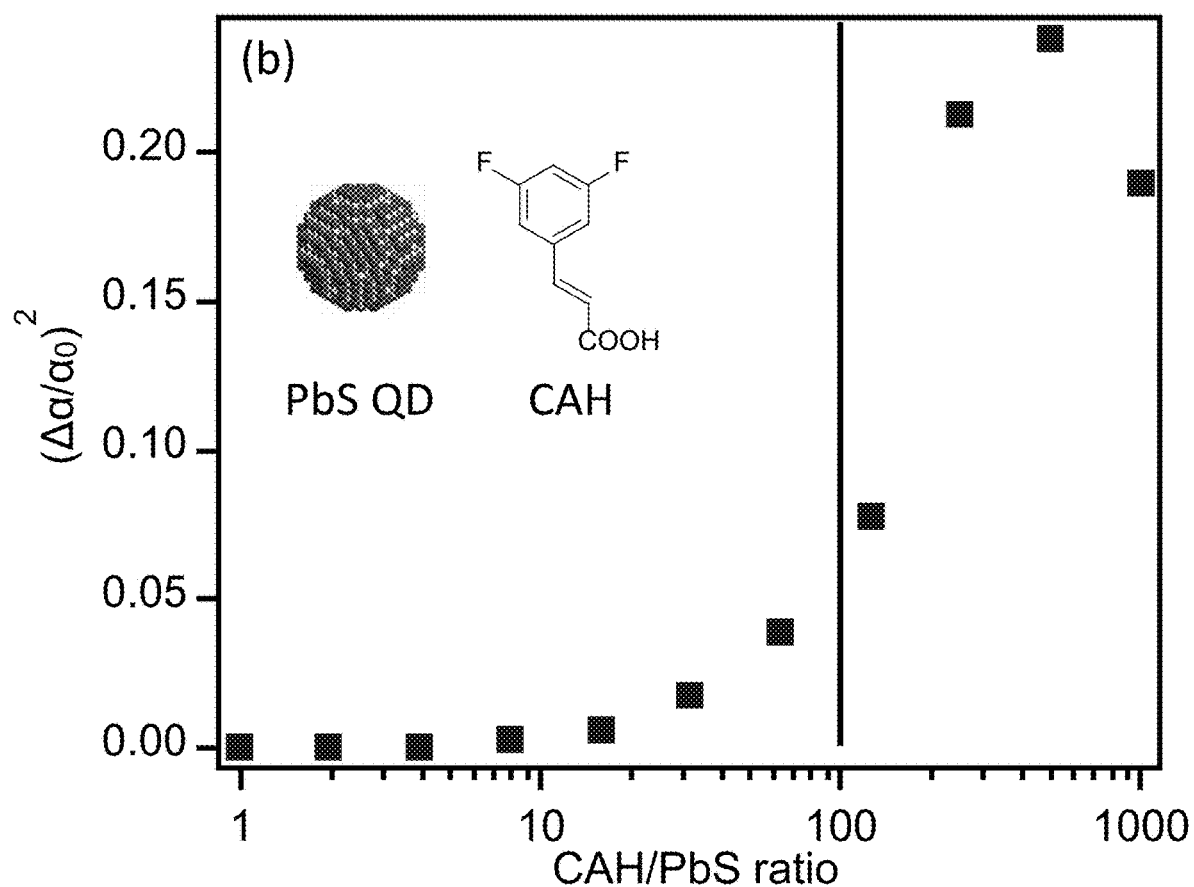
FIG. 19B illustrates the enhancement of integrated absorption (400-1200 nm) of PbS nanocrystals versus the ratio of CAH/PbS in ligand exchange, according to some embodiments of the present disclosure. The dashed curve labels the CAH/PbS ratio of 100, which was the condition used for preparing Janus PbS nanocrystals for NMR and pyroelectric measurements.

The ligand exchange condition that yields Janus ligand shell was confirmed with absorption spectra. Loading conjugated ligands on PbS nanocrystals resulted in a broad enhancement of the absorbance of nanocrystals. The enhancement of the absorptivity of nanocrystals is due to the ligand-to-nanocrystal charge transfer interaction. FIG. 19A presents the absorption of PbS nanocrystals after ligand exchange reaction with 3,5-difluorocinnamic acid (CAH). The absorptivity of nanocrystals enhances with the increase of the CAH/PbS ratio in ligand exchange. Because of the absorption feature of CAH molecule, blue to 400 nm, the area under the curve from 400 nm to 1200 nm were integrated as the absorbance enhancement from PbS nanocrystals. There is a square-root correlation between the nanocrystal absorbance enhancement and the number of bound CAH ligands. Therefore, $(\Delta_a/\alpha)^2$ reflects the number of bound ligands, where $\Delta\alpha$ is the enhanced absorbance of PbS/CAH nanocrystals compared to PbS/OA nanocrystals, and do is the absorption of PbS/OA nanocrystal. The red shift of the first exciton peak was also observed as CAH binds to PbS nanocrystals, which is due to the delocalization of nanocrystal excitons to ligands. FIG. 19B presents the relationship between the ratio of CAH/PbS in ligand exchange, and $(\Delta\alpha/\alpha)^2$ which characterizes the number of bound ligands. $(\Delta\alpha/\alpha)^2$ increased with the increase of CAH concentration in ligand exchange and reached a maximum when the CAH/PbS ratio equaled 500, and then dropped after that. With the increase of surface loading of CAH ligand, the coupling between CAH ligands was stronger, which diminished the coupling between nanocrystals and CAH, therefore leading to a drop of $(\Delta\alpha/\alpha)^2$. In this study, a CAH/PbS ratio of 100 was chosen as the ligand exchange condition to construct PbS nanocrystals having a Janus ligand shell.

Figure 20:
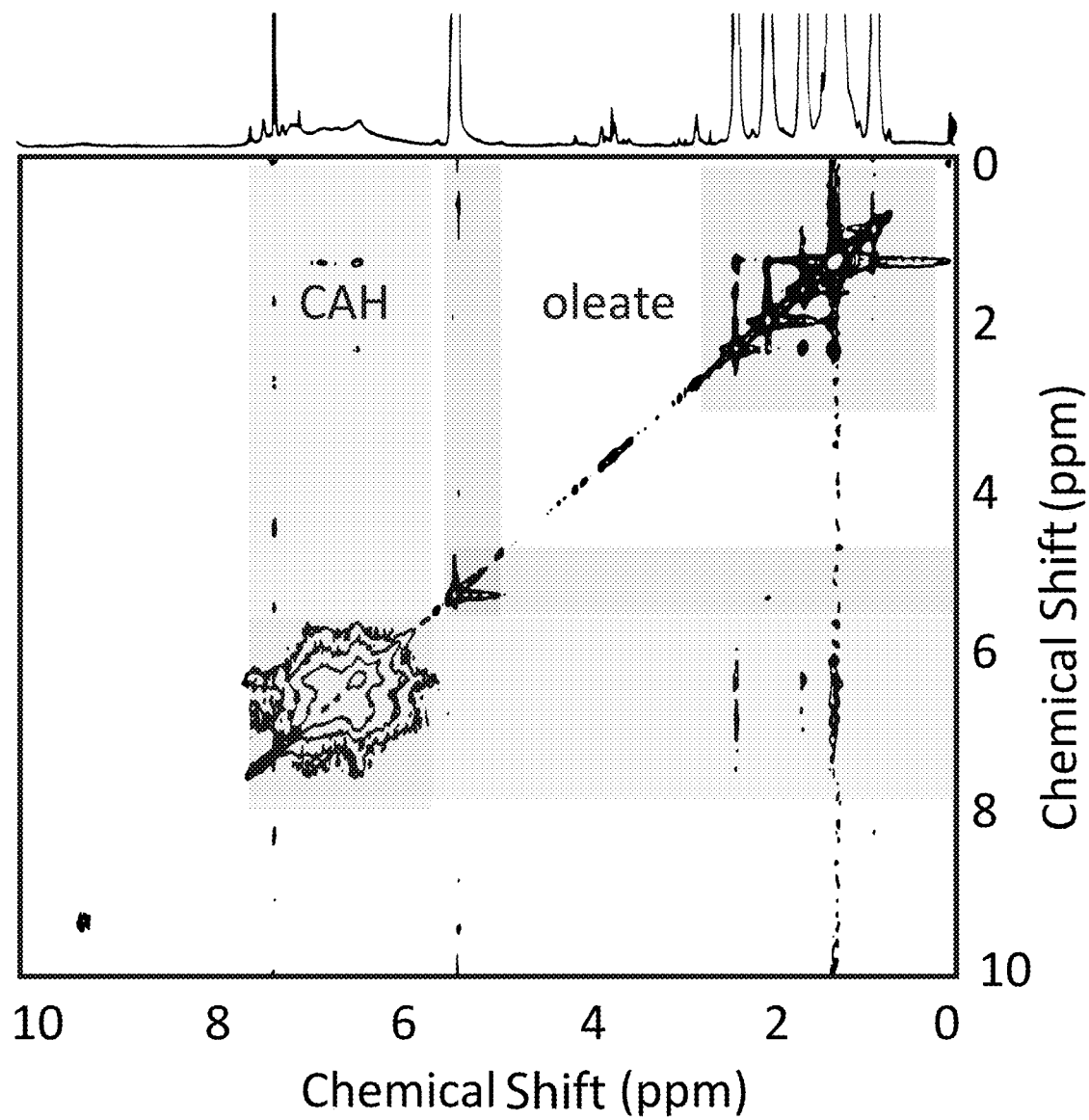
FIG. 20 illustrates 2D nuclear Overhauser effect spectroscopy (NOESY) of PbS nanocrystals with 3,5-difluorocinnamic acid/OA Janus ligand shell, according to some embodiments of the present disclosure. The ligand exchange condition follows the one in FIG. 19B with the CAH/PbS ratio of 100, which corresponds to 50% coverage of CAH.

2D NMR spectroscopy was used to confirm the formation of ligand shell on PbS nanocrystals. FIG. 20 shows the 2D nuclear Overhauser effect spectroscopy (NOESY) of PbS nanocrystals after ligand exchange with CAH ligands with a 100 CAH/PbS ratio. NOESY characterizes the through-space interaction of mixed ligand shells on PbS nanocrystals. The strong cross-peaks should be observed when OA and CAH ligands are randomly distributed, and the absence or reduced amount of cross-peaks reveals the presence of Janus ligand shells. As shown in FIG. 20, the bound CAH ligands shows a broad peak in aromatic region from 5.5 to 8 ppm, and peaks in the aliphatic region reflect the oleic acid ligands. Cross-peaks were small, indicating the formation of Janus ligand shells. In contrast, strong cross-peaks were observed on PbS nanocrystals ligand exchanged with p-cyanocinnamic acid. The ligand exchange with CAH/PbS ratio of 100 corresponds to a surface coverage of about 35%. A coverage lower than 50% can minimize the randomly distributed CAH ligand, and therefore maximize the dipole moment of the Janus PbS nanocrystals.

Figure 21:
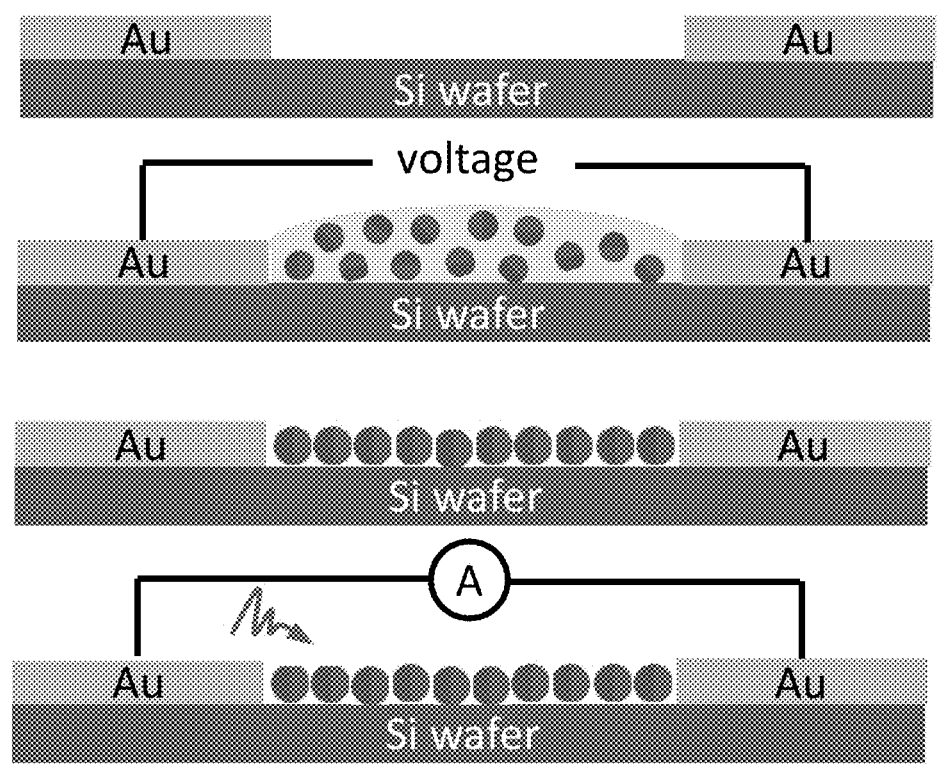
FIG. 21 illustrates the construction of pyroelectric films of Janus PbS nanocrystals under electric field, according to some embodiments of the present disclosure.

Pyroelectric thin films were prepared by the self-assembly of PbS nanocrystals with Janus ligand shell under electric field, as shown in FIG. 21. PbS nanocrystals after ligand exchange with CAH were washed with acetone as antisolvent and redispersed in toluene before use. The device was fabricated by the deposition of two 50 nm thick gold electrodes on silicon wafer. Then, the Janus PbS nanocrystal solution was drop-cast on the channel between the two electrodes with a voltage applied to the electrodes using a source meter. The spontaneous dipole moment of Janus PbS nanocrystals allowed them to align with the direction of the electric field. As the toluene evaporated, a self-assembled nanocrystal film having close-packed and head-to-tail structures was formed, with the ensemble dipole moment pointing from one electrode to the other. The pyroelectric effect of the device was tested using a 5 mW 532 nm continuous wave laser to illuminate the film while monitoring the device current. Due to the heating effect of the 532 nm laser, the ordered nanocrystal array tended to randomly rearrange and the ensemble dipole moment changed, which resulted in a change in the net charge distributions of the two ends of the film. The pyroelectric current was observed under short circuit condition.

Figure 22A:
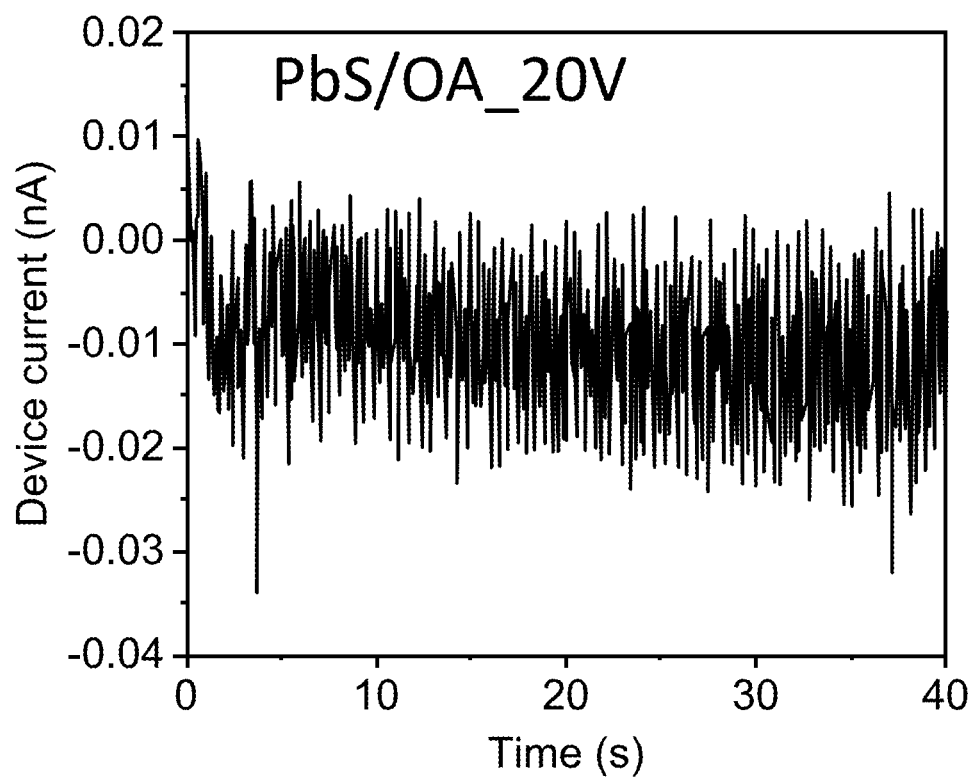
FIGS. 22A-22C illustrate the current response from pyroelectric Janus PbS thin films triggered by the illumination of 5 mW 532 nm laser, according to some embodiments of the present disclosure. The pulse-like current was generated at the moment the laser was turned on or off.
Figure 22B:
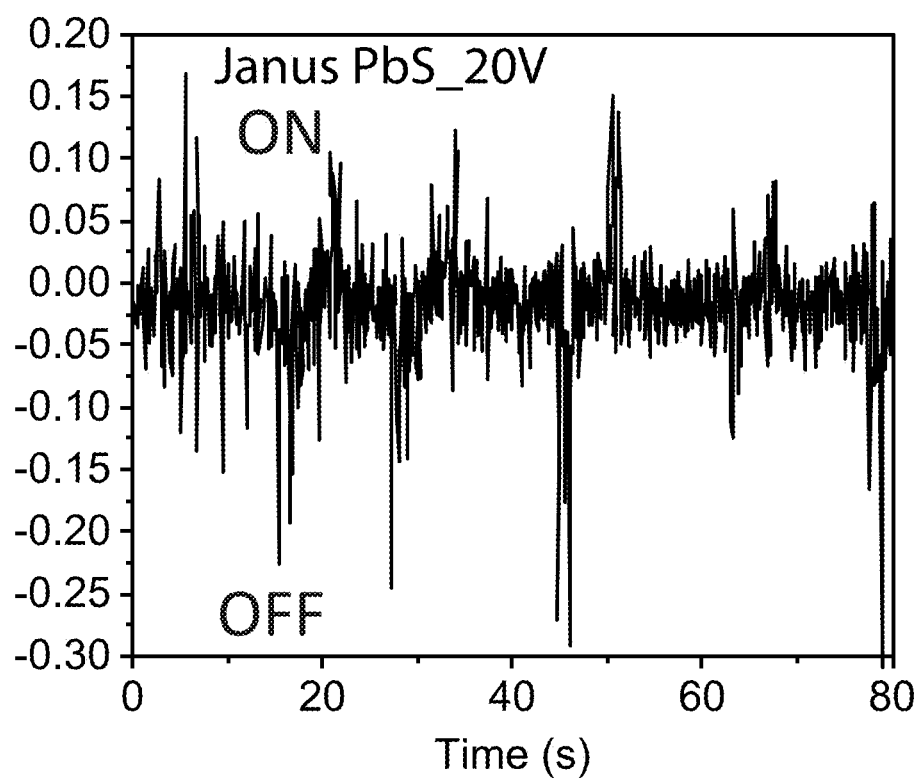

The pyroelectric current was observed by illuminated the nanocrystal thin films with 532 nm light. For the device prepared with Janus PbS nanocrystals self-assembled under 20 V (see FIG. 22B), switching the laser between an on-condition and an off-condition, corresponding positive and negative current pulses were observed. The pulse-like signal was generated only at the moment the laser was switched from on to off. This is because the film started to heat when the laser was on, and the temperature fluctuation triggered a change of the spontaneous polarization of the film, which generated the pyroelectric current. The temperature of the film eventually reached an equilibrium, where dT/dt was equal to zero and no pyroelectric current was observed. The negative current was observed when laser was turned off, which corresponded to a cooling process of the film to room temperature. As the film was only tens of nanometer thick, and the channel length was tens of micrometers, the heating and cooling processes were fast, so that the dynamics were not resolvable within the timescales shown in FIGS. 22A-22C, which explains the pulse-like signal that was observed. The pyroelectric current in this case can be distinguished from a photocurrent, which would be observed as a continuous signal instead of a pulse. As a control, the pyroelectric test was performed on a device of PbS/OA nanocrystals prepared and measured under the same conditions as presented in FIG. 22A. No current was observed on this device.

Figure 22C:
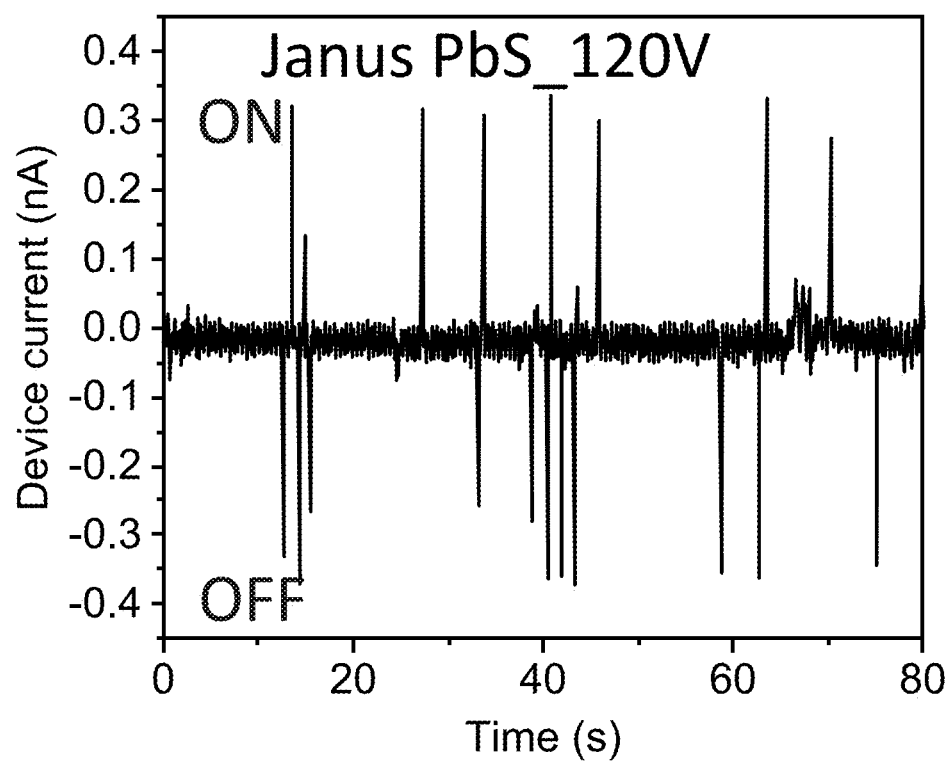
Figure 23:
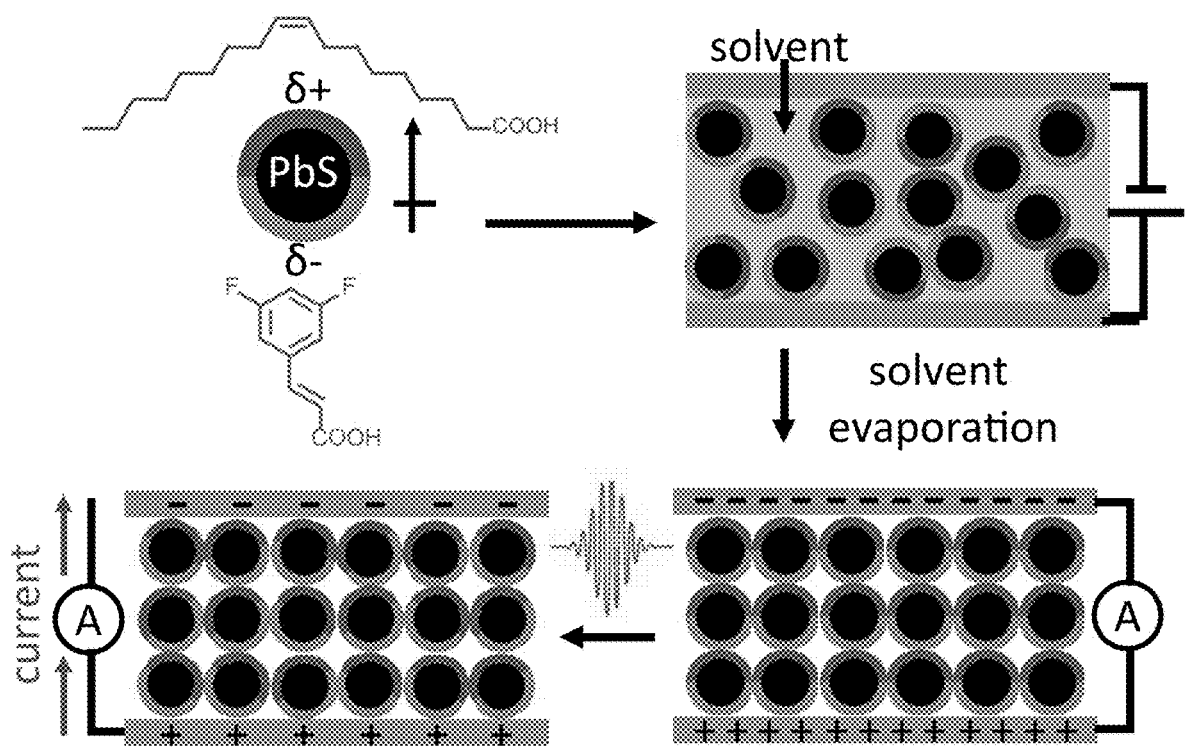
FIG. 23 illustrates the construction of pyroelectric films of Janus PbS nanocrystals under electric field, according to some embodiments of the present disclosure.

The pyroelectric effect of Janus nanocrystal thin films may be enhanced by better aligned nanocrystal arrays assembled under stronger electric fields. FIG. 22C presents the pyroelectric current generated from a Janus nanocrystal film assembled under 120 V. Compared with the results in FIG. 22B in which nanocrystals were self-assembled under 20 V, the pyroelectric current was about 3 times stronger. This is because the self-assembly of Janus nanocrystals to perfect crystal-like structures is dependent on the strength of the electric field. A stronger voltage allows each nanocrystal to be better aligned with the electric field, which yields stronger spontaneous polarization of the resultant films. Therefore, the change of polarization when heated or cooled was more prominent, so that a stronger pyroelectric effect was observed.

Methods:

Materials: All chemicals were used as received without further purification unless noted. Anhydrous octane (≥99%), anhydrous diethylene glycol dimethyl ether (diglyme, 99.5%), N,N'-diphenylthiourea (98%), anhydrous toluene (99.5%), anhydrous tetrachloroethylene (TCE, ≥99.9%), anhydrous methyl acetate (MeOAc, 99%), anhydrous hexane (≥99%), anhydrous dichloromethane (DCM, ≥99.8%), anhydrous acetonitrile (ACN, 99.8%), anhydrous isopropanol (IPA, 99.5%), anhydrous chloroform-d ($CDCl_3$, ≥99.8%), Acetone (≥99.9%, degassed), anhydrous tetrahydrofuran (THF, ≥99.9%), 1,1,1,3,3,3-Hexafluoro-2-propanol (HFIP, ≥99%, degassed), trans-cinnamic acid (4-H-CAH, ≥99%), trans-2,6-difluorocinnamic acid (2,6-F-CAH, 99%), trans-3,5-difluorocinnamic acid (3,5-F-CAH, 99%), trans-4-(trifluoromethyl) cinnamic acid (4-$CF_3$-CAH, 99%), 4-methoxycinnamic acid, predominantly trans (4-$OCH_3$-CAH, 99%), 4-(dimethylamino) cinnamic acid, predominantly trans (4-$N(CH_3)_2$-CAH, 99%), ferrocene ($Cp_2Fc$, 98%), triethylamine (TEA, ≥99%), benzenethiol (4-H-SH, ≥98%), 4-aminobenzenethiol (4-$NH_2$-SH, 97%), and 4-methylbenzenethiol (4-$CH_3$-SH, 98%) were obtained from Sigma Aldrich. 4-(trifluoromethyl)benzenethiol (4-$CF_3$-SH, 97%) was obtained from Alfa Aesar. 4-(2,2-dicyanovinyl) cinnamic acid (4-$(CN)_2$-CAH).

TABLE 1

Solvent compositions for the various ligand exchanges

| Ligand ID | Ligand Solvent[1,2] |
|---|---|
| 4-$(CN)_2$-CAH | 5:1 ACN:IPA |
| 4-CN-CAH | 5:1 ACN:IPA |
| 4-$CF_3$-CAH | Acetone |
| 3,5-F-CAH | MeOAc |
| 4-H-CAH | DCM |
| 2,6-F-CAH | DCM |
| 4-$OCH_3$-CAH | 5:1 ACN:IPA |
| 4-$N(CH_3)_2$-CAH | 2:1 IPA:DCM |

[1]Heating and sonication were sometimes necessary to solubilize ligand.
[2]Addition of neat ligand solvent had no significant effect on nanocrystal absorbance spectrum in 6:1 ratios of DCM:ligand solvent.

Oleate capped PbS nanocrystal Synthesis: Oleate capped PbS nanocrystals were synthesized following a substituted thiourea protocol. In a nitrogen glove box, 8.81 g Pb(oleate)$_2$ and 150 mL anhydrous octane are added to a 2-neck 250 mL Schlenk flask and sealed. 1.74 g of N,N'-diphenylthiourea and 5 mL of diglyme are mixed in a 20 mL scintillation vial and sealed. Both vessels were brought to 95° C. in an oil bath under nitrogen and allowed to stir for ~30 minutes (both solutions were clear). The N,N'-diphenylthiourea diglyme solution is injected into the Pb(oleate)$_2$ octane solution under vigorous stirring and allowed to react for 60 seconds, removed and allowed to cool to room temperature. The flask is transferred to a nitrogen filled glovebox and dispersed in ~40 mL toluene and centrifuged at 7000 RPM for 10 minutes. The brown nanocrystal solution was decanted while the remaining dark pellets are discarded. To each centrifuge tube, approximately 30 mL of methyl acetate is added to precipitate the nanocrystals and then centrifuged at 7000 RPM for 10 minutes. The cycle of precipitation and redissolution using toluene and methyl acetate is repeated three times. The nanocrystal product is dried under vacuum and suspended in hexane for storage.

Constructing Absorption Isotherms: Briefly, optical absorbance spectra were collected using a UV-Vis-NIR spectrometer. A stock solution of 5-15 µM PbS nanocrystals in DCM, standardized from absorbance measurements taken in TCE, was prepared under ambient conditions. Separately, a stock ligand solution was prepared by dissolving a known amount of the ligand in a compatible solvent (see Table 1). The stock ligand solution was combined with neat ligand solvent in separate vials to make diluted ligand samples of varying ligand concentration. In a 2 mm path length cuvette, 0.1 mL of a diluted ligand solution was added to a 0.6 mL of the stock nanocrystal solution (always maintaining a constant sample volume of 0.7 mL). The sample was thoroughly mixed, and an absorbance spectrum was immediately taken. This protocol was followed for diluted ligand samples with ligand content ranging from 0-3000 ligands per nanocrystal per addition. Solution measurement and mixing was performed with calibrated micropipettes.

The absorption spectrum was integrated from 1.0 to 2.5 eV, starting below the nanocrystal 1S-exciton and ending prior to any R-CA$^-$/R-CAH ligand absorbance feature (see gray trace of Panel a of FIG. 8). $\Delta\alpha/\alpha$, increases as cinnamate ligands bind to the surface (see Panel b of FIG. 8), and at ligand equivalents larger than the number of OA$^-$ originally coordinating the nanocrystal surface (100 in these experiments, see dashed-line of Panel b of FIG. 8); suggesting the ligand exchanges are governed by an equilibrium between surface bound and free ligands that is driven towards surface bound R-CA$^-$ by the addition of excess R-CAH. To construct the ligand absorption isotherms we need to relate $\Delta\alpha/\alpha$, to the addition of one bound ligand to the nanocrystal surface.

EXAMPLES

Example 1. A nanocrystal comprising: a nanocrystal core; a first ligand coordinated to a first portion of a surface of the nanocrystal core, and a second ligand coordinated to a second portion of the surface, wherein: the second ligand comprises a first functionalized aromatic molecule.

Example 2. The nanocrystal of Example 1, wherein the first functionalized aromatic molecule comprises at least one of cinnamic acid (CAH) or a first functionalized CAH molecule.

Example 3. The nanocrystal of either Example 1 or 2, wherein the first functionalized CAH molecule comprises at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tert-butylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, or 3,4-(2,5-pyrrolidinedione) cinnamic acid.

Example 4. The nanocrystal of any one of Examples 1-3, wherein the first functionalized aromatic molecule comprises at least one of styrylphosphonic acid, 4-formylstyrylphosphonic acid, (4-(2,2-dicyanovinyl) styryl)phosphonic acid, 2,6-difluorostyrylphosphonic acid, 4-trifluoromethylstyrylphosphonic acid, 4-methoxystyrylphosphonic acid, 3-methylstyrylphosphonic acid, benzoic acid, 4-methylbenzoic acid, 4-mercaptobenzoic acid, 4-methoxybenzoic acid, 4-fluorobenzoic acid, 4-hydroxybenzoic acid, 4-nitrobenzoic acid, 4-cyanobenzoic acid, 4-formylbenzoic acid, 4-trifluoromethylbenzoic acid, 4-chlorobenzoic acid, 4-bromobenzoic acid, 4-iodobenzoic acid, 4-fluorobenzoic acid, 2,6-difluorobenzoic acid, trans-3-(3-thienyl) acrylic acid, 6,13-bis(triisopropylsilylethynyl)-pentacene-2-carboxylic acid, 6,13-bis(triisopropylsilylethynyl)-pentacene-2-acrylic acid, 6,11-bis(triisopropylsilylethynyl)-tetracene-2-carboxylic acid, 6,11-bis(triisopropylsilylethynyl)-tetracene-2-acrylic acid, 5,10-bis(triisopropylsilylethynyl)-anthracene-2-carboxylic acid, 5,10-bis(triisopropylsilylethynyl)-anthracene-2-acrylic acid, naphthalene-2-carboxylic acid, or naphthalene-2-acrylic acid.

Example 5. The nanocrystal of any one of Examples 1-4, wherein the first ligand comprises at least one of an alkyl carboxylate, an alkyl amine, an alkyl phosphine, an alkyl phosphonate, or an alkyl thiolate.

Example 6. The nanocrystal of any one of Examples 1-5, wherein the first ligand comprises oleic acid.

Example 7. The nanocrystal of any one of Examples 1-6, wherein the first ligand comprises a second functionalized aromatic molecule that is different than the first functionalized aromatic molecule.

Example 8. The nanocrystal of any one of Examples 1-7, wherein the second functionalized aromatic molecule comprises at least one of CAH or a second functionalized CAH molecule.

Example 9. The nanocrystal of any one of Examples 1-8, wherein: the second functionalized CAH molecule comprises at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tert-butylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, or 3,4-(2,5-pyrrolidinedione) cinnamic acid.

Example 10. The nanocrystal of any one of Examples 1-9, wherein: the second functionalized aromatic molecule comprises at least one of styrylphosphonic acid, 4-formylstyrylphosphonic acid, (4-(2,2-dicyanovinyl) styryl)phosphonic acid, 2,6-difluorostyrylphosphonic acid, 4-trifluoromethylstyrylphosphonic acid, 4-methoxystyrylphosphonic acid, 3-methylstyrylphosphonic acid, benzoic acid, 4-methylbenzoic acid, 4-mercaptobenzoic acid, 4-methoxybenzoic acid, 4-fluorobenzoic acid, 4-hydroxybenzoic acid, 4-nitrobenzoic acid, 4-cyanobenzoic acid, 4-formylbenzoic acid, 4-trifluoromethylbenzoic acid, 4-chlorobenzoic acid, 4-bromobenzoic acid, 4-iodobenzoic acid, 4-fluorobenzoic acid, 2,6-difluorobenzoic acid, trans-3-(3-thienyl) acrylic acid, 6,13-bis(triisopropylsilylethynyl)-pentacene-2-carboxylic acid, 6,13-bis(triisopropylsilylethynyl)-pentacene-2-acrylic acid, 6,11-bis (triisopropylsilylethynyl)-tetracene-2-carboxylic acid, 6,11-bis(triisopropylsilylethynyl)-tetracene-2-acrylic acid, 5,10-bis(triisopropylsilylethynyl)-anthracene-2-carboxylic acid, 5,10-bis(triisopropylsilylethynyl)-anthracene-2-acrylic acid, naphthalene-2-carboxylic acid, or naphthalene-2-acrylic acid.

Example 11. The nanocrystal of any one of Examples 1-10, wherein the nanocrystal core has an average particle size between 1 nm and 100 nm.

Example 12. The nanocrystal of any one of Examples 1-11, wherein the nanocrystal core has a shape comprising at least one of a spherical shape, a cylindrical shape, or an irregular shape.

Example 13. The nanocrystal of any one of Examples 1-12, wherein the nanocrystal core comprises at least one of a Group II element, a Group III element, a Group IV element, a Group V element, Group VI element, or a noble metal.

Example 14. The nanocrystal of any one of Examples 1-13, wherein the nanocrystal core comprises at least one of PbS, PbSe, PbTe, CdS. CdSe, CdTe. ZnS, ZnSe, ZnTe. HgS. HgSe, HgTe, GaN, GaP, GaAs, InP, InAs, Si, Ge, Au, Ag. Pt, Cu, Ni, $AgSbS_2$, $AgSbSe_2$, $CuInS_2$, $CuInSe_2$, CuInSSe, $CuZnS_3$, $Cu_2SnSe_3$, CZTS, CZTSe, or CZTSSc.

Example 15. The nanocrystal of any one of Examples 1-14, wherein the nanocrystal core comprises at least one of a uniformly mixed alloy type nanocrystal core, a core-shell type nanocrystal core, a dot-in-rod type nanocrystal core, a dot-on-rod type nanocrystal core, or a Janus particle type nanocrystal core.

Example 16. The nanocrystal of any one of Examples 1-15, wherein the first ligand is coordinated to the surface by at least one of a covalent bond, an ionic bond, a van der Waals interaction, a dipole-dipole interaction, or a hydrogen-bond.

Example 17. The nanocrystal of any one of Examples 1-16, wherein the second ligand is coordinated to the surface by at least one of a covalent bond, an ionic bond, a van der Waals interaction, a dipole-dipole interaction, or a hydrogen-bond.

Example 18. The nanocrystal of any one of Examples 1-17, wherein the first ligand is coordinated to the surface of the nanocrystal core by an ionic bond.

Example 19. The nanocrystal of any one of Examples 1-18, wherein the second ligand is coordinated to the surface of the nanocrystal core by an ionic bond.

Example 20. The nanocrystal of any one of Examples 1-19, wherein the second portion is between 10% and 90% of the surface.

Example 21. The nanocrystal of any one of Examples 1-20, wherein the second portion is between 30% and 70% of the surface.

Example 22. The nanocrystal of any one of Examples 1-21, wherein the second portion is between 40% and 60% of the surface.

Example 23. A method comprising: adding an exchange ligand to a first solution comprising a first solvent and a starting nanocrystal comprising a starting ligand coordinated to a surface of a nanocrystal core, wherein: the adding produces an exchanged nanocrystal in a second solution, the starting ligand and the exchange ligand have a ligand-ligand coupling energy less than −044 $k_BT$, where $k_B$ is the Boltzmann constant and T is the temperature in Kelvin, the exchange ligand comprises a functionalized aromatic molecule, the nanocrystal core comprises at least one of a Group II element, a Group III element, a Group IV element, a Group V element, Group VI element, or a noble metal, the exchange ligand replaces at least a portion of the starting ligand coordinated to a portion of the surface, and the exchange ligand coordinates to the portion of the surface to produce the exchanged nanocrystal.

Example 24. The method of Example 23, wherein the first solution is maintained at a temperature between 20° C. and 30° C.

Example 25. The method of either Example 23 or 24, wherein the exchange ligand is added at a ratio of moles of exchange ligand to moles of nanocrystal core between 1:10 and 1000:1.

Example 26. The method of any one of Examples 23-25, wherein the ratio is between 1:1 and 100:1.

Example 27. The method of any one of Examples 23-26, wherein the ratio is between 2:10 and 5:1.

Example 28. The method of any one of Examples 23-27, further comprising, prior to the adding: preparing the first solution comprising the nanocrystal core, the starting ligand, and the first solvent to produce the starting nanocrystal, wherein: the first solvent has a high solubility for the nanocrystal core.

Example 29. The method of any one of Examples 23-28, wherein the first solvent comprises at least one of a polar solvent or a non-polar solvent.

Example 30. The method of any one of Examples 23-29, wherein the first solvent comprises at least one of pentane, hexane, heptane, octane, cyclohexane, toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, or water.

Example 31. The method of any one of Examples 23-30, wherein the exchange ligand comprises at least one of cinnamic acid (CAH) or a first functionalized CAH molecule.

Example 32. The method of any one of Examples 23-31, wherein the first functionalized CAH molecule comprises at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tert-butylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, or 3,4-(2,5-pyrrolidinedione) cinnamic acid.

Example 33. The method of any one of Examples 23-32, wherein the starting ligand comprises at least one of an alkyl carboxylate, an alkyl amine, an alkyl phosphine, an alkyl phosphonate, or an alkyl thiolate.

Example 34. The method of any one of Examples 23-33, wherein the starting ligand comprises oleic acid.

Example 35. The method of any one of Examples 23-34, wherein the starting ligand is different than the exchange ligand.

Example 36. The method of any one of Examples 23-35, wherein the starting ligand comprises at least one of CAH or a second functionalized CAH molecule.

Example 37. The method of any one of Examples 23-36, wherein: the second functionalized CAH molecule comprises at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tertbutylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, or 3,4-(2,5-pyrrolidinedione) cinnamic acid.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A nanocrystal comprising:
   a nanocrystal core comprising a mixed alloy; and
   a Janus ligand shell comprising a first ligand coordinated to a first portion of a surface of the nanocrystal core and a second ligand coordinated to a second portion of the surface, wherein:
   the first ligand comprises at least one of an alkyl carboxylate, an alkyl phosphonate, an alkyl thiolate, or a combination thereof, and
   the second ligand is different than the first ligand.

2. The nanocrystal of claim 1, wherein the second ligand comprises at least one of cinnamate, a functionalized cinnamate, or a combination thereof.

3. The nanocrystal of claim 2, wherein the functionalized cinnamate comprises a carboxylate of at least one of 2,3,4,5,6-pentafluorocinnamic acid, 3,5-bis(trifluoromethyl) cinnamic acid, 4-(2,2-dicyanovinyl) cinnamic acid, 4-nitrocinnamic acid, 4-cyanocinnamic acid, 3,5-difluoro-4-trifluoromethyl cinnamic acid, 4-formylcinnamic acid, 4-trifluoromethylcinnamic acid, 3,5-difluorocinnamic acid, 4-chlorocinnamic acid, 4-bromocinnamic acid, 4-iodocinnamic acid, 4-fluorocinnamic acid, cinnamic acid, 4-mercaptocinnamic acid, 4-carboxycinnamic acid, 4-hydroxycinnamic acid, 3,5-dimethoxy-4-hydroxycinnamic acid, 4-methylcinnamic acid, 4-ethylcinnamic acid, 4-tertbutylcinnamic acid, 2,6-difluorocinnamic acid, 4-methoxycinnamic acid, 2,6-difluoro-4-methoxycinnamic acid, 4-dimethylaminocinnamic acid, 4-aminocinnamic acid, alpha-cyano-4-dimethylaminocinnamic acid, 4-(di-(4-methoxyphenyl)amino) cinnamic acid, 3,4-(2,5-pyrrolidinedione) cinnamic acid, or a combination thereof.

4. The nanocrystal of claim 1, wherein the first ligand is an alkyl carboxylate.

5. The nanocrystal of claim 1, wherein the first ligand is oleate.

6. The nanocrystal of claim 1, wherein the nanocrystal core has an average particle size between 1 nm and 100 nm.

7. The nanocrystal of claim 1, wherein the mixed alloy comprises at least two of a Group II element, a Group III element, a Group IV element, a Group V element, Group VI element, a noble metal, or a combination thereof.

8. The nanocrystal of claim 7, wherein the mixed alloy comprises at least one of PbS, PbSe, PbTe, CdS, CdSe, CdTe, ZnS, ZnSe, ZnTe, HgS, HgSe, HgTe, GaN, GaP, GaAs, InP, InAs, Si, Ge, Au, Ag, Pt, Cu, Ni, $AgSbS_2$, $AgSbSe_2$, $CuInS_2$, $CuInSe_2$, $CuInSSe$, $Cu_2SnS_3$, $Cu_2SnSe_3$, CZTS, CZTSe, or CZTSSe, or a combination thereof.

9. The composition of claim 8, wherein the mixed alloy core comprises at least one of PbS, PbSe, or a combination thereof.

10. The nanocrystal of claim 1, wherein the second portion is between 10% and 90% of the surface.

11. The composition of claim 10, wherein the second portion is between 30% and 70% of the surface.

12. A method comprising:
    adding a molecule to a first solution comprising a first solvent and a starting nanocrystal, wherein:
    the starting nanocrystal comprises a mixed alloy core and a starting ligand coordinated to a surface of the mixed alloy core,
    the starting ligand comprises at least one of an alkyl carboxylate, an alkyl phosphonate, an alkyl thiolate, or a combination thereof,
    the adding results in at least a portion of the molecule forming an exchange ligand that is different than the starting ligand,
    the starting ligand and the exchange ligand have a ligand-ligand coupling energy less than 0.44 $k_B T$, where $k_B$ is the Boltzmann constant and T is the temperature in Kelvin, and
    the adding results in the forming of a nanocrystal comprising the mixed alloy core and a Janus ligand shell comprising the starting ligand coordinated to a first portion of the surface and the exchange ligand coordinated to a second portion of the surface.

13. The method of claim 12, wherein the first solution is maintained at a temperature between 20° C. and 30° C.

14. The method of claim 12, wherein the adding of the molecule results in a ratio of moles of exchange ligand to moles of mixed alloy core between 1:10 and 1000:1.

15. The method of claim 14, wherein the ratio is between 1:1 and 100:1.

16. The method of claim 14, wherein the exchange ligand comprises at least one of cinnamate, a functionalized cinnamate, or a combination thereof.

17. The method of claim 12, further comprising, prior to the adding:
- preparing the first solution comprising the mixed alloy core, the starting ligand, and the first solvent to produce the starting nanocrystal, wherein:
- the first solvent has a high solubility for the mixed alloy core.

18. The method of claim 12, wherein the first solvent comprises at least one of pentane, hexane, heptane, octane, cyclohexane, toluene, benzene, chlorobenzene, dichlorobenzene, nitrobenzene, dichloromethane, tetrachoroethylene, chloroform, carbon tetrachloride, acetone, acetonitrile, methyl acetate, ethyl acetate, tetrahydrofuran, diethyl ether, methanol, ethanol, propanol, butanol, N-methylformamide, N,N-dimethylformamide, dimethyl sulfoxide, water, or a combination thereof.

19. The method of claim 12, wherein the starting ligand is an alkyl carboxylate.

20. The method of claim 19, wherein the starting ligand is oleate.

\* \* \* \* \*